(12) United States Patent
Luo

(10) Patent No.: US 12,351,812 B2
(45) Date of Patent: Jul. 8, 2025

(54) RECOMBINANT ONCOLYTIC VIRUS

(71) Applicant: Georgia State University Research Foundation, Inc., Atlanta, GA (US)

(72) Inventor: Ming Luo, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 853 days.

(21) Appl. No.: 16/614,441

(22) PCT Filed: May 16, 2018

(86) PCT No.: PCT/US2018/032915
§ 371 (c)(1),
(2) Date: Nov. 18, 2019

(87) PCT Pub. No.: WO2018/213412
PCT Pub. Date: Nov. 22, 2018

(65) Prior Publication Data
US 2020/0199624 A1    Jun. 25, 2020

Related U.S. Application Data

(60) Provisional application No. 62/508,430, filed on May 19, 2017.

(51) Int. Cl.
*A61K 39/385* (2006.01)
*A61K 35/766* (2015.01)
(Continued)

(52) U.S. Cl.
CPC ............ *C12N 15/86* (2013.01); *A61K 35/766* (2013.01); *C07K 14/4702* (2013.01); *C12N 7/00* (2013.01);
(Continued)

(58) Field of Classification Search
None
See application file for complete search history.

(56) References Cited

U.S. PATENT DOCUMENTS 9,428,736 B2    8/2016   Russell et al.
2002/0132786 A1    9/2002   Alnemri
(Continued)

FOREIGN PATENT DOCUMENTS

CA    2857879 A1    12/2006
WO    WO-0216418 A2 *  2/2002   ......... C07K 14/4747
(Continued)

OTHER PUBLICATIONS

Kapp et al., "A Comprehensive Evaluation of the Activity and Selectivity Profile of Ligands for RGD-binding Integrins," Sci Rep Jan. 11:7:39805. Doi: 10.1038/srep39805 (Year: 2017).*
(Continued)

*Primary Examiner* — M Franco G Salvoza
(74) *Attorney, Agent, or Firm* — Thomas | Horstemeyer, LLP

(57) ABSTRACT

Recombinant viral vectors are disclosed that contain a nucleic acid encoding a Second Mitochondria-derived Activator of Caspases (Smac) protein inserted within an RNA virus genome, wherein the Smac protein specifically binds to at least a portion of an Inhibitor of Apoptosis Protein (IAP). Also disclosed are methods of treating cancer using the disclosed vectors.

10 Claims, 7 Drawing Sheets
Specification includes a Sequence Listing.

(51) Int. Cl.
  *C07K 14/47* (2006.01)
  *C12N 7/00* (2006.01)
  *C12N 15/86* (2006.01)
(52) U.S. Cl.
  CPC .............. *C12N 2310/141* (2013.01); *C12N 2760/20021* (2013.01); *C12N 2760/20032* (2013.01); *C12N 2760/20043* (2013.01)

(56) References Cited

U.S. PATENT DOCUMENTS

| | | | |
|---|---|---|---|
| 2004/0214783 A1* | 10/2004 | Terman | A61P 35/00 514/33 |
| 2005/0221489 A1 | 10/2005 | Garcia-Sastre et al. | |
| 2009/0175826 A1 | 7/2009 | Subbiah et al. | |
| 2009/0220458 A1 | 9/2009 | Schaffer et al. | |
| 2015/0306248 A1 | 10/2015 | Acharjee | |
| 2017/0037404 A1 | 2/2017 | Asuragen | |

FOREIGN PATENT DOCUMENTS

| | | | | |
|---|---|---|---|---|
| WO | WO-03086470 A2 * | 10/2003 | ............. | A61K 38/17 |
| WO | WO-2007033023 A2 * | 3/2007 | ......... | A61K 31/7105 |
| WO | WO-2011070440 A2 * | 6/2011 | ........... | A61K 35/766 |
| WO | WO-2015077714 A1 * | 5/2015 | ............. | A61K 35/12 |
| WO | 2015/154197 A1 | 10/2015 | | |
| WO | 2016079527 A1 | 5/2016 | | |
| WO | 2017143449 A1 | 8/2017 | | |

OTHER PUBLICATIONS

Rudikoff et al., "Single amino acid substitution altering antigen-binding specificity," Proc Natl Acad Sci USA 79:1979-1983 (Year: 1982).*
International Search Report issued for PCT/US2018/032915, mailed Aug. 1, 2018.
Sanjuan et al., Selection for Robustness in Mutagenized RNA Viruses, PLoS Genetics, vol. 3, Issue 6, pp. 939-946, 2007.
Marino et al., Self-consumption: the interplay of autophagy and apoptosis. Nat Rev Mol Cell Biol, 2014. 15(2): p. 81-94.
Lippai et al., Autophagy-from molecular mechanisms to clinical relevance. Cell Biol Toxicol, 2016.
Delaney et al., Haploinsufficiency networks identify targetable patterns of allelic deficiency in low mutation ovarian cancer. Nat Commun, 2017. 8: p. 14423.
Kandoth et al., Mutational landscape and significance across 12 major cancer types. Nature, 2013. 502(7471): p. 333-9.
Roy et al., Lycorine Downregulates HMGB1 to Inhibit Autophagy and Enhances Bortezomib Activity in Multiple Myeloma. Theranostics, 2016. 6(12): p. 2209-2224.
Tang et al., Endogenous HMGB1 regulates autophagy. J Cell Biol, 2010. 190(5): p. 881-92.
Liu et al., Role of Autophagy and Apoptosis in Non-Small-Cell Lung Cancer. Int J Mol Sci, 2017. 18(2).
Kulikov et al., Mitophagy: Link to cancer development and therapy. Biochem Biophys Res Commun, 2017. 482(3): p. 432-439.
Youle et al., Mechanisms of mitophagy. Nat Rev Mol Cell Biol, 2011. 12(1): p. 9-14.
Jang et al., Targeting AMPK-ULK1-mediated autophagy for combating BET inhibitor resistance in acute myeloid leukemia stem cells. Autophagy, 2017: p. 761-762.
Jang et al., AMPK-ULK1-mediated autophagy confers resistance to BET inhibitor JQ1 in acute myeloid leukemia stem cells. Clin Cancer Res, 2016.
Yao et al., An autophagy inhibitor enhances the inhibition of cell proliferation induced by a proteasome inhibitor in MCF-7 cells. Mol Med Rep, 2012. 5(1): p. 84-8.
Malilas et al., Suppression of autophagic genes sensitizes CUG2-overexpressing A549 human lung cancer cells to oncolytic vesicular stomatitis virus-induced apoptosis. Int J Oncol, 2014. 44(4): p. 1177-84.

Pearce et al., Vesicular stomatitis virus induces apoptosis primarily through Bak rather than Bax by inactivating Mcl-1 and Bcl-XL. J Virol, 2009. 83(18): p. 9102-12.
Balachandran et al., Alpha/beta interferons potentiate virus-induced apoptosis through activation of the FADD/Caspase-8 death signaling pathway. J Virol, 2000. 74(3): p. 1513-23.
Kopecky et al., Contrasting effects of matrix protein on apoptosis in HeLa and BHK cells infected with vesicular stomatitis virus are due to inhibition of host gene expression. J Virol, 2003. 77(8): p. 4658-69.
Lee et al., Molecular cloning and functional analysis of a novel oncogene, cancer-upregulated gene 2 (CUG2). Biochem Biophys Res Commun, 2007. 360(3): p. 633-9.
Malilas et al., Cancer upregulated gene 2, a novel oncogene, confers resistance to oncolytic vesicular stomatitis virus through STAT1-OASL2 signaling. Cancer Gene Ther, 2013. 20(2): p. 125-32.
Hu et al., Oncolytic newcastle disease virus triggers cell death of lung cancer spheroids and is enhanced by pharmacological inhibition of autophagy. Am J Cancer Res, 2015. 5(12): p. 3612-23.
Jiang et al., Pharmacological modulation of autophagy enhances Newcastle disease virus-mediated oncolysis in drug-resistant lung cancer cells. BMC Cancer, 2014. 14: p. 551.
Meng et al., Mitophagy promotes replication of oncolytic Newcastle disease virus by blocking intrinsic apoptosis in lung cancer cells. Oncotarget, 2014. 5(15): p. 6365-74.
Chakrabarti et al., RNase L triggers autophagy in response to viral infections. J Virol, 2012. 86(20): p. 11311-21.
Richetta et al., Sustained autophagy contributes to measles virus infectivity. PLoS Pathog, 2013. 9(9): p. e1003599.
Obuchi et al., Development of recombinant vesicular stomatitis viruses that exploit defects in host defense to augment specific oncolytic activity. J Virol, 2003. 77(16): p. 8843-56.
Willmon et al., Expression of IFN-beta enhances both efficacy and safety of oncolytic vesicular stomatitis virus for therapy of mesothelioma. Cancer Res, 2009. 69(19): p. 7713-20.
Saloura et al., Evaluation of an attenuated vesicular stomatitis virus vector expressing interferon-beta for use in malignant pleural mesothelioma: heterogeneity in interferon responsiveness defines potential efficacy. Hum Gene Ther, 2010. 21(1): p. 51-64.
Kurisetty et al., Preclinical safety and activity of recombinant VSV-IFN-beta in an immunocompetent model of squamous cell carcinoma of the head and neck. Head Neck, 2014. 36(11): p. 1619-27.
Patel et al., Vesicular stomatitis virus expressing interferon-beta is oncolytic and promotes antitumor immune responses in a syngeneic murine model of non-small cell lung cancer. Oncotarget, 2015. 6(32): p. 33165-77.
Goel et al., Radioiodide imaging and radiovirotherapy of multiple myeloma using VSV(Delta51)-NIS, an attenuated vesicular stomatitis virus encoding the sodium iodide symporter gene. Blood, 2007. 110(7): p. 2342-50.
Bourgeois-Daigneault et al., Oncolytic vesicular stomatitis virus expressing interferon-gamma has enhanced therapeutic activity. Mol Ther Oncolytics, 2016. 3: p. 16001.
Fandy et al., Smac/DIABLO enhances the therapeutic potential of chemotherapeutic drugs and irradiation, and sensitizes TRAIL-resistant breast cancer cells. Mol Cancer, 2008. 7: p. 60.
Houghton et al., Initial testing (stage 1) of LCL161, a SMAC mimetic, by the Pediatric Preclinical Testing Program. Pediatr Blood Cancer, 2012. 58(4): p. 636-9.
Dobson et al., Oncolytic virus synergizes with Smac mimetic compounds to induce rhabdomyosarcoma cell death in a syngeneic murine model. Oncotarget, 2017. 8(2): p. 3495-3508.
Ball et al., Phenotypic consequences of rearranging the P, M, and G genes of vesicular stomatitis virus. J Virol, 1999. 73(6): p. 4705-12.
Wertz et al., Gene rearrangement attenuates expression and lethality of a nonsegmented negative strand RNA virus. Proc Natl Acad Sci U S A, 1998. 95(7): p. 3501-6.
Samuel et al., BCL-2 inhibitors sensitize therapy-resistant chronic lymphocytic leukemia cells to VSV oncolysis. Mol Ther, 2013. 21(7): p. 1413-23.

(56) References Cited

OTHER PUBLICATIONS

Shulak et al., Histone deacetylase inhibitors potentiate vesicular stomatitis virus oncolysis in prostate cancer cells by modulating NF-kappaB-dependent autophagy. J Virol, 2014. 88(5): p. 2927-40.
Whelan et al., Efficient recovery of infectious vesicular stomatitis virus entirely from cDNA clones. Proc Natl Acad Sci U S A, 1995. 92(18): p. 8388-92.
Foster et al., Targeting inhibitor of apoptosis proteins in combination with ErbB antagonists in breast cancer. Breast Cancer Res, 2009. 11(3): p. R41.
Office Action issued by Chinese Patent Office, China Patent Application No. 201880032491.4, issued Feb. 24, 2023.
Ammayappan, Arun, et al., "Characteristics of Oncolytic Vesicular Stomatitis Virus Displaying Tumor-Targeting Ligands," Journal of Virology, vol. 87, No. 24 (2013), pp. 13543-13555.
Tang, Sijia, et al., "Modulation of the tumor microenvironment by armed vesicular stomatitis virus in a syngeneic pancreatic cancer model," Virology Journal, vol. 19, No. 1 (2022) (13 pgs.).
Office Action, issued European Patent Office, EP App. 18801713.1, issued Feb. 6, 2025.

* cited by examiner

SEQUENCE LISTING

```
<160> NUMBER OF SEQ ID NOS: 14

<210> SEQ ID NO 1
<211> LENGTH: 239
<212> TYPE: PRT
<213> ORGANISM: Homo sapiens

<400> SEQUENCE: 1

Met Ala Ala Leu Lys Ser Trp Leu Ser Arg Ser Val Thr Ser Phe Phe
1               5                   10                  15
```

Arg Tyr Arg Gln Cys Leu Cys Val Pro Val Ala Asn Phe Lys Lys
                20                  25                  30

Arg Cys Phe Ser Glu Leu Ile Arg Pro Trp His Lys Thr Val Thr Ile
            35                  40                  45

Gly Phe Gly Val Thr Leu Cys Ala Val Pro Ile Ala Gln Lys Ser Glu
50                  55                  60

Pro His Ser Leu Ser Ser Glu Ala Leu Met Arg Arg Ala Val Ser Leu
65                  70                  75                  80

Val Thr Asp Ser Thr Ser Thr Phe Leu Ser Gln Thr Thr Tyr Ala Leu
                85                  90                  95

Ile Glu Ala Ile Thr Glu Tyr Thr Lys Ala Val Tyr Thr Leu Thr Ser
            100                 105                 110

Leu Tyr Arg Gln Tyr Thr Ser Leu Leu Gly Lys Met Asn Ser Glu Glu
        115                 120                 125

Glu Asp Glu Val Trp Gln Val Ile Ile Gly Ala Arg Ala Glu Met Thr
130                 135                 140

Ser Lys His Gln Glu Tyr Leu Lys Leu Glu Thr Thr Trp Met Thr Ala
145                 150                 155                 160

Val Gly Leu Ser Glu Met Ala Ala Glu Ala Ala Tyr Gln Thr Gly Ala
                165                 170                 175

Asp Gln Ala Ser Ile Thr Ala Arg Asn His Ile Gln Leu Val Lys Leu
            180                 185                 190

Gln Val Glu Glu Val His Gln Leu Ser Arg Lys Ala Glu Thr Lys Leu
        195                 200                 205

Ala Glu Ala Gln Ile Glu Glu Leu Arg Gln Lys Thr Gln Glu Glu Gly
    210                 215                 220

Glu Glu Arg Ala Glu Ser Glu Gln Glu Ala Tyr Leu Arg Glu Asp
225                 230                 235

<210> SEQ ID NO 2
<211> LENGTH: 184
<212> TYPE: PRT
<213> ORGANISM: Artificial Sequence
<220> FEATURE:
<223> OTHER INFORMATION: Synthetic Construct

<400> SEQUENCE: 2

Ala Val Pro Ile Ala Gln Lys Ser Glu Pro His Ser Leu Ser Ser Glu
1               5                   10                  15

Ala Leu Met Arg Arg Ala Val Ser Leu Val Thr Asp Ser Thr Ser Thr
            20                  25                  30

Phe Leu Ser Gln Thr Thr Tyr Ala Leu Ile Glu Ala Ile Thr Glu Tyr
        35                  40                  45

Thr Lys Ala Val Tyr Thr Leu Thr Ser Leu Tyr Arg Gln Tyr Thr Ser
    50                  55                  60

Leu Leu Gly Lys Met Asn Ser Glu Glu Glu Asp Glu Val Trp Gln Val
65                  70                  75                  80

Ile Ile Gly Ala Arg Ala Glu Met Thr Ser Lys His Gln Glu Tyr Leu
                85                  90                  95

Lys Leu Glu Thr Thr Trp Met Thr Ala Val Gly Leu Ser Glu Met Ala
            100                 105                 110

Ala Glu Ala Ala Tyr Gln Thr Gly Ala Asp Gln Ala Ser Ile Thr Ala
        115                 120                 125

Arg Asn His Ile Gln Leu Val Lys Leu Gln Val Glu Glu Val His Gln
    130                 135                 140

Leu Ser Arg Lys Ala Glu Thr Lys Leu Ala Glu Ala Gln Ile Glu Glu
145                 150                 155                 160

Leu Arg Gln Lys Thr Gln Glu Glu Gly Glu Glu Arg Ala Glu Ser Glu
            165                 170                 175

Gln Glu Ala Tyr Leu Arg Glu Asp
            180

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Val, Thr, or Ile
<220> FEATURE:
<221> NAME/KEY: MISC_FEATURE
<222> LOCATION: (3)..(3)
<223> OTHER INFORMATION: Xaa is Pro or Ala
<220> FEATURE:
<221> NAME/KEY: MISC_FEATURE
<222> LOCATION: (4)..(4)
<223> OTHER INFORMATION: Xaa is Gly, Ala, Val, Leu, Ile, Pro, Ser, Thr,
      Cys, Met, Asn, or Gln

<400> SEQUENCE: 3

Ala Xaa Xaa Xaa
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Construct

<400> SEQUENCE: 4

Gly Arg Gly Asp Ser
1               5

<210> SEQ ID NO 5
<211> LENGTH: 511
<212> TYPE: PRT
<213> ORGANISM: Homo Sapiens

<400> SEQUENCE: 5

Met Lys Cys Leu Leu Tyr Leu Ala Phe Leu Phe Ile Gly Val Asn Cys
1               5                   10                  15

Lys Phe Thr Ile Val Phe Pro His Asn Arg Lys Gly Asn Trp Lys Asn
            20                  25                  30

Val Pro Ser Asn Tyr His Tyr Cys Pro Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Glu Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln

```
                115                 120                 125
Ser Cys Gly Tyr Ala Thr Val Thr Asp Ala Glu Ala Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
            165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Glu Gly Thr Gly Phe Arg Ser Asn
210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
            245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
            325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
            355                 360                 365

Glu Arg Glu Leu Trp Asp Asp Trp Ala Pro Tyr Glu Asp Val Glu Ile
370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
            405                 410                 415

Lys Ala Gln Val Phe Glu His Pro His Ile Gln Asp Ala Ala Ser Gln
            420                 425                 430

Leu Pro Asp Asp Glu Thr Leu Phe Phe Gly Asp Thr Gly Leu Ser Lys
            435                 440                 445

Asn Pro Ile Glu Phe Val Glu Gly Trp Phe Ser Ser Trp Lys Ser Ser
450                 455                 460

Ile Ala Ser Phe Cys Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
            485                 490                 495

Lys Arg Gln Ile Tyr Thr Asp Ile Glu Met Asn Arg Leu Gly Lys
            500                 505                 510

<210> SEQ ID NO 6
<211> LENGTH: 516
<212> TYPE: PRT
<213> ORGANISM: Artificial Sequence
```

<220> FEATURE:
<223> OTHER INFORMATION: Synthetic Construct

<400> SEQUENCE: 6

```
Met Lys Cys Leu Leu Tyr Leu Ala Phe Leu Phe Ile Gly Val Asn Cys
1               5                   10                  15

Lys Phe Thr Ile Val Phe Pro His Asn Arg Lys Gly Asn Trp Lys Asn
            20                  25                  30

Val Pro Ser Asn Tyr His Tyr Cys Pro Ser Ser Asp Leu Asn Trp
        35                  40                  45

His Asn Asp Leu Ile Gly Thr Ala Leu Gln Val Lys Met Pro Lys Ser
65  50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Glu Tyr Ile Thr His
                85                  90                  95

Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Arg
            180                 185                 190

Gly Asp Ser Gly Leu Cys Asp Ser Asn Leu Ile Ser Met Asp Ile Thr
                195                 200                 205

Phe Phe Ser Glu Asp Gly Glu Leu Ser Ser Leu Gly Lys Glu Gly Thr
210                 215                 220

Gly Phe Arg Ser Asn Tyr Phe Ala Tyr Glu Thr Gly Asp Lys Ala Cys
225                 230                 235                 240

Lys Met Gln Tyr Cys Lys His Trp Gly Val Arg Leu Pro Ser Gly Val
                245                 250                 255

Trp Phe Glu Met Ala Asp Lys Asp Leu Phe Ala Ala Arg Phe Pro
                260                 265                 270

Glu Cys Pro Glu Gly Ser Ser Ile Ser Ala Pro Ser Gln Thr Ser Val
            275                 280                 285

Asp Val Ser Leu Ile Gln Asp Val Glu Arg Ile Leu Asp Tyr Ser Leu
290                 295                 300

Cys Gln Glu Thr Trp Ser Lys Ile Arg Ala Gly Leu Pro Ile Ser Pro
305                 310                 315                 320

Val Asp Leu Ser Tyr Leu Ala Pro Lys Asn Pro Gly Thr Gly Pro Val
                325                 330                 335

Phe Thr Ile Ile Asn Gly Thr Leu Lys Tyr Phe Glu Thr Arg Tyr Ile
                340                 345                 350

Arg Val Asp Ile Ala Ala Pro Ile Leu Ser Arg Met Val Gly Met Ile
            355                 360                 365

Ser Gly Thr Thr Thr Glu Arg Glu Leu Trp Asp Asp Trp Ala Pro Tyr
        370                 375                 380

Glu Asp Val Glu Ile Gly Pro Asn Gly Val Leu Arg Thr Ser Ser Gly
385                 390                 395                 400
```

```
Tyr Lys Phe Pro Leu Tyr Met Ile Gly His Gly Met Leu Asp Ser Asp
                405                 410                 415

Leu His Leu Ser Ser Lys Ala Gln Val Phe Glu His Pro His Ile Gln
            420                 425                 430

Asp Ala Ala Ser Gln Leu Pro Asp Asp Glu Thr Leu Phe Phe Gly Asp
                435                 440                 445

Thr Gly Leu Ser Lys Asn Pro Ile Glu Phe Val Glu Gly Trp Phe Ser
        450                 455                 460

Ser Trp Lys Ser Ser Ile Ala Ser Phe Cys Phe Ile Ile Gly Leu Ile
465                 470                 475                 480

Ile Gly Leu Phe Leu Val Leu Arg Val Gly Ile Tyr Leu Cys Ile Lys
                485                 490                 495

Leu Lys His Thr Lys Lys Arg Gln Ile Tyr Thr Asp Ile Glu Met Asn
                500                 505                 510

Arg Leu Gly Lys
        515

<210> SEQ ID NO 7
<211> LENGTH: 65
<212> TYPE: DNA
<213> ORGANISM: Artificial Sequence
<220> FEATURE:
<223> OTHER INFORMATION: Synthetic Construct

<400> SEQUENCE: 7
ctgttaatgc taatcgtgat aggggttttt gcctccaact gactcctaca tattagcatt    60
aacag                                                                65

<210> SEQ ID NO 8
<211> LENGTH: 11934
<212> TYPE: DNA
<213> ORGANISM: Artificial Sequence
<220> FEATURE:
<223> OTHER INFORMATION: Synthetic Construct

<400> SEQUENCE: 8
acgaagacaa acaaaccatt attatcatta aaaggctcag gagaaacttt aacagtaatc    60
aaaatgtctg ttacagtcaa gagaatcatt gacaacacag tcatagttcc aaaacttcct   120
gcaaatgagg atccagtgga atacccggca gattacttca gaaaatcaaa ggagattcct   180
ctttacatca atactacaaa aagtttgtca gatctaagag atatgtctca ccaaggcctc   240
aaatccggaa atgtatcaat catacatgtc aacagctact gtatggagc attaaaggac   300 atccggggta agttggataa agattggtca agtttcggaa taaacatcgg aaagcaggg   360 gatacaatcg gaatatttga ccttgtatcc ttgaaagccc tggacggcgt acttccagat   420
ggagtatcgg atgcttccag aaccagcgca gatgacaaat ggttgccttt gtatctactt   480
ggcttataca gagtgggcag aacacaaatg cctgaataca gaaaaaagct catggatggg   540
ctgacaaatc aatgcaaaat gatcaatgaa cagtttgaac ctcttgtgcc agaaggtcgt   600
gacatttttg atgtgtgggg aaatgacagt aattacacaa aaattgtcgc tgcagtggac   660
atgttcttcc acatgttcaa aaaacatgaa tgtgcctcgt tcagatacgg aactattgtt   720
tccagattca aagattgtgc tgcattggca acatttggac acctctgcaa ataaccgga   780 atgtctacag aagatgtaac gacctggatc ttgaaccgag aagttgcaga tgaaatggtc   840
caaatgatgc ttccaggcca agaaattgac aaggccgatt catacatgcc ttatttgatc   900
```

```
gactttggat tgtcttctaa gtctccatat tcttccgtca aaaccctgc  cttccacttc    960
tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata acaaatacac tccagatgat   1140
agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg caagtatgc  taagtcagaa   1320
tttgacaaat gacctataa  ttctcagatc acctattata tattatgcta catatgaaaa   1380
aaactaacag atatcatgga taatctcaca aaagttcgtg agtatctcaa gtcctactct   1440
cgtctagatc aggcggtagg agagatagat gagatcgaag cacaacgagc tgaaaagtcc   1500
aattatgagt tgttccaaga ggacggagtg gaagagcata ctaggccctc ttattttcag   1560
gcagcagatt attctgacac agaatctgaa ccagaaattg aagacaatca aggcttgtat   1620
gtaccagatc cggaagctga gcaagttgaa ggctttatac aggggccttt agatgactat   1680
gcagatgagg acgtggatgt tgtattcact tcggactgga acagcctga  gcttgaatcc   1740
gacgagcatg aaagacctt  acggttgaca ttgccgagg  gtttaagtgg agagcagaaa   1800
tcccagtggc ttttgacgat taaagcagtc gttcaaagtg ccaaacactg gaatctggca   1860
gagtgcacat ttgaagcatc gggagaaggg gtcatcataa aaaagcgcca gataactccg   1920
gatgtatata aggtcactcc agtgatgaac acacatccgt accaatcaga agccgtatca   1980
gatgtttggt ctctctcaaa gacatccatg actttccaac ccaagaaagc aagtcttcag   2040
cctctcacca tatccttgga tgaattgttc tcatctagag gagaattcat ctctgtcgga   2100
ggtaacggac gaatgtctca taaagaggcc atcctgctcg gtctgaggta caaaaagttg   2160
tacaatcagg cgagagtcaa atattctctg tagactatga aaaaaagtaa cagatatcac   2220
aatctaagtg ttatcccaat ccattcatca tgagttcctt aaagaagatt ctcggtctga   2280
aggggaaagg taagaaatct aagaaattag ggatcgcacc acccccttat gaagaggaca   2340
ctagcatgga gtatgctccg agcgctccaa ttgacaaatc ctattttgga gttgacgaga   2400
tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccctt ctacaaaatc ttggcttttt   2580
tgggttcttc taatctaaag gccactccag cggtattggc agatcaaggt caaccagagt   2640
atcacgctca ctgcgaaggc agggcttatt tgccacatag gatggggaag accctccca   2700
tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
ttgtcgagaa aaaggcatct ggagcgtggg tcctggattc tatcagccac ttcaaatgag   2940
ctagtctagc ttccagcttc tgaacaatcc ccggtttact cagtctctcc taattccagc   3000
ctttcgaaca actaatatcc tgtcttttct atccctatga aaaaactaa  cagatctcga   3060
gatggcggct ctgaagagtt ggctgtcgcg cagcgtaact tcattcttca ggtacagaca   3120
gtgtttgtgt gttcctgttg tggctaactt taagaagcgg tgtttctcag aattgataag   3180
accatggcac aaaactgtga cgattggctt tggagtaacc ctgtgtgcgg ttcctattgc   3240
acagaaatca gagcctcatt cccttagtag tgaagcattg atgaggagag cagtgtcttt   3300
```

```
ggtaacagat agcacctcta cctttctctc tcagaccaca tatgcgttga ttgaagctat   3360
tactgaatat actaaggctg tttataccct aacttctctt taccgacaat atacaagttt   3420
acttgggaaa atgaattcag aggaggaaga tgaagtgtgg caggtgatca taggagccag   3480
agctgagatg acttcaaaac accaagagta cttgaagctg gaaaccactt ggatgactgc   3540
agttggtctt tcagagatgg cagcagaagc tgcatatcaa actggcgcag atcaggcctc   3600
tataaccgcc aggaatcaca ttcagctggt gaaactgcag gtggaagagg tgcaccagct   3660
ctcccggaaa gcagaaacca agctggcaga agcacagata gaagagctcc gtcagaaaac   3720
acaggaggaa ggggaggagc gggctgagtc ggagcaggag gcctacctgc gtgaggattg   3780
actcgagtat atttttaattt ttaattttta tgaaaaaaac taacagagat cgatctgttt   3840
ccttgacacc atgaagtgcc ttttgtactt agctttttta ttcatcgggg tgaattgcaa   3900
gttcaccata gttttccac acaaccgaaa aggaaactgg aaaaatgttc cttccaatta   3960
ccattattgc ccgtcaagct cagatttaaa ttggcataat gacttaatag gcacagcctt   4020
acaagtcaaa atgcccaaga gtcacaaggc tattcaagca gacggttgga tgtgtcatgc   4080
ttccaaatgg gtcactactt gtgatttccg ctggtacgga ccggagtata taacacattc   4140
catccgatcc ttcactccat ctgtagaaca atgcaaggaa agcattgaac aaacgaaaca   4200
aggaacttgg ctgaatccag gcttccctcc tcaaagttgt ggatatgcaa ctgtgacgga   4260
tgctgaagca gcgattgtcc aggtgactcc tcaccatgtg cttgttgatg aatacacagg   4320
agaatgggtt gattcacagt tcatcaacgg aaaatgcagc aatgacatat gccccactgt   4380
ccataactcc acaacctggc attccgacta taaggtcaaa gggctatgtg attctaacct   4440
catttccatg gacatcacct tcttctcaga ggacggagag ctatcatccc taggaaagga   4500
gggcacaggg ttcagaagta actactttgc ttatgaaact ggagacaagg cctgcaaaat   4560
gcagtactgc aagcattggg gagtcagact cccatcaggt gtctggttcg agatggctga   4620
taaggatctc tttgctgcag ccagattccc tgaatgccca aagggtcaa gtatctctgc   4680 tccatctcag acctcagtgg atgtaagtct cattcaggac gttgagagga tcttggatta   4740
ttccctctgc caagaaacct ggagcaaaat cagagcgggt cttcccatct ctccagtgga   4800
tctcagctat cttgctccta aaaacccagg aaccggtcct gtcttaacca taatcaatgg   4860
taccctaaaa tactttgaga ccagatacat cagagtcgat attgctgctc caatcctctc   4920
aagaatggtc ggaatgatca gtggaactac cacagaaagg gaactgtggg atgactgggc   4980
tccatatgaa gacgtggaaa ttggacccaa tggagttctg aggaccagtt caggatataa   5040 gtttcccttta tatatgattg gacatggtat gttggactcc gatcttcatc ttagctcaaa   5100
ggctcaggtg tttgaacatc ctcacattca agacgctgct tcgcagcttc ctgatgatga   5160
gactttattt tttggtgata ctgggctatc caaaaatcca atcgagtttg tagaaggttg   5220
gttcagtagt tggaagagct ctattgcctc ttttttgcttt atcatagggt taatcattgg   5280
actattcttg gttctccgag ttggtattta tctttgcatt aaattaaagc acaccaagaa   5340
aagacagatt tatacagaca tagagatgaa ccgacttgga agtaactca aatcctgcac   5400 aacagattct tcatgtttga accaaatcaa cttgtgtatat catgctcaaa gaggccttaa   5460
ttatatttta attttaatt tttatgaaaa aaactaacag caatcatgga agtccacgat   5520
tttgagaccg acgagttcaa tgatttcaat gaagatgact atgccacaag agaattcctg   5580
aatcccgatg agcgcatgac gtacttgaat catgctgatt acaatttgaa ttctcctcta   5640
```

```
attagtgatg atattgacaa tttgatcagg aaattcaatt ctcttccgat tccctcgatg   5700
tgggatagta agaactggga tggagttctt gagatgttaa catcatgtca agccaatccc   5760
atctcaacat ctcagatgca taaatggatg ggaagttggt taatgtctga taatcatgat   5820
gccagtcaag ggtatagttt tttacatgaa gtggacaaag aggcagaaat aacatttgac   5880
gtggtggaga ccttcatccg cggctgggc aacaaaccaa ttgaatacat caaaaaggaa   5940
agatggactg actcattcaa aattctcgct tatttgtgtc aaaagttttt ggacttacac   6000
aagttgacat taatcttaaa tgctgtctct gaggtggaat tgctcaactt ggcgaggact   6060
ttcaaaggca aagtcagaag aagttctcat ggaacgaaca tatgcaggat tagggttccc   6120
agcttgggtc ctacttttat ttcagaagga tgggcttact tcaagaaact tgatattcta   6180
atggaccgaa actttctgtt aatggtcaaa gatgtgatta tagggaggat gcaaacggtg   6240
ctatccatgg tatgtagaat agacaacctg ttctcagagc aagacatctt ctcccttcta   6300
aatatctaca gaattggaga taaaattgtg gagaggcagg gaaattttc ttatgacttg   6360 attaaaatgg tggaaccgat atgcaacttg aagctgatga aattagcaag agaatcaagg   6420
cctttagtcc cacaattccc tcattttgaa aatcatatca agacttctgt tgatgaaggg   6480
gcaaaaattg accgaggtat aagattcctc catgatcaga taatgagtgt gaaaacagtg   6540
gatctcacac tggtgattta tggatcgttc agacattggg gtcatccttt tatagattat   6600
tacactggac tagaaaaatt acattcccaa gtaaccatga agaaagatat tgatgtgtca   6660
tatgcaaaag cacttgcaag tgatttagct cggattgttc tatttcaaca gttcaatgat   6720
cataaaaagt ggttcgtgaa tggagacttg ctccctcatg atcatccctt taaaagtcat   6780
gttaaagaaa atacatggcc cacagctgct caagttcaag attttggaga taatggcat   6840 gaacttccgc tgattaaatg ttttgaaata cccgacttac tagacccatc gataatatac   6900
tctgacaaaa gtcattcaat gataggtca gaggtgttga acatgtccg aatgaatccg   6960 aacactccta tccctagtaa aaaggtgttg cagactatgt tggacacaaa ggctaccaat   7020
tggaaagaat ttcttaaaga gattgatgag aagggcttag atgatgatga tctaattatt   7080
ggtcttaaag gaaaggagag ggaactgaag ttggcaggta gattttctc cctaatgtct   7140 tggaaattgc gagaatactt tgtaattacc gaatatttga taaagactca tttcgtccct   7200
atgtttaaag gcctgacaat ggcggacgat ctaactgcag tcattaaaaa gatgttagat   7260
tcctcatccg gccaaggatt gaagtcatat gaggcaattt gcatagccaa tcacattgat   7320
tacgaaaaat ggaataacca ccaaaggaag ttatcaaacg gcccagtgtt ccgagttatg   7380
ggccagttct taggttatcc atccttaatc gagagaactc atgaattttt tgagaaaagt   7440
cttatatact acaatggaag accagacttg atgcgtgttc acaacaacac actgatcaat   7500
tcaacctccc aacgagtttg ttggcaagga caagagggtg gactggaagg tctacggcaa   7560
aaaggatgga gtatcctcaa tctactggtt attcaaagag aggctaaaat cagaaacact   7620
gctgtcaaag tcttggcaca aggtgataat caagttattt gcacacagta taaaacgaag   7680
aaatcgagaa acgttgtaga attacagggt gctctcaatc aaatggtttc taataatgag   7740
aaaattatga ctgcaatcaa aataggaca gggaagttag acttttgat aaatgacgat   7800 gagactatgc aatctgcaga ttacttgaat tatggaaaaa taccgatttt ccgtggagtg   7860
attagagggt tagagaccaa gagatggtca cgagtgactt gtgtcaccaa tgaccaaata   7920
cccacttgtg ctaatataat gagctcagtt tccacaaatg ctctcaccgt agctcatttt   7980
gctgagaacc caatcaatgc catgatacag tacaattatt ttgggacatt tgctagactc   8040
```

```
ttgttgatga tgcatgatcc tgctcttcgt caatcattgt atgaagttca agataagata   8100
ccgggcttgc acagttctac tttcaaatac gccatgttgt atttggaccc ttccattgga   8160
ggagtgtcgg gcatgtcttt gtccaggttt ttgattagag ccttcccaga tcccgtaaca   8220
gaaagtctct cattctggag attcatccat gtacatgctc gaagtgagca tctgaaggag   8280
atgagtgcag tatttggaaa ccccgagata gccaagtttc gaataactca catagacaag   8340
ctagtagaag atccaacctc tctgaacatc gctatgggaa tgagtccagc gaacttgtta   8400
aagactgagg ttaaaaaatg cttaatcgaa tcaagacaaa ccatcaggaa ccaggtgatt   8460
aaggatgcaa ccatatattt gtatcatgaa gaggatcggc tcagaagttt cttatggtca   8520
ataaatcctc tgttccctag atttttaagt gaattcaaat caggcacttt tttgggagtc   8580
gcagacgggc tcatcagtct atttcaaaat tctcgtacta ttcggaactc ctttaagaaa   8640
aagtatcata gggaattgga tgatttgatt gtgaggagtg aggtatcctc tttgacacat   8700
ttagggaaac ttcatttgag aaggggatca tgtaaaatgt ggacatgttc agctactcat   8760
gctgacacat taagatacaa atcctggggc cgtacagtta ttgggacaac tgtacccat   8820 ccattagaaa tgttgggtcc acaacatcga aaagagactc cttgtgcacc atgtaacaca   8880
tcagggttca attatgtttc tgtgcattgt ccagacggga tccatgacgt ctttagttca   8940
cggggaccat tgcctgctta tctagggtct aaaacatctg aatctacatc tattttgcag   9000
ccttgggaaa gggaaagcaa agtcccactg attaaaagag ctacacgtct tagagatgct   9060
atctcttggt ttgttgaacc cgactctaaa ctagcaatga ctatactttc taacatccac   9120
tctttaacag gcgaagaatg gaccaaaagg cagcatgggt tcaaaagaac agggtctgcc   9180
cttcataggt tttcgacatc tcggatgagc catggtgggt tcgcatctca gagcactgca   9240
gcattgacca ggttgatggc aactacagac accatgaggg atctgggaga tcagaatttc   9300
gactttttat tccaagcaac gttgctctat gctcaaatta ccaccactgt tgcaagagac   9360
ggatggatca ccagttgtac agatcattat catattgcct gtaagtcctg tttgagaccc   9420
atagaagaga tcaccctgga ctcaagtatg gactacacgc cccagatgt atcccatgtg   9480 ctgaagacat ggaggaatgg ggaaggttcg tggggacaag agataaaaca gatctatcct   9540
ttagaaggga attggaagaa tttagcacct gctgagcaat cctatcaagt cggcagatgt   9600
ataggttttc tatatggaga cttggcgtat agaaaatcta ctcatgccga ggacagttct   9660
ctatttcctc tatctataca aggtcgtatt agaggtcgag gtttcttaaa agggttgcta   9720
gacggattaa tgagagcaag ttgctgccaa gtaatacacc ggagaagtct ggctcatttg   9780
aagaggccgg ccaacgcagt gtacggaggt ttgatttact tgattgataa attgagtgta   9840
tcacctccat tcctttctct tactagatca ggacctatta gagacgaatt agaaacgatt   9900
ccccacaaga tcccaaccte ctatccgaca agcaaccgtg atatgggggt gattgtcaga   9960
aattacttca ataccaatg ccgtctaatt gaaaagggaa aatacagatc acattattca  10020
caattatggt tattctcaga tgtcttatcc atagacttca ttggaccatt ctctatttcc  10080
accaccctct tgcaaatcct atacaagcca ttttatcctg ggaaagataa gaatgagttg  10140
agagagctgg caaatctttc ttcattgcta agatcaggag aggggtggga agacatacat  10200
gtgaaattct tcaccaagga catattattg tgtccagagg aaatcagaca tgcttgcaag  10260
ttcgggattg ctaaggataa taataaagac atgagctatc cccttgggg aagggaatcc  10320 agagggacaa ttacaacaat ccctgtttat tatacgacca cccccttaccc aaagatgcta  10380
```

```
gagatgcctc caagaatcca aaatcccctg ctgtccggaa tcaggttggg ccaattacca    10440
actggcgctc attataaaat tcggagtata ttacatggaa tgggaatcca ttacagggac    10500
ttcttgagtt gtggagacgg ctccggaggg atgactgctg cattactacg agaaaatgtg    10560
catagcagag gaatattcaa tagtctgtta gaattatcag ggtcagtcat gcgaggcgcc    10620
tctcctgagc cccccagtgc cctagaaact taggaggag ataaatcgag atgtgtaaat    10680
ggtgaaacat gttgggaata tccatctgac ttatgtgacc caaggacttg ggactatttc    10740
ctccgactca aagcaggctt ggggcttcaa attgatttaa ttgtaatgga tatggaagtt    10800
cgggattctt ctactagcct gaaaattgag acgaatgtta gaaattatgt gcaccggatt    10860
ttggatgagc aaggagtttt aatctacaag acttatggaa catatatttg tgagagcgaa    10920
aagaatgcag taacaatcct tggtcccatg ttcaagacgg tcgacttagt tcaaacagaa    10980
tttagtagtt ctcaaacgtc tgaagtatat atggtatgta aggtttgaa gaaattaatc    11040 gatgaaccca tcccgattg gtcttccatc aatgaatcct ggaaaaacct gtacgcattc    11100
cagtcatcag aacaggaatt tgccagagca agaaggtta gtacatactt taccttgaca    11160
ggtattccct cccaattcat tcctgatcct tttgtaaaca ttgagactat gctacaaata    11220
ttcggagtac ccacgggtgt gtctcatgcg gctgccttaa aatcatctga tagacctgca    11280
gatttattga ccattagcct tttttatatg gcgattatat cgtattataa catcaatcat    11340
atcagagtag gaccgatacc tccgaacccc ccatcagatg gaattgcaca aaatgtgggg    11400
atcgctataa ctggtataag cttttggctg agtttgatgg agaaagacat tccactatat    11460
caacagtgtt tggcagttat ccagcaatca tttccgatta ggtgggaggc tatttcagta    11520
aaaggaggat acaagcagaa gtggagtact agaggtgatg ggctcccaaa agatacccga    11580
atttcagact ccttggcccc aatcgggaac tggatcagat ctttggaatt ggtccgaaac    11640
caagttcgtc taaatccatt caataagatc ttgttcaatc agctatgtcg tacagtggat    11700
aatcatttga gtggtcaaa tttgcgaaaa aacacaggaa tgattgaatg gatcaatggg    11760
cgaatttcaa aagaagaccg gtctatactg atgttgaaga gtgacctaca tgaggaaaac    11820
tcttggagag attaaaaaat caggaggaga ctccaaactt taagtatgaa aaaaactttg    11880
atccttaaga ccctcttgtg gttttttattt tttatctggt tttgtggtct tcgt           11934
```

<210> SEQ ID NO 9
<211> LENGTH: 11772
<212> TYPE: DNA
<213> ORGANISM: Artificial Sequence
<220> FEATURE:
<223> OTHER INFORMATION: Synthetic Construct

<400> SEQUENCE: 9

```
acgaagacaa acaaaccatt attatcatta aaaggctcag gagaaacttt aacagtaatc      60
aaaatgtctg ttacagtcaa gagaatcatt gacaacacag tcatagttcc aaaacttcct     120
gcaaatgagg atccagtgga ataccccggca gattacttca gaaaatcaaa ggagattcct     180
ctttacatca atactacaaa aagtttgtca gatctaagag gatatgtcta ccaaggcctc     240
aaatccggaa atgtatcaat catacatgtc aacagctact gtatggagc attaaaggac     300 atccggggta agttggataa agattggtca agtttcggaa taaacatcgg gaaagcaggg     360
gatacaatcg gaatatttga cctgtatcc ttgaaagccc tggacggcgt acttccagat     420
ggagtatcga tgcttccag aaccagcgca gatgacaaat ggttgccttt gtatctactt     480
ggcttataca gagtgggcag aacacaaatg cctgaataca gaaaaaagct catggatggg     540
```

```
ctgacaaatc aatgcaaaat gatcaatgaa cagtttgaac ctcttgtgcc agaaggtcgt    600
gacatttttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca aagattgtgc tgcattggca acatttggac acctctgcaa aataaccgga    780
atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaccctgc cttccacttc    960 tgggggcaat tgacagctct tctgctcaga tccaccagag caaggaatgc ccgacagcct   1020
gatgacattg agtatacatc tcttactaca gcaggtttgt tgtacgctta tgcagtagga   1080
tcctctgccg acttggcaca acagttttgt gttggagata caaatacac tccagatgat   1140 agtaccggag gattgacgac taatgcaccg ccacaaggca gagatgtggt cgaatggctc   1200
ggatggtttg aagatcaaaa cagaaaaccg actcctgata tgatgcagta tgcgaaaaga   1260
gcagtcatgt cactgcaagg cctaagagag aagacaattg caagtatgc taagtcagaa   1320 tttgacaaat gacccctataa ttctcagatc acctattata tattatgcta catatgaaaa   1380
aaactaacag atatcatgga taatctcaca aaagttcgtg agtatctcaa gtcctactct   1440
cgtctagatc aggcggtagg agagatagat gagatcgaag cacaacgagc tgaaaagtcc   1500
aattatgagt tgttccaaga ggacggagtg gaagagcata ctaggccctc ttatttttcag  1560 gcagcagatg attctgacac agaatctgaa ccagaaattg aagacaatca aggcttgtat   1620
gtaccagatc cggaagctga gcaagttgaa ggctttatac aggggccttt agatgactat   1680
gcagatgagg acgtggatgt tgtattcact tcggactgga acagcctga gcttgaatcc   1740 gacgagcatg gaaagacctt acggttgaca ttgccagagg gtttaagtgg agagcagaaa   1800
tcccagtggc ttttgacgat taaagcagtc gttcaaagtg ccaaacactg gaatctggca   1860
gagtgcacat ttgaagcatc gggagaaggg gtcatcataa aaaagcgcca gataactccg   1920
gatgtatata aggtcactcc agtgatgaac acacatccgt accaatcaga gccgtatca   1980 gatgtttggt ctctctcaaa gacatccatg actttccaac ccaagaaagc aagtcttcag   2040
cctctcacca tatccttgga tgaattgttc tcatctagag gagaattcat ctctgtcgga   2100
ggtaacggac gaatgtctca taaagaggcc atcctgctcg gtctgaggta caaaaagttg   2160
tacaatcagg cgagagtcaa atattctctg tagactatga aaaaagtaa cagatatcac   2220 aatctaagtg ttatcccaat ccattcatca tgagttcctt aaagaagatt ctcggtctga   2280
aggggaaagg taagaaatct aagaaattag ggatcgcacc acccccttat gaagaggaca   2340
ctagcatgga gtatgctccg agcgctccaa ttgacaaatc ctatttttgga gttgacgaga   2400 tggacaccta tgatccgaat caattaagat atgagaaatt cttctttaca gtgaaaatga   2460
cggttagatc taatcgtccg ttcagaacat actcagatgt ggcagccgct gtatcccatt   2520
gggatcacat gtacatcgga atggcaggga acgtcccctt ctacaaaatc ttggcttttt   2580
tgggttcttc taatctaaag gccactccag cggtattggc agatcaaggt caaccagagt   2640
atcacgctca ctgcgaaggc agggcttatt tgccacatag gatggggaag accctccca   2700 tgctcaatgt accagagcac ttcagaagac cattcaatat aggtctttac aagggaacga   2760
ttgagctcac aatgaccatc tacgatgatg agtcactgga agcagctcct atgatctggg   2820
atcatttcaa ttcttccaaa ttttctgatt tcagagagaa ggccttaatg tttggcctga   2880
```

```
ttgtcgagaa aaaggcatct ggagcgtggg tcctggattc tatcagccac ttcaaatgag    2940
ctagtctagc ttccagcttc tgaacaatcc ccggtttact cagtctctcc taattccagc    3000
ctttcgaaca actaatatcc tgtctttttct atccctatga aaaaaactaa cagatctcga   3060
gatggcggtt cctattgcac agaaatcaga gcctcattcc cttagtagtg aagcattgat    3120
gaggagagca gtgtctttgg taacagatag cacctctacc tttctctctc agaccacata    3180
tgcgttgatt gaagctatta ctgaatatac taaggctgtt tataccttaa cttctcttta    3240
ccgacaatat acaagtttac ttgggaaaat gaattcagag gaggaagatg aagtgtggca    3300
ggtgatcata ggagccagag ctgagatgac ttcaaaacac caagagtact tgaagctgga    3360
aaccacttgg atgactgcag ttggtctttc agagatggca gcagaagctg catatcaaac    3420
tggcgcagat caggcctcta taaccgccag gaatcacatt cagctggtga aactgcaggt    3480
ggaagaggtg caccagctct cccggaaagc agaaaccaag ctggcagaag cacagataga    3540
agagctccgt cagaaaacac aggaggaagg ggaggagcgg gctgagtcgg agcaggaggc    3600
ctacctgcgt gaggattgac tcgagtatat tttaatttttt aattttttatg aaaaaaacta  3660
acagagatcg atctgtttcc ttgacaccat gaagtgcctt ttgtacttag cttttttatt    3720
catcggggtg aattgcaagt tcaccatagt ttttccacac aaccgaaaag gaaactggaa    3780
aaatgttcct tccaattacc attattgccc gtcaagctca gatttaaatt ggcataatga    3840
cttaataggc acagccttac aagtcaaaat gcccaagagt cacaaggcta ttcaagcaga    3900
cggttggatg tgtcatgctt ccaaatgggt cactacttgt gatttccgct ggtacggacc    3960
ggagtatata acacattcca tccgatcctt cactccatct gtagaacaat gcaaggaaag    4020
cattgaacaa acgaaacaag gaacttggct gaatccaggc ttccctcctc aaagttgtgg    4080
atatgcaact gtgacggatg ctgaagcagc gattgtccag gtgactcctc accatgtgct    4140
tgttgatgaa tacacaggag aatgggttga ttcacagttc atcaacggaa aatgcagcaa    4200
tgacatatgc cccactgtcc ataactccac aacctggcat tccgactata ggtcaaaagg    4260
gctatgtgat tctaacctca tttccatgga catcaccttc ttctcagagg acggagagct    4320
atcatcccta ggaaaggagg gcacagggtt cagaagtaac tactttgctt atgaaactgg    4380
agacaaggcc tgcaaaatgc agtactgcaa gcattgggga gtcagactcc catcaggtgt    4440
ctggttcgag atggctgata aggatctctt tgctgcagcc agattccctg aatgcccaga    4500
agggtcaagt atctctgctc catctcagac ctcagtggat gtaagtctca ttcaggacgt    4560
tgagaggatc ttggattatt ccctctgcca agaaacctgg agcaaaatca gagcgggtct    4620
tcccatctct ccagtggatc tcagctatct tgctcctaaa aacccaggaa ccggtcctgt    4680
ctttaccata atcaatggta ccctaaaata ctttgagacc agatacatca gagtcgatat    4740
tgctgctcca atcctctcaa gaatggtcgg aatgatcagt ggaactacca cagaaaggga    4800
actgtgggat gactgggctc catatgaaga cgtggaaatt ggacccaatg gagttctgag    4860
gaccagttca ggatataagt ttcctttata tatgattgga catggtatgt tggactccga    4920
tcttcatctt agctcaaagg ctcaggtgtt tgaacatcct cacattcaag acgctgcttc    4980
gcagcttcct gatgatgaga ctttattttt tggtgatact gggctatcca aaaatccaat    5040
cgagtttgta gaaggttggt tcagtagttg aaagagctct attgcctctt tttgctttat    5100
catagggtta atcattggac tattcttggt tctccgagtt ggtatttatc tttgcattaa    5160
attaaagcac accaagaaaa gacagattta tacagacata gagatgaacc gacttggaaa    5220
gtaactcaaa tcctgcacaa cagattcttc atgtttgaac caaatcaact tgtgatatca    5280
```

```
tgctcaaaga ggccttaatt atattttaat ttttaatttt tatgaaaaaa actaacagca    5340
atcatggaag tccacgattt tgagaccgac gagttcaatg atttcaatga agatgactat    5400
gccacaagag aattcctgaa tcccgatgag cgcatgacgt acttgaatca tgctgattac    5460
aatttgaatt ctcctctaat tagtgatgat attgacaatt tgatcaggaa attcaattct    5520
cttccgattc cctcgatgtg ggatagtaag aactgggatg gagttcttga gatgttaaca    5580
tcatgtcaag ccaatcccat ctcaacatct cagatgcata aatggatggg aagttggtta    5640
atgtctgata atcatgatgc cagtcaaggg tatagttttt tacatgaagt ggacaaagag    5700
gcagaaataa catttgacgt ggtggagacc ttcatccgcg gctggggcaa caaaccaatt    5760
gaatacatca aaaaggaaag atggactgac tcattcaaaa ttctcgctta tttgtgtcaa    5820
aagttttggg acttacacaa gttgacatta atcttaaatg ctgtctctga ggtggaattg    5880
ctcaacttgg cgaggacttt caaaggcaaa gtcagaagaa gttctcatgg aacgaacata    5940
tgcaggatta gggttcccag cttgggtcct acttttattt cagaaggatg gcttacttc    6000 aagaaacttg atattctaat ggaccgaaac tttctgttaa tggtcaaaga tgtgattata    6060
gggaggatgc aaacggtgct atccatggta tgtagaatag acaacctgtt ctcagagcaa    6120
gacatcttct cccttctaaa tatctacaga attggagata aaattgtgga gaggcaggga    6180 aattttctt atgacttgat taaaatggtg gaaccgatat gcaacttgaa gctgatgaaa    6240
ttagcaagag aatcaaggcc tttagtccca caattccctc attttgaaaa tcatatcaag    6300
acttctgttg atgaaggggc aaaaattgac cgaggtataa gattcctcca tgatcagata    6360
atgagtgtga aaacagtgga tctcacactg gtgatttatg gatcgttcag acattggggt    6420 catccttta tagattatta cactggacta gaaaaattac attcccaagt aaccatgaag    6480
aaagatattg atgtgtcata tgcaaaagca cttgcaagtg atttagctcg gattgttcta    6540
tttcaacagt tcaatgatca taaaaagtgg ttcgtgaatg gagacttgct ccctcatgat    6600
catcccttta aaagtcatgt taaagaaaat acatggccca cagctgctca agttcaagat    6660
tttggagata aatggcatga acttccgctg attaaatgtt ttgaaatacc cgacttacta    6720
gacccatcga taatatactc tgacaaaagt cattcaatga ataggtcaga ggtgttgaaa    6780
catgtccgaa tgaatccgaa cactcctatc cctagtaaaa aggtgttgca gactatgttg    6840
gacacaaagg ctaccaattg gaaagaattt cttaaagaga ttgatgagaa gggcttagat    6900
gatgatgatc taattattgg tcttaaagga aggagaggg aactgaagtt ggcaggtaga    6960
tttttctccc taatgtcttg gaaattgcga gaatactttg taattaccga atatttgata    7020
aagactcatt tcgtccctat gtttaaaggc ctgacaatgg cggacgatct aactgcagtc    7080
attaaaaaga tgttagattc ctcatccggc caaggattga agtcatatga ggcaatttgc    7140
atagccaatc acattgatta cgaaaaatgg aataaccacc aaaggaagtt atcaaacggc    7200
ccagtgttcc gagttatggg ccagttctta ggttatccat ccttaatcga gagaactcat    7260
gaattttttg agaaaagtct tatatactac aatggaagac cagacttgat gcgtgttcac    7320
aacaacacac tgatcaattc aacctcccaa cgagtttgtt ggcaaggaca agagggtgga    7380
ctggaaggtc tacggcaaaa aggatggagt atcctcaatc tactggttat tcaaagagag    7440
gctaaaatca gaaacactgc tgtcaaagtc ttggcacaag gtgataatca agttatttgc    7500
acacagtata aaacgaagaa atcgagaaac gttgtagaat tacagggtgc tctcaatcaa    7560
atggtttcta ataatgagaa aattatgact gcaatcaaaa tagggacagg gaagttagga    7620
```

```
cttttgataa atgacgatga gactatgcaa tctgcagatt acttgaatta tggaaaaata   7680
ccgattttcc gtggagtgat tagagggtta gagaccaaga gatggtcacg agtgacttgt   7740
gtcaccaatg accaaatacc cacttgtgct aatataatga gctcagtttc cacaaatgct   7800
ctcaccgtag ctcattttgc tgagaaccca atcaatgcca tgatacagta caattatttt   7860
gggacatttg ctagactctt gttgatgatg catgatcctg ctcttcgtca atcattgtat   7920
gaagttcaag ataagatacc gggcttgcac agttctactt tcaaatacgc catgttgtat   7980 ttggacccett ccattggagg agtgtcgggc atgtctttgt ccaggttttt gattagagcc   8040
ttcccagatc ccgtaacaga aagtctctca ttctggagat tcatccatgt acatgctcga   8100
agtgagcatc tgaaggagat gagtgcagta tttggaaacc ccgagatagc caagtttcga   8160
ataactcaca tagacaagct agtagaagat ccaacctctc tgaacatcgc tatgggaatg   8220
agtccagcga acttgttaaa gactgaggtt aaaaaatgct taatcgaatc aagacaaacc   8280
atcaggaacc aggtgattaa ggatgcaacc atatatttgt atcatgaaga ggatcggctc   8340
agaagtttct tatggtcaat aaatcctctg ttccctagat ttttaagtga attcaaatca   8400 ggcactttt tgggagtcgc agacgggctc atcagtctat ttcaaaattc tcgtactatt   8460
cggaactcct ttaagaaaaa gtatcatagg gaattggatg atttgattgt gaggagtgag   8520
gtatcctctt tgacacattt agggaaactt catttgagaa ggggatcatg taaaatgtgg   8580
acatgttcag ctactcatgc tgacacatta agatacaaat cctggggccg tacagttatt   8640
gggacaactg taccccatcc attagaaatg ttgggtccac aacatcgaaa agagactcct   8700
tgtgcaccat gtaacacatc agggttcaat tatgttctg tgcattgtcc agacgggatc   8760
catgacgtct ttagttcacg gggaccattg cctgcttatc tagggtctaa aacatctgaa   8820
tctacatcta ttttgcagcc ttgggaaagg gaaagcaaag tcccactgat taaaagagct   8880
acacgtctta gagatgctat ctcttggttt gttgaacccg actctaaact agcaatgact   8940
atactttcta acatccactc tttaacaggc gaagaatgga ccaaaaggca gcatgggttc   9000
aaaagaacag ggtctgccct tcataggttt tcgacatctc ggatgagcca tggtgggttc   9060
gcatctcaga gcactgcagc attgaccagg ttgatggcaa ctacagacac catgagggat   9120
ctgggagatc agaatttcga ctttttattc caagcaacgt tgctctatgc tcaaattacc   9180
accactgttg caagagacgg atggatcacc agttgtacag atcattatca tattgcctgt   9240
aagtcctgtt tgagacccat agaagagatc accctggact caagtatgga ctacacgccc   9300
ccagatgtat cccatgtgct gaagacatgg aggaatgggg aaggttcgtg gggacaagag   9360
ataaaacaga tctatccttt agaagggaat tggaagaatt tagcacctgc tgagcaatcc   9420
tatcaagtcg gcagatgtat aggttttcta tatggagact tggcgtatag aaaatctact   9480
catgccgagg acagttctct atttcctcta tctatacaag gtcgtattag aggtcgaggt   9540
ttcttaaaag ggttgctaga cggattaatg agagcaagtt gctgccaagt aatacaccgg   9600
agaagtctgg ctcatttgaa gaggccggcc aacgcagtgt acgagggttt gatttacttg   9660
attgataaat tgagtgtatc acctccattc ctttctctta ctagatcagg acctattaga   9720
gacgaattag aaacgattcc ccacaagatc ccaacctcct atccgacaag caaccgtgat   9780 atggggggtga ttgtcagaaa ttacttcaaa taccaatgcc gtctaattga aaagggaaaa   9840
tacagatcac attattcaca attatggtta ttctcagatg tcttatccat agacttcatt   9900
ggaccattct ctattttccac cacctcttg caaatcctat acaagccatt tttatctggg   9960
aaagataaga atgagttgag agagctggca aatctttctt cattgctaag atcaggagag  10020
```

```
gggtgggaag acatacatgt gaaattcttc accaaggaca tattattgtg tccagaggaa    10080
atcagacatg cttgcaagtt cgggattgct aaggataata ataaagacat gagctatccc    10140
ccttggggaa gggaatccag agggacaatt acaacaatcc ctgtttatta tacgaccacc    10200
ccttacccaa agatgctaga gatgcctcca agaatccaaa atcccctgct gtccggaatc    10260
aggttgggcc aattaccaac tggcgctcat tataaaattc ggagtatatt acatggaatg    10320
ggaatccatt acagggactt cttgagttgt ggagacggct ccggagggat gactgctgca    10380
ttactacgag aaaatgtgca tagcagagga atattcaata gtctgttaga attatcaggg    10440
tcagtcatgc gaggcgcctc tcctgagccc cccagtgccc tagaaacttt aggaggagat    10500
aaatcgagat gtgtaaatgg tgaaacatgt tgggaatatc catctgactt atgtgaccca    10560
aggacttggg actatttcct ccgactcaaa gcaggcttgg ggcttcaaat tgatttaatt    10620
gtaatggata tggaagttcg ggattcttct actagcctga aaattgagac gaatgttaga    10680
aattatgtgc accggatttt ggatgagcaa ggagttttaa tctacaagac ttatggaaca    10740
tatatttgtg agagcgaaaa gaatgcagta acaatccttg gtcccatgtt caagacggtc    10800
gacttagttc aaacagaatt tagtagttct caaacgtctg aagtatatat ggtatgtaaa    10860
ggtttgaaga aattaatcga tgaacccaat cccgattggt cttccatcaa tgaatcctgg    10920
aaaaacctgt acgcattcca gtcatcagaa caggaatttg ccagagcaaa gaaggttagt    10980
acatacttta ccttgacagg tattccctcc caattcattc ctgatccttt tgtaaacatt    11040
gagactatgc tacaaatatt cggagtaccc acgggtgtgt ctcatgcggc tgccttaaaa    11100
tcatctgata gacctgcaga tttattgacc attagccttt tttatatggc gattatatcg    11160
tattataaca tcaatcatat cagagtagga ccgatacctc cgaacccccc atcagatgga    11220
attgcacaaa atgtggggat cgctataact ggtataagct tttggctgag tttgatggag    11280
aaagacattc cactatatca acagtgtttg gcagttatcc agcaatcatt tccgattagg    11340
tgggaggcta tttcagtaaa aggaggatac aagcagaagt ggagtactag aggtgatggg    11400
ctcccaaaag atacccgaat ttcagactcc ttggccccaa tcgggaactg gatcagatct    11460
ttggaattgg tccgaaacca agttcgtcta aatccattca ataagatctt gttcaatcag    11520
ctatgtcgta cagtggataa tcatttgaag tggtcaaatt tgcgaaaaaa cacaggaatg    11580
attgaatgga tcaatgggcg aatttcaaaa gaagaccggt ctatactgat gttgaagagt    11640
gacctacatg aggaaaactc ttggagagat taaaaaatca ggaggagact ccaaacttta    11700
agtatgaaaa aaactttgat ccttaagacc ctcttgtggt ttttattttt tatctggttt    11760
tgtggtcttc gt                                                         11772
```

<210> SEQ ID NO 10
<211> LENGTH: 12052
<212> TYPE: DNA
<213> ORGANISM: Artificial Sequence
<220> FEATURE:
<223> OTHER INFORMATION: Synthetic Construct

<400> SEQUENCE: 10

```
acgaagacaa acaaaccatt attatcatta aaaggctcag gagaaacttt aacagtaatc      60
aaaatgtctg ttacagtcaa gagaatcatt gacaacacag tcatagttcc aaaacttcct     120
gcaaatgagg atccagtgga atacccggca gattacttca aaaatcaaa ggagattcct     180
ctttacatca atactacaaa aagtttgtca gatctaagag gatatgtcta ccaaggcctc     240
```

-continued

```
aaatccggaa atgtatcaat catacatgtc aacagctact tgtatggagc attaaaggac    300
atccggggta agttggataa agattggtca agtttcggaa taaacatcgg gaaagcaggg    360
gatacaatcg gaatatttga ccttgtatcc ttgaaagccc tggacggcgt acttccagat    420
ggagtatcgg atgcttccag aaccagcgca gatgacaaat ggttgccttt gtatctactt    480
ggcttataca gagtgggcag aacacaaatg cctgaataca gaaaaaagct catggatggg    540
ctgacaaatc aatgcaaaat gatcaatgaa cagtttgaac ctcttgtgcc agaaggtcgt    600 gacattttg atgtgtgggg aaatgacagt aattacacaa aaattgtcgc tgcagtggac    660
atgttcttcc acatgttcaa aaaacatgaa tgtgcctcgt tcagatacgg aactattgtt    720
tccagattca agattgtgc tgcattggca acatttggac acctctgcaa ataaccgga     780 atgtctacag aagatgtaac gacctggatc ttgaaccgag aagttgcaga tgaaatggtc    840
caaatgatgc ttccaggcca agaaattgac aaggccgatt catacatgcc ttatttgatc    900
gactttggat tgtcttctaa gtctccatat tcttccgtca aaaaccctgc cttccacttc    960
tgggggcaat tgacagctct tctgctcaga tccaccagag caaggaatgc ccgacagcct   1020
gatgacattg agtatacatc tcttactaca gcaggtttgt tgtacgctta gcagtagga    1080 tcctctgccg acttggcaca acagttttgt gttggagata caaatacac tccagatgat    1140 agtaccggag gattgacgac taatgcaccg ccacaaggca gagatgtggt cgaatggctc    1200
ggatggtttg aagatcaaaa cagaaaaccg actcctgata tgatgcagta tgcgaaaaga    1260
gcagtcatgt cactgcaagg cctaagagag aagacaattg gcaagtatgc taagtcagaa    1320
tttgacaaat gaccctataa ttctcagatc acctattata tattatgcta catatgaaaa    1380
aaactaacag atatcatgga taatctcaca aaagttcgtg agtatctcaa gtcctactct    1440
cgtctagatc aggcggtagg agagatagat gagatcgaag cacaacgagc tgaaaagtcc    1500
aattatgagt tgttccaaga ggacggagtg aagagcata ctaggccctc ttattttcag     1560
gcagcagatg attctgacac agaatctgaa ccagaaattg aagacaatca aggcttgtat    1620
gtaccagatc cggaagctga gcaagttgaa ggctttatac aggggccttt agatgactat    1680
gcagatgagg acgtggatgt tgtattcact tcggactgga acagcctga gcttgaatcc    1740 gacgagcatg gaaagacctt acggttgaca ttgccagagg gtttaagtgg agagcagaaa    1800
tcccagtggc ttttgacgat taaagcagtc gttcaaagtg ccaaacactg gaatctggca    1860
gagtgcacat ttgaagcatc gggagaaggg gtcatcataa aaaagcgcca gataactccg    1920
gatgtatata aggtcactcc agtgatgaac acacatccgt accaatcaga agccgtatca    1980
gatgtttggt ctctctcaaa gacatccatg actttccaac ccaagaaagc aagtcttcag    2040
cctctcacca tatccttgga tgaattgttc tcatctagag gagaattcat ctctgtcgga    2100
ggtaacggac gaatgtctca taaagaggcc atcctgctcg gtctgaggta caaaaagttg    2160
tacaatcagg cgagagtcaa atattctctg tagactatga aaaaaagtaa cagatatcac    2220
aatctaagtg ttatcccaat ccattcatca tgagttcctt aaagaagatt ctcggtctga    2280
aggggaaagg taagaaatct aagaaattag ggatcgcacc cccccttat gaagaggaca     2340 ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga acgtcccctt ctacaaaatc ttggctttt    2580 tgggttcttc taatctaaag gccactccag cggtattggc agatcaaggt caaccagagt    2640
```

```
atcacgctca ctgcgaaggc agggcttatt tgccacatag gatggggaag accccctccca    2700 tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctagc ttccagcttc tgaacaatcc ccggtttact cagtctctcc taattccagc    3000
ctttcgaaca actaatatcc tgtcttttct atccctatga aaaaaactaa cagatctcga    3060
gatggcggct ctgaagagtt ggctgtcgcg cagcgtaact tcattcttca ggtacagaca    3120
gtgtttgtgt gttcctgttg tggctaactt taagaagcgg tgtttctcag aattgataag    3180
accatggcac aaaactgtga cgattggctt tggagtaacc ctgtgtgcgg ttcctattgc    3240
acagaaatca gagcctcatt cccttagtag tgaagcattg atgaggagag cagtgtcttt    3300
ggtaacagat agcaccctcta cctttctctc tcagaccaca tatgcgttga ttgaagctat    3360
tactgaatat actaaggctg tttataacctt aacttctctt taccgacaat atacaagttt    3420
acttgggaaa atgaattcag aggaggaaga tgaagtgtgg caggtgatca taggagccag    3480
agctgagatg acttcaaaac accaagagta cttgaagctg gaaaccactt ggatgactgc    3540
agttggtctt tcagagatgg cagcagaagc tgcatatcaa actggcgcag atcaggcctc    3600
tataaccgcc aggaatcaca ttcagctggt gaaactgcag gtggaagagg tgcaccagct    3660
ctcccggaaa gcagaaacca agctggcaga agcacagata gaagagctcc gtcagaaaac    3720
acaggaggaa ggggaggagc gggctgagtc ggagcaggag gcctacctgc gtgaggattg    3780
actcgagtat attttaattt ttaattttta tgaaaaaaac taacagatct cgagctgtta    3840
atgctaatcg tgataggggt ttttgcctcc aactgactcc tacatattag cattaacagc    3900
tcgagtatat tttaattttt aattttttatg aaaaaaacta acagagatcg atctgtttcc    3960
ttgacaccat gaagtgcctt ttgtacttag cttttttatt catcggggtg aattgcaagt    4020
tcaccatagt ttttccacac aaccgaaaag gaaactggaa aaatgttcct tccaattacc    4080
attattgccc gtcaagctca gatttaaatt ggcataatga cttaataggc acagccttac    4140
aagtcaaaat gcccaagagt cacaaggcta ttcaagcaga cggttggatg tgtcatgctt    4200
ccaaatgggt cactacttgt gatttccgct ggtacggacc ggagtatata acacattcca    4260
tccgatcctt cactccatct gtagaacaat gcaaggaaag cattgaacaa acgaaacaag    4320
gaacttggct gaatccaggc ttccctcctc aaagttgtgg atatgcaact gtgacggatg    4380
ctgaagcagc gattgtccag gtgactcctc accatgtgct tgttgatgaa tacacaggag    4440
aatgggttga ttcacagttc atcaacgaaa atgcagcaa tgacatatgc cccactgtcc    4500
ataactccac aacctggcat tccgactata aggtcaaagg gctatgtgat tctaacctca    4560
tttccatgga catcaccttc ttctcagagg acggagagct atcatcccta ggaaaggagg    4620
gcacagggtt cagaagtaac tactttgctt atgaaactgg agacaaggcc tgcaaaatgc    4680
agtactgcaa gcattgggga gtcagactcc catcaggtgt ctggttcgag atggctgata    4740
aggatctctt tgctgcagcc agattccctg aatgcccaga agggtcaagt atctctgctc    4800
catctcagac ctcagtggat gtaagtctca ttcaggacgt tgagaggatc ttggattatt    4860
ccctctgcca agaaacctgg agcaaaatca gagcgggtct tcccatctct ccagtggatc    4920
tcagctatct tgctcctaaa aacccaggaa ccggtcctgt ctttaccata atcaatggta    4980
```

```
ccctaaaata ctttgagacc agatacatca gagtcgatat tgctgctcca atcctctcaa    5040
gaatggtcgg aatgatcagt ggaactacca cagaaaggga actgtgggat gactgggctc    5100
catatgaaga cgtggaaatt ggacccaatg gagttctgag gaccagttca ggatataagt    5160 ttccttata tatgattgga catggtatgt tggactccga tcttcatctt agctcaaagg     5220
ctcaggtgtt tgaacatcct cacattcaag acgctgcttc gcagcttcct gatgatgaga    5280
ctttattttt tggtgatact gggctatcca aaaatccaat cgagtttgta gaaggttggt    5340
tcagtagttg gaagagctct attgcctctt tttgctttat catagggtta atcattggac    5400
tattcttggt tctccgagtt ggtatttatc tttgcattaa attaaagcac accaagaaaa    5460
gacagattta tacagacata gagatgaacc gacttggaaa gtaactcaaa tcctgcacaa    5520
cagattcttc atgtttgaac caaatcaact tgtgatatca tgctcaaaga ggccttaatt    5580
atattttaat ttttaattt tatgaaaaaa actaacagca atcatggaag tccacgattt      5640
tgagaccgac gagttcaatg atttcaatga agatgactat gccacaagag aattcctgaa    5700
tcccgatgag cgcatgacgt acttgaatca tgctgattac aatttgaatt ctcctctaat    5760
tagtgatgat attgacaatt tgatcaggaa attcaattct cttccgattc cctcgatgtg    5820
ggatagtaag aactgggatg gagttcttga gatgttaaca tcatgtcaag ccaatcccat    5880
ctcaacatct cagatgcata aatggatggg aagttggtta atgtctgata atcatgatgc    5940
cagtcaaggg tatagttttt tacatgaagt ggacaaagag gcagaaataa catttgacgt    6000
ggtggagacc ttcatccgcg gctggggcaa caaaccaatt gaatacatca aaaaggaaag    6060
atggactgac tcattcaaaa ttctcgctta tttgtgtcaa aagttttttgg acttacacaa   6120 gttgacatta atcttaaatg ctgtctctga ggtggaattg ctcaacttgg cgaggacttt    6180
caaaggcaaa gtcagaagaa gttctcatgg aacgaacata tgcaggatta gggttcccag    6240
cttgggtcct acttttattt cagaaggatg gcttacttc aagaaacttg atattctaat      6300
ggaccgaaac tttctgttaa tggtcaaaga tgtgattata gggaggatgc aaacggtgct    6360
atccatggta tgtagaatag acaacctgtt ctcagagcaa gacatcttct cccttctaaa    6420
tatctacaga attggagata aaattgtgga gaggcaggga aattttttctt atgacttgat   6480 taaaatggtg gaaccgatat gcaacttgaa gctgatgaaa ttagcaagag aatcaaggcc    6540
tttagtccca caattccctc attttgaaaa tcatatcaag acttctgttg atgaaggggc    6600
aaaaattgac cgaggtataa gattcctcca tgatcagata atgagtgtga aaacagtgga    6660
tctcacactg gtgatttatg gatcgttcag acattgggt catccttta tagattatta      6720 cactggacta gaaaaattac attcccaagt aaccatgaag aaagatattg atgtgtcata    6780
tgcaaaagca cttgcaagtg atttagctcg gattgttcta tttcaacagt tcaatgatca    6840
taaaaagtgg ttcgtgaatg gagacttgct ccctcatgat catcccttta aaagtcatgt    6900
taaagaaaat acatggccca cagctgctca agttcaagat tttggagata atggcatga    6960 acttccgctg attaaatgtt ttgaaatacc cgacttacta gacccatcga taatatactc    7020
tgacaaaagt cattcaatga ataggtcaga ggtgttgaaa catgtccgaa tgaatccgaa    7080
cactcctatc cctagtaaaa aggtgttgca gactatgttg gacacaaagg ctaccaattg    7140
gaaagaattt cttaaagaga ttgatgagaa gggcttagat gatgatgatc taattattgg    7200
tcttaaagga aaggagaggg aactgaagtt ggcaggtaga ttttttctccc taatgtcttg   7260 gaaattgcga gaatactttg taattaccga atatttgata aagactcatt tcgtccctat    7320
gtttaaaggc ctgacaatgg cggacgatct aactgcagtc attaaaaaga tgttagattc    7380
```

```
ctcatccggc caaggattga agtcatatga ggcaatttgc atagccaatc acattgatta    7440
cgaaaaatgg aataaccacc aaaggaagtt atcaaacggc ccagtgttcc gagttatggg    7500
ccagttctta ggttatccat ccttaatcga gagaactcat gaatttttg agaaaagtct    7560 tatatactac aatggaagac cagacttgat gcgtgttcac aacaacacac tgatcaattc    7620
aacctcccaa cgagtttgtt ggcaaggaca agagggtgga ctggaaggtc tacggcaaaa    7680
aggatggagt atcctcaatc tactggttat tcaaagagag gctaaaatca gaaacactgc    7740
tgtcaaagtc ttggcacaag gtgataatca agttatttgc acacagtata aaacgaagaa    7800
atcgagaaac gttgtagaat tacagggtgc tctcaatcaa atggtttcta ataatgagaa    7860
aattatgact gcaatcaaaa tagggacagg gaagttagga cttttgataa atgacgatga    7920
gactatgcaa tctgcagatt acttgaatta tggaaaaata ccgatttttcc gtggagtgat    7980 tagagggtta gagaccaaga gatggtcacg agtgacttgt gtcaccaatg accaaatacc    8040
cacttgtgct aatataatga gctcagtttc cacaaatgct ctcaccgtag ctcattttgc    8100
tgagaaccca atcaatgcca tgatacagta caattatttt gggacatttg ctagactctt    8160
gttgatgatg catgatcctg ctcttcgtca atcattgtat gaagttcaag ataagatacc    8220
gggcttgcac agttctactt tcaaatacgc catgttgtat ttggacccctt ccattggagg    8280 agtgtcgggc atgtctttgt ccaggttttt gattagagcc ttcccagatc ccgtaacaga    8340
aagtctctca ttctggagat tcatccatgt acatgctcga agtgagcatc tgaaggagat    8400
gagtgcagta tttggaaacc ccgagatagc caagtttcga ataactcaca tagacaagct    8460
agtagaagat ccaacctctc tgaacatcgc tatgggaatg agtccagcga acttgttaaa    8520
gactgaggtt aaaaaatgct taatcgaatc aagacaaacc atcaggaacc aggtgattaa    8580
ggatgcaacc atatatttgt atcatgaaga ggatcggctc agaagtttct tatggtcaat    8640
aaatcctctg ttccctagat ttttaagtga attcaaatca ggcactttt tgggagtcgc    8700 agacgggctc atcagtctat ttcaaaattc tcgtactatt cggaactcct ttaagaaaaa    8760
gtatcatagg gaattggatg atttgattgt gaggagtgag gtatcctctt tgacacattt    8820
agggaaactt catttgagaa ggggatcatg taaaatgtgg acatgttcag ctactcatgc    8880
tgacacatta agatacaaat cctggggccg tacagttatt gggacaactg taccccatcc    8940
attagaaatg ttgggtccac aacatcgaaa agagactcct gtgcaccat gtaacacatc    9000 agggttcaat tatgtttctg tgcattgtcc agacgggatc catgacgtct ttagttcacg    9060
gggaccattg cctgcttatc tagggtctaa aacatctgaa tctacatcta ttttgcagcc    9120
ttgggaaagg gaaagcaaag tcccactgat taaaagagct acacgtctta gagatgctat    9180
ctcttggttt gttgaacccg actctaaact agcaatgact atactttcta acatccactc    9240
tttaacaggc gaagaatgga ccaaaaggca gcatgggttc aaaagaacag ggtctgccct    9300
tcataggttt tcgacatctc ggatgagcca tggtgggttc gcatctcaga gcactgcagc    9360
attgaccagg ttgatggcaa ctacagacac catgagggat ctgggagatc agaatttcga    9420 cttttttattc caagcaacgt tgctctatgc tcaaattacc accactgttg caagagacgg    9480
atggatcacc agttgtacag atcattatca tattgcctgt aagtcctgtt tgagaccat    9540 agaagagatc accctggact caagtatgga ctacacgccc ccagatgtat cccatgtgct    9600
gaagacatgg aggaatgggg aaggttcgtg gggacaagag ataaaacaga tctatccttt    9660
agaagggaat tggaagaatt tagcacctgc tgagcaatcc tatcaagtcg gcagatgtat    9720
```

```
aggtttttcta tatggagact tggcgtatag aaaatctact catgccgagg acagttctct   9780
atttcctcta tctatacaag gtcgtattag aggtcgaggt ttcttaaaag ggttgctaga    9840
cggattaatg agagcaagtt gctgccaagt aatacaccgg agaagtctgg ctcatttgaa    9900
gaggccggcc aacgcagtgt acggaggttt gatttacttg attgataaat tgagtgtatc    9960
acctccattc ctttctctta ctagatcagg acctattaga gacgaattag aaacgattcc   10020
ccacaagatc ccaacctcct atccgacaag caaccgtgat atgggggtga ttgtcagaaa   10080
ttacttcaaa taccaatgcc gtctaattga aaagggaaaa tacagatcac attattcaca   10140
attatggtta ttctcagatg tcttatccat agacttcatt ggaccattct ctatttccac   10200
caccctcttg caaatcctat acaagccatt tttatctggg aaagataaga atgagttgag   10260
agagctggca aatctttctt cattgctaag atcaggagag gggtgggaag acatacatgt   10320
gaaattcttc accaaggaca tattattgtg tccagaggaa atcagacatg cttgcaagtt   10380
cgggattgct aaggataata ataaagacat gagctatccc ccttggggaa gggaatccag   10440
agggacaatt acaacaatcc ctgtttatta tacgaccacc ccttacccaa agatgctaga   10500
gatgcctcca agaatccaaa atccctgct gtccggaatc aggttgggcc aattaccaac    10560
tggcgctcat tataaaattc ggagtatatt acatggaatg ggaatccatt acagggactt   10620
cttgagttgt ggagacggct ccggagggat gactgctgca ttactacgag aaaatgtgca   10680
tagcaggaga atattcaata gtctgttaga attatcaggg tcagtcatgc gaggcgcctc   10740
tcctgagccc cccagtgccc tagaaacttt aggaggagat aaatcgagat gtgtaaatgg   10800
tgaaacatgt tgggaatatc catctgactt atgtgaccca aggacttggg actatttcct   10860
ccgactcaaa gcaggcttgg ggcttcaaat tgatttaatt gtaatggata tggaagttcg   10920
ggattcttct actagcctga aaattgagac gaatgttaga aattatgtgc accggatttt   10980
ggatgagcaa ggagttttaa tctacaagac ttatggaaca tatatttgtg agagcgaaaa   11040
gaatgcagta acaatccttg gtcccatgtt caagacggtc gacttagttc aaacagaatt   11100
tagtagttct caaacgtctg aagtatatat ggtatgtaaa ggtttgaaga aattaatcga   11160
tgaacccaat cccgattggt cttccatcaa tgaatcctgg aaaaacctgt acgcattcca   11220
gtcatcagaa caggaatttg ccagagcaaa gaaggttagt acatacttta ccttgacagg   11280
tattccctcc caattcattc ctgatccttt tgtaaacatt gagactatgc tacaaatatt   11340
cggagtaccc acgggtgtgt ctcatgcggc tgccttaaaa tcatctgata gacctgcaga   11400
tttattgacc attagccttt tttatatggc gattatatcg tattataaca tcaatctatt   11460
cagagtagga ccgatacctc cgaaccccc atcagatgga attgcacaaa atgtggggat   11520
cgctataact ggtataagct tttggctgag tttgatggag aaagacattc cactatatca   11580
acagtgtttg gcagttatcc agcaatcatt tccgattagg tgggaggcta tttcagtaaa   11640
aggaggatac aagcagaagt ggagtactag aggtgatggg ctcccaaaag atacccgaat   11700
ttcagactcc ttggccccaa tcgggaactg gatcagatct ttggaattgg tccgaaacca   11760
agttcgtcta aatccattca ataagatctt gttcaatcag ctatgtcgta cagtggataa   11820
tcatttgaag tggtcaaatt tgcgaaaaaa cacaggaatg attgaatgga tcaatgggcg   11880
aatttcaaaa gaagaccggt ctatactgat gttgaagagt gacctacatg aggaaaactc   11940
ttggagagat taaaaaatca ggaggagact ccaaacttta agtatgaaaa aaactttgat   12000
ccttaagacc ctcttgtggt ttttattttt tatctggttt tgtggtcttc gt           12052
```

<210> SEQ ID NO 11
<211> LENGTH: 11890
<212> TYPE: DNA
<213> ORGANISM: Artificial Sequence
<220> FEATURE:
<223> OTHER INFORMATION: Synthetic Construct

<400> SEQUENCE: 11

| | | | | | |
|---|---|---|---|---|---|
| acgaagacaa | acaaaccatt | attatcatta | aaaggctcag | gagaaacttt aacagtaatc | 60 |
| aaaatgtctg | ttacagtcaa | gagaatcatt | gacaacacag | tcatagttcc aaaacttcct | 120 |
| gcaaatgagg | atccagtgga | atacccggca | gattacttca | gaaaatcaaa ggagattcct | 180 |
| ctttacatca | atactacaaa | aagtttgtca | gatctaagag | gatatgtcta ccaaggcctc | 240 |
| aaatccggaa | atgtatcaat | catacatgtc | aacagctact | tgtatggagc attaaaggac | 300 |
| atccggggta | agttggataa | agattggtca | agtttcggaa | taaacatcgg gaaagcaggg | 360 |
| gatacaatcg | gaatatttga | ccttgtatcc | ttgaaagccc | tggacggcgt acttccagat | 420 |
| ggagtatcgg | atgcttccag | aaccagcgca | gatgacaaat | ggttgccttt gtatctactt | 480 |
| ggcttataca | gagtgggcag | aacacaaatg | cctgaataca | gaaaaaagct catggatggg | 540 |
| ctgacaaatc | aatgcaaaat | gatcaatgaa | cagtttgaac | tcttgtgcc agaaggtcgt | 600 |
| gacattttttg | atgtgtgggg | aaatgacagt | aattacacaa | aaattgtcgc tgcagtggac | 660 |
| atgttcttcc | acatgttcaa | aaaacatgaa | tgtgcctcgt | tcagatacgg aactattgtt | 720 |
| tccagattca | agattgtgc | tgcattggca | acatttggac | acctctgcaa aataaccgga | 780 |
| atgtctacag | aagatgtaac | gacctggatc | ttgaaccgag | aagttgcaga tgaaatggtc | 840 |
| caaatgatgc | ttccaggcca | agaaattgac | aaggccgatt | catacatgcc ttatttgatc | 900 |
| gactttggat | tgtcttctaa | gtctccatat | tcttccgtca | aaaaccctgc cttccacttc | 960 |
| tgggggcaat | tgacagctct | tctgctcaga | tccaccagag | caaggaatgc ccgacagcct | 1020 |
| gatgacattg | agtatacatc | tcttactaca | gcaggtttgt | tgtacgctta tgcagtagga | 1080 |
| tcctctgccg | acttggcaca | acagttttgt | gttggagata | caaatacac tccagatgat | 1140 |
| agtaccggag | gattgacgac | taatgcaccg | ccacaaggca | gagatgtggt cgaatggctc | 1200 |
| ggatggtttg | aagatcaaaa | cagaaaaccg | actcctgata | tgatgcagta tgcgaaaaga | 1260 |
| gcagtcatgt | cactgcaagg | cctaagagag | aagacaattg | gcaagtatgc taagtcagaa | 1320 |
| tttgacaaaat | gaccctataa | ttctcagatc | acctattata | tattatgcta catatgaaaa | 1380 |
| aaactaacag | atatcatgga | taatctcaca | aaagttcgtg | agtatctcaa gtcctactct | 1440 |
| cgtctagatc | aggcggtagg | agagatagat | gagatcgaag | cacaacgagc tgaaaagtcc | 1500 |
| aattatgagt | tgttccaaga | ggacggagtg | gaagagcata | ctaggccctc ttattttcag | 1560 |
| gcagcagatg | attctgacac | agaatctgaa | ccagaaattg | aagacaatca aggcttgtat | 1620 |
| gtaccagatc | cggaagctga | gcaagttgaa | ggctttatac | aggggccttt agatgactat | 1680 |
| gcagatgagg | acgtggatgt | tgtattcact | tcggactgga | acagcctga gcttgaatcc | 1740 |
| gacgagcatg | gaaagacctt | acggttgaca | ttgccagagg | gtttaagtgg agagcagaaa | 1800 |
| tcccagtggc | ttttgacgat | taaagcagtc | gttcaaagtg | ccaaacactg gaatctggca | 1860 |
| gagtgcacat | ttgaagcatc | gggagaaggg | gtcatcataa | aaaagcgcca gataactccg | 1920 |
| gatgtatata | aggtcactcc | agtgatgaac | acacatccgt | accaatcaga gccgtatca | 1980 |
| gatgtttggt | ctctctcaaa | gacatccatg | actttccaac | ccaagaaagc aagtcttcag | 2040 |
| cctctcacca | tatccttgga | tgaattgttc | tcatctagag | gagaattcat ctctgtcgga | 2100 |

```
ggtaacggac gaatgtctca taaagaggcc atcctgctcg gtctgaggta caaaaagttg    2160
tacaatcagg cgagagtcaa atattctctg tagactatga aaaaagtaa cagatatcac     2220 aatctaagtg ttatcccaat ccattcatca tgagttcctt aaagaagatt ctcggtctga    2280
aggggaaagg taagaaatct aagaaattag ggatcgcacc acccccttat gaagaggaca    2340
ctagcatgga gtatgctccg agcgctccaa ttgacaaatc ctattttgga gttgacgaga    2400
tggacaccta tgatccgaat caattaagat atgagaaatt cttctttaca gtgaaaatga    2460
cggttagatc taatcgtccg ttcagaacat actcagatgt ggcagccgct gtatcccatt    2520
gggatcacat gtacatcgga atggcaggga acgtcccctt ctacaaaatc ttggctttt     2580 tgggttcttc taatctaaag gccactccag cggtattggc agatcaaggt caaccagagt    2640
atcacgctca ctgcgaaggc agggcttatt tgccacatag gatggggaag acccctccca    2700
tgctcaatgt accagagcac ttcagaagac cattcaatat aggtctttac aagggaacga    2760
ttgagctcac aatgaccatc tacgatgatg agtcactgga agcagctcct atgatctggg    2820
atcatttcaa ttcttccaaa ttttctgatt tcagagagaa ggccttaatg tttggcctga    2880
ttgtcgagaa aaaggcatct ggagcgtggg tcctggattc tatcagccac ttcaaatgag    2940
ctagtctagc ttccagcttc tgaacaatcc ccggtttact cagtctctcc taattccagc    3000
ctttcgaaca actaatatcc tgtcttttct atccctatga aaaaactaa cagatctcga    3060 gatggcggtt cctattgcac agaaatcaga gcctcattcc cttagtagtg aagcattgat    3120
gaggagagca gtgtctttgg taacagatag cacctctacc tttctctctc agaccacata    3180
tgcgttgatt gaagctatta ctgaatatac taaggctgtt tataccttaa cttctctta    3240 ccgacaatat acaagtttac ttgggaaaat gaattcagag gaggaagatg aagtgtggca    3300
ggtgatcata ggagccagag ctgagatgac ttcaaaacac caagagtact tgaagctgga    3360
aaccacttgg atgactgcag ttggtctttc agagatggca gcagaagctg catatcaaac    3420
tggcgcagat caggcctcta taaccgccag gaatcacatt cagctggtga aactgcaggt    3480
ggaagaggtg caccagctct cccggaaagc agaaaccaag ctggcagaag cacagataga    3540
agagctccgt cagaaaacac aggaggaagg ggaggagcgg gctgagtcgg agcaggaggc    3600
ctacctgcgt gaggattgac tcgagtatat tttaattttt aatttttatg aaaaaaacta    3660
acagatctcg agctgttaat gctaatcgtg atagggggttt ttgcctccaa ctgactccta    3720
catattagca ttaacagctc gagtatattt taattttaa tttttatgaa aaaactaac    3780 agagatcgat ctgtttcctt gacaccatga agtgcctttt gtacttagct tttttattca    3840
tcggggtgaa ttgcaagttc accatagttt ttccacacaa ccgaaaagga aactggaaaa    3900
atgttccttc caattaccat tattgcccgt caagctcaga tttaaattgg cataatgact    3960
taataggcac agccttacaa gtcaaaatgc ccaagagtca caaggctatt caagcagacg    4020
gttggatgtg tcatgcttcc aaatgggtca ctacttgtga tttccgctgg tacgaccgg    4080 agtatataac acattccatc cgatccttca ctccatctgt agaacaatgc aaggaaagca    4140
ttgaacaaac gaaacaagga acttggctga atccaggctt ccctcctcaa agttgtggat    4200
atgcaactgt gacggatgct gaagcagcga ttgtccaggt gactcctcac catgtgcttg    4260
ttgatgaata cacaggagaa tgggttgatt cacagttcat caacggaaaa tgcagcaatg    4320
acatatgccc cactgtccat aactccacaa cctggcattc cgactataag gtcaagggc    4380 tatgtgattc taacctcatt tccatggaca tcaccttctt ctcagaggac ggagagctat    4440
catccctagg aaaggagggc acagggttca gaagtaacta ctttgcttat gaaactggag    4500
```

```
acaaggcctg caaaatgcag tactgcaagc attggggagt cagactccca tcaggtgtct   4560
ggttcgagat ggctgataag gatctctttg ctgcagccag attccctgaa tgcccagaag   4620
ggtcaagtat ctctgctcca tctcagacct cagtggatgt aagtctcatt caggacgttg   4680
agaggatctt ggattattcc ctctgccaag aaacctggag caaaatcaga gcgggtcttc   4740
ccatctctcc agtggatctc agctatcttg ctcctaaaaa cccaggaacc ggtcctgtct   4800
ttaccataat caatggtacc ctaaaatact ttgagaccag atacatcaga gtcgatattg   4860
ctgctccaat cctctcaaga atggtcggaa tgatcagtgg aactaccaca gaaagggaac   4920
tgtgggatga ctgggctcca tatgaagacg tggaaattgg acccaatgga gttctgagga   4980
ccagttcagg atataagttt cctttatata tgattggaca tggtatgttg gactccgatc   5040
ttcatcttag ctcaaaggct caggtgtttg aacatcctca cattcaagac gctgcttcgc   5100
agcttcctga tgatgagact ttattttttg gtgatactgg gctatccaaa aatccaatcg   5160
agtttgtaga aggttggttc agtagttgga agagctctat tgcctctttt tgctttatca   5220
tagggttaat cattggacta ttcttggttc tccgagttgg tatttatctt tgcattaaat   5280
taaagcacac caagaaaaga cagatttata cagacataga gatgaaccga cttggaaagt   5340
aactcaaatc ctgcacaaca gattcttcat gtttgaacca atcaacttg tgatatcatg    5400 ctcaaagagg ccttaattat attttaattt ttaattttta tgaaaaaaac taacagcaat   5460
catggaagtc cacgattttg agaccgacga gttcaatgat ttcaatgaag atgactatgc   5520
cacaagagaa ttcctgaatc ccgatgagcg catgacgtac ttgaatcatg ctgattacaa   5580
tttgaattct cctctaatta gtgatgatat tgacaatttg atcaggaaat tcaattctct   5640
tccgattccc tcgatgtggg atagtaagaa ctgggatgga gttcttgaga tgttaacatc   5700
atgtcaagcc aatcccatct caacatctca gatgcataaa tggatgggaa gttggttaat   5760
gtctgataat catgatgcca gtcaagggta tagttttta catgaagtgg acaaagaggc   5820
agaaataaca tttgacgtgg tggagacctt catccgcggc tggggcaaca aaccaattga   5880
atacatcaaa aaggaaagat ggactgactc attcaaaatt ctcgcttatt tgtgtcaaaa   5940 gttttttggac ttacacaagt tgacattaat cttaaatgct gtctctgagg tggaattgct   6000
caacttggcg aggactttca aaggcaaagt cagaagaagt tctcatggaa cgaacatatg   6060
caggattagg gttcccagct tgggtcctac ttttattttca gaaggatggg cttacttcaa   6120
gaaacttgat attctaatgg accgaaactt tctgttaatg gtcaaagatg tgattatagg   6180
gaggatgcaa acggtgctat ccatggtatg tagaatagca aacctgttct cagagcaaga   6240
catcttctcc cttctaaaata tctacagaat tggagataaa attgtggaga ggcagggaaa   6300
tttttcttat gacttgatta aaatggtgga accgatatgc aacttgaagc tgatgaaatt   6360
agcaagagaa tcaaggcctt tagtcccaca attccctcat tttgaaaatc atatcaagac   6420
ttctgttgat gaaggggcaa aaattgaccg aggtataaga ttcctccatg atcagataat   6480
gagtgtgaaa acagtggatc tcacactggt gatttatgga tcgttcagac attggggtca   6540
tccttttata gattattaca ctggactaga aaaattacat tcccaagtaa ccatgaagaa   6600
agatattgat gtgtcatatg caaaagcact tgcaagtgat ttagctcgga ttgttctatt   6660
tcaacagttc aatgatcata aaaagtggtt cgtgaatgga gacttgctcc ctcatgatca   6720 tcccttaaa agtcatgtta aagaaaaatac atggcccaca gctgctcaag ttcaagattt   6780
tggagataaa tggcatgaac ttccgctgat taaatgtttt gaaataccc acttactaga   6840
```

```
cccatcgata atatactctg acaaaagtca ttcaatgaat aggtcagagg tgttgaaaca    6900
tgtccgaatg aatccgaaca ctcctatccc tagtaaaaag gtgttgcaga ctatgttgga    6960
cacaaaggct accaattgga aagaatttct aaagagatt gatgagaagg cttagatga     7020
tgatgatcta attattggtc ttaaaggaaa ggagagggaa ctgaagttgg caggtagatt    7080
tttctcccta atgtcttgga aattgcgaga atactttgta attaccgaat atttgataaa    7140
gactcatttc gtccctatgt ttaaaggcct gacaatggcg gacgatctaa ctgcagtcat    7200
taaaaagatg ttagattcct catccggcca aggattgaag tcatatgagg caatttgcat    7260
agccaatcac attgattacg aaaaatggaa taaccaccaa aggaagttat caaacggccc    7320
agtgttccga gttatgggcc agttcttagg ttatccatcc ttaatcgaga gaactcatga    7380
attttttgag aaaagtctta tatactacaa tggaagacca gacttgatgc gtgttcacaa    7440
caacacactg atcaattcaa cctcccaacg agtttgttgg caaggacaag agggtggact    7500
ggaaggtcta cggcaaaaag gatggagtat cctcaatcta ctggttattc aaagagaggc    7560
taaaatcaga aacactgctg tcaaagtctt ggcacaaggt gataatcaag ttatttgcac    7620
acagtataaa acgaagaaat cgagaaacgt tgtagaatta cagggtgctc tcaatcaaat    7680
ggtttctaat aatgagaaaa ttatgactgc aatcaaaata gggacaggga agttaggact    7740
tttgataaat gacgatgaga ctatgcaatc tgcagattac ttgaattatg gaaaaatacc    7800
gattttccgt ggagtgatta gagggttaga gaccaagaga tggtcacgag tgacttgtgt    7860
caccaatgac caaataccca cttgtgctaa tataatgagc tcagtttcca caaatgctct    7920
caccgtagct cattttgctg agaacccaat caatgccatg atacagtaca attatttttgg   7980
gacatttgct agactcttgt tgatgatgca tgatcctgct cttcgtcaat cattgtatga    8040
agttcaagat aagataccgg gcttgcacag ttctactttc aaatacgcca tgttgtattt    8100
ggacccttcc attggaggag tgtcgggcat gtctttgtcc aggtttttga ttagagcctt    8160
cccagatccc gtaacagaaa gtctctcatt ctggagattc atccatgtac atgctcgaag    8220
tgagcatctg aaggagatga gtgcagtatt tggaaacccc gagatagcca gtttcgaat    8280
aactcacata gacaagctag tagaagatcc aacctctctg aacatcgcta tgggaatgag    8340
tccagcgaac ttgttaaaga ctgaggttaa aaaatgctta atcgaatcaa gacaaaccat    8400
caggaaccag gtgattaagg atgcaaccat atatttgtat catgaagagg atcggctcag    8460
aagtttctta tggtcaataa atcctctgtt ccctagattt ttaagtgaat tcaaatcagg    8520
cacttttttg ggagtcgcag acgggctcat cagtctattt caaaattctc gtactattcg    8580
gaactccttt aagaaaaagt atcatagga attggatgat ttgattgtga ggagtgaggt    8640
atcctctttg acacatttag ggaaacttca tttgagaagg ggatcatgta aaatgtggac    8700
atgttcagct actcatgctg acacattaag atacaaatcc tggggccgta cagttattgg    8760
gacaactgta ccccatccat tagaaatgtt gggtccacaa catcgaaaag agactccttg    8820
tgcaccatgt aacacatcag ggttcaatta tgtttctgtg cattgtccag acgggatcca    8880
tgacgtcttt agttcacggg gaccattgcc tgcttatcta gggtctaaaa catctgaatc    8940
tacatctatt ttgcagcctt gggaaaggga agcaaagtc ccactgatta aaagagctac    9000
acgtcttaga gatgctatct cttggtttgt tgaacccgac tctaaactag caatgactat    9060
actttctaac atccactctt taacaggcga agaatggacc aaaaggcagc atgggttcaa    9120
aagaacaggg tctgcccttc ataggttttc gacatctcgg atgagccatg gtgggttcgc    9180
atctcagagc actgcagcat tgaccaggtt gatggcaact acagacacca tgaggatct     9240
```

```
gggagatcag aatttcgact ttttattcca agcaacgttg ctctatgctc aaattaccac   9300
cactgttgca agagacggat ggatcaccag ttgtacagat cattatcata ttgcctgtaa   9360
gtcctgtttg agacccatag aagagatcac cctggactca agtatggact acacgccccc   9420
agatgtatcc catgtgctga agacatggag gaatggggaa ggttcgtggg gacaagagat   9480
aaaacagatc tatcctttag aagggaattg gaagaattta gcacctgctg agcaatccta   9540
tcaagtcggc agatgtatag gttttctata tggagacttg gcgtatagaa aatctactca   9600
tgccgaggac agttctctat ttcctctatc tatacaaggt cgtattagag gtcgaggttt   9660
cttaaaaggg ttgctagacg gattaatgag agcaagttgc tgccaagtaa tacaccggag   9720
aagtctggct catttgaaga ggccggccaa cgcagtgtac ggaggtttga tttacttgat   9780
tgataaattg agtgtatcac ctccattcct ttctcttact agatcaggac ctattagaga   9840
cgaattagaa acgattcccc acaagatccc aacctcctat ccgacaagca accgtgatat   9900
gggggtgatt gtcagaaatt acttcaaata ccaatgccgt ctaattgaaa agggaaaata  9960
cagatcacat tattcacaat tatggttatt ctcagatgtc ttatccatag acttcattgg  10020
accattctct atttccacca ccctcttgca aatcctatac aagccatttt tatctgggaa  10080
agataagaat gagttgagag agctggcaaa tctttcttca ttgctaagat caggagaggg  10140
gtgggaagac atacatgtga aattcttcac caaggacata ttattgtgtc cagaggaaat  10200
cagacatgct tgcaagttcg ggattgctaa ggataataat aaagacatga gctatccccc  10260
ttggggaagg gaatccagag ggacaattac aacaatccct gtttattata cgaccacccc  10320
ttacccaaag atgctagaga tgcctccaag aatccaaaat cccctgctgt ccggaatcag  10380
gttgggccaa ttaccaactg gcgctcatta taaaattcgg agtatattac atggaatggg  10440
aatccattac agggacttct tgagttgtgg agacggctcc ggagggatga ctgctgcatt  10500
actacgagaa aatgtgcata gcagaggaat attcaatagt ctgttagaat tatcagggtc  10560
agtcatgcga ggcgcctctc ctgagccccc cagtgcccta gaaactttag gaggagataa  10620
atcgagatgt gtaaatggtg aaacatgttg ggaatatcca tctgacttat gtgacccaag  10680
gacttgggac tatttcctcc gactcaaagc aggcttgggg cttcaaattg atttaattgt  10740
aatggatatg gaagttcggg attcttctac tagcctgaaa attgagacga atgttagaaa  10800
ttatgtgcac cggattttgg atgagcaagg agttttaatc tacaagactt atggaacata  10860
tatttgtgag agcgaaaaga atgcagtaac aatccttggt cccatgttca agacggtcga 10920
cttagttcaa acagaattta gtagttctca aacgtctgaa gtatatatgg tatgtaaagg  10980
tttgaagaaa ttaatcgatg aacccaatcc cgattggtct tccatcaatg aatcctggaa  11040
aaacctgtac gcattccagt catcagaaca ggaatttgcc agagcaaaga aggttagtac  11100
atactttacc ttgacaggta ttccctccca attcattcct gatccttttg taaacattga  11160
gactatgcta caaatattcg gagtacccac gggtgtgtct catgcggctg ccttaaaatc  11220
atctgataga cctgcagatt tattgaccat tagcctttt tatatggcga ttatatcgta  11280
ttataacatc aatcatatca gagtaggacc gataacctccg aaccccccat cagatggaat  11340
tgcacaaaat gtgggatcg ctataactgg tataagcttt tggctgagtt tgatggagaa  11400
agacattcca ctatatcaac agtgtttggc agttatccag caatcatttc cgattaggtg  11460
ggaggctatt tcagtaaaag gaggatacaa gcagaagtgg agtactagag gtgatgggct  11520
cccaaaagat acccgaattt cagactcctt ggccccaatc gggaactgga tcagatcttt  11580
```

```
ggaattggtc cgaaaccaag ttcgtctaaa tccattcaat aagatcttgt tcaatcagct    11640
atgtcgtaca gtggataatc atttgaagtg gtcaaatttg cgaaaaaaca caggaatgat    11700
tgaatggatc aatgggcgaa tttcaaaaga agaccggtct atactgatgt tgaagagtga    11760
cctacatgag gaaaactctt ggagagatta aaaaatcagg aggagactcc aaactttaag    11820
tatgaaaaaa actttgatcc ttaagaccct cttgtggttt ttatttttta tctggttttg    11880
tggtcttcgt                                                           11890

<210> SEQ ID NO 12
<211> LENGTH: 63
<212> TYPE: DNA
<213> ORGANISM: Artificial Sequence
<220> FEATURE:
<223> OTHER INFORMATION: Synthetic Construct

<400> SEQUENCE: 12
ctaacagatc tcgagatgsm actgactcga gtatatttta atttttaatt tttatgaaaa    60
aaa                                                                  63

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct

<400> SEQUENCE: 13
ctaacagatc tcgagatg                                                  18

<210> SEQ ID NO 14
<211> LENGTH: 41
<212> TYPE: DNA
<213> ORGANISM: Artificial Sequence
<220> FEATURE:
<223> OTHER INFORMATION: Synthetic Construct

<400> SEQUENCE: 14
tgactcgagt atattttaat ttttaattt tatgaaaaaa a                          41
```

RECOMBINANT ONCOLYTIC VIRUS

CROSS-REFERENCE TO RELATED APPLICATIONS

This application which is a National Stage of International Application No. PCT/US2018/032915, filed May 16, 2018, which claims benefit of U.S. Provisional Application No. 62/508,430, filed May 19, 2017, which is hereby incorporated herein by reference in its entirety.

SEQUENCE LISTING

This application contains a sequence listing filed in ST.25 format entitled "220702-2910 Sequence Listing" created on Dec. 22, 2022 and having 77,029 bytes. The content of the sequence listing is incorporated herein in its entirety.

BACKGROUND

Autophagy is a survival-promoting pathway that captures, degrades, and recycles intracellular proteins and organelles in lysosomes. Autophagy has dual roles in cancer, acting as both a tumor suppressor by preventing the accumulation of damaged proteins and organelles and as a mechanism of cell survival that can promote the growth of established tumors. There is substantial evidence indicating that autophagy plays a central role in cancer biology (Lippai, M. and Z. Szatmari, Cell Biol Toxicol, 2017 33(2):145-168). On the one hand, autophagy in normal cells can suppress tumorigenesis. Mutations in cancers can result in loss of autophagy functions.

Alternatively, autophagy can also render tumor cells resistant to treatment of anticancer drugs. The cross-talk between autophagy and apoptosis is also critical in cancer biology, but the relationship between the two pathways is complicated. Needed are methods to subvert the protective mechanism of autophagy so apoptosis may be induced more readily.

SUMMARY

Disclosed herein is a recombinant viral vector comprising a nucleic acid encoding a therapeutic gene inserted within an oncolytic virus genome, wherein expression of the therapeutic gene during viral infection causes death in tumor cells. In particular, disclosed herein is a recombinant viral vector comprising a nucleic acid encoding a Second Mitochondria-derived Activator of Caspases (Smac) protein (also known as DIABLO) that specifically binds to at least a portion of an Inhibitor of Apoptosis Protein (IAP). The nucleic acid encoding Smac is inserted within an RNA virus genome as a gene cassette to express the Smac protein during virus infection. In some cases, the Smac protein is a full-length Smac protein. In some cases, the Smac protein lacks the mitochondria-targeting sequence (Δ55 Smac). In some cases, the RNA virus genome further comprises a cassette to express microRNA-155.

In some embodiments, the virus is non-segmented negative-strand RNA viruses (NNSV). In some embodiments, the virus is any virus in the order of Mononegavirales that is transmitted in mammals.

In some embodiments, the virus is any virus in the family of rhabdoviridae that is transmitted in mammals. For example, in some embodiments, the virus is any virus in the genus Vesiculovirus. In some cases, the virus comprises vesicular stomatitis virus (VSV) (Indiana vesiculovirus).

In some embodiments, the virus is any virus in the family of paramyxoviridae that is transmitted in mammals. For example, in some embodiments, the virus is any virus in the genus Henipavirus. In some embodiments, the virus is any virus in the genus Morbillivirus. In some embodiments, the virus is any virus in the genus Respirovirus. In some embodiments, the virus is any virus in the genus Rubulavirus.

In some cases, the oncolytic virus comprises vesicular stomatitis virus (VSV). In some cases, the virus comprises measles virus (MV). In some cases, the virus comprises influenza virus (IFV). In some embodiments, the virus is positive-strand RNA viruses (PSV), such as a picornavirus or alphaviruses. In some cases, the virus comprises poliovirus (PV). In some cases, the virus comprises coxsackie virus (CV). In some cases, the virus comprises Sindbis virus (SINV).

The smac gene can be inserted anywhere in the virus genome as long as it is expressed. In preferred embodiments, the smac gene is inserted such that its expression is delayed until after viral replication. The VSV genome comprises a nucleoprotein (N) gene, a phosphoprotein (P) gene, a matrix protein (M) gene, glycoprotein (G) gene, and the large (L) polymerase protein. The mRNA levels of VSV genes descend from the N gene (close to the 3' end) to the L gene (close to the 5' end) in VSV infection. N and P proteins are required for supporting viral replication, whereas M protein is required for virus assembly. Therefore, in some embodiments, the smac gene is inserted into the VSV genome after the N, P, and m genes so that Smac reaches a significant level only when viral production is well-established. In some cases, the smac gene is inserted after the M gene in viruses from the order of Mononegavirales. Comparable locations within other viral genomes can be determined and used in the disclosed vectors.

In some embodiments, the Smac protein comprises a full-length Smac protein. For example, in some embodiments, the Smac protein comprises the amino acid sequence SEQ ID NO:1, or a conservative variant thereof that specifically binds IAP. In other embodiments, the Smac protein lacks a mitochondria-targeting sequence. For example, in some embodiments, the Smac protein comprises the amino acid sequence SEQ ID NO:2, or a variant thereof that specifically binds IAPs.

The VSV glycoprotein (G) is responsible for attachment to the host receptor and induction of membrane fusion when the virus is exposed to low pH in the endosome during virus entry. In some embodiments, a targeting domain is inserted into the G protein such that the modified G protein can target the VSV to a cancer. For example, the targeting protein domain can be a protein sequence that is six amino acids in length or less that can selectively bind a protein displayed on the surface of a cancer cell. αv integrins and integrin α5β1 recognize the RGD sequence on their respective ligands.

Therefore, in some embodiments, the targeting sequence comprises an RGD sequence that binds an integrin protein. Therefore, in some embodiments, the VSV G protein has the amino acid sequence SEQ ID NO:6.

In some embodiments, the recombinant vector comprises the nucleic acid sequence SEQ ID NO:8, 9, 10, or 11, or a variant thereof that produces viral particle that infects in cancer cells and produces a Smac protein that binds IAPs.

Also disclosed is a cell comprising the disclosed recombinant vector. Also disclosed is a recombinant viral particle comprising the disclosed recombinant vector. Also disclosed is a composition comprising the disclosed recombinant viral particle in pharmaceutically acceptable excipient.

Also disclosed herein is a method of treating a subject with a tumor, comprising administering to the subject an effective amount of composition comprising the disclosed recombinant viral particle. The disclosed method can be used to treat a number of tumors, including ovarian, liver, pancreatic, breast, lung, stomach, and brain tumors.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8A shows activation of apoptosis by VSV-S 36 hr postinfection in MDA-MB 231 cells. FIG. 8B shows effects of different caspase inhibitors (C8I, C9I, and C3I). FIG. 8C shows Cas-3 cleavage in T-47D cells infected by VSV-S versus wt VSV.

FIG. 9A shows Western blot analysis of G expression. FIG. 9B contains Images to show G induced cell syncytia. Nuclei were stained with DAPI.

DETAILED DESCRIPTION

Definitions

Figures 1A, 1B:
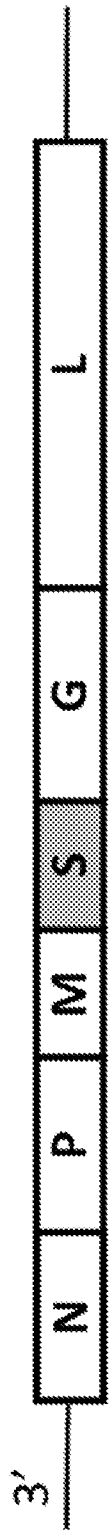
FIG. 1A is a diagram showing the position of Smac insert in the VSV genome that encodes five viral genes originally.
FIG. 1B shows the sequences (SEQ ID NOs:13 and 14) that are used to flank the Smac insert (first Met and stop codons are shown). CT is added at the 3' end as an additional gene junction.
Figure 2:
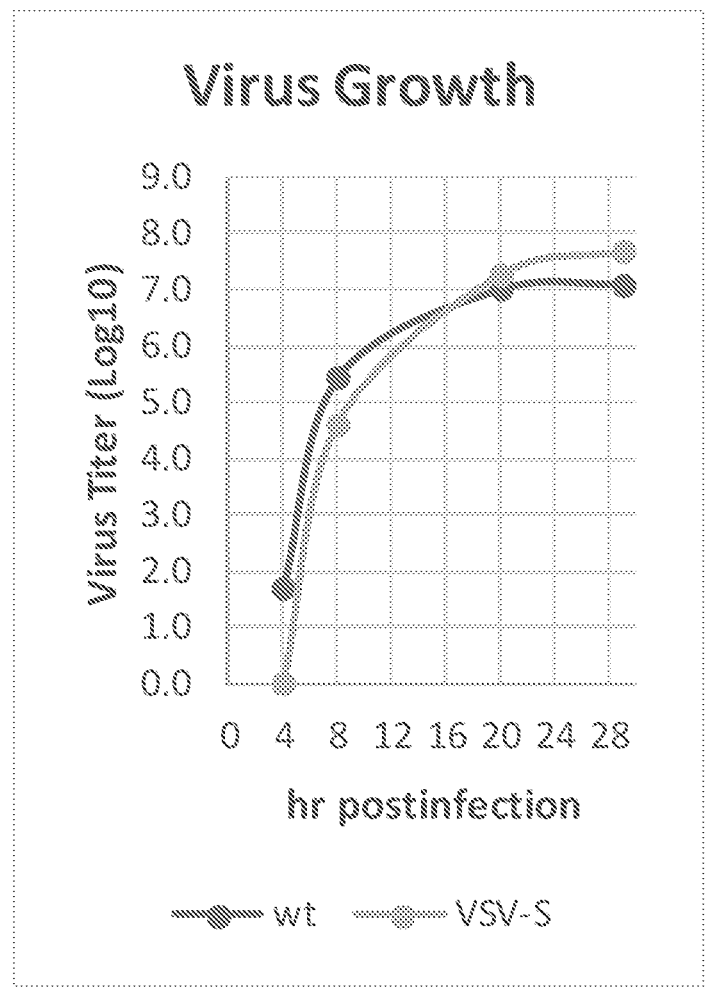
FIG. 2 shows wt VSV and VSV-S grew to similar titers in HeLa cells (MOI=0.01).
Figure 3:
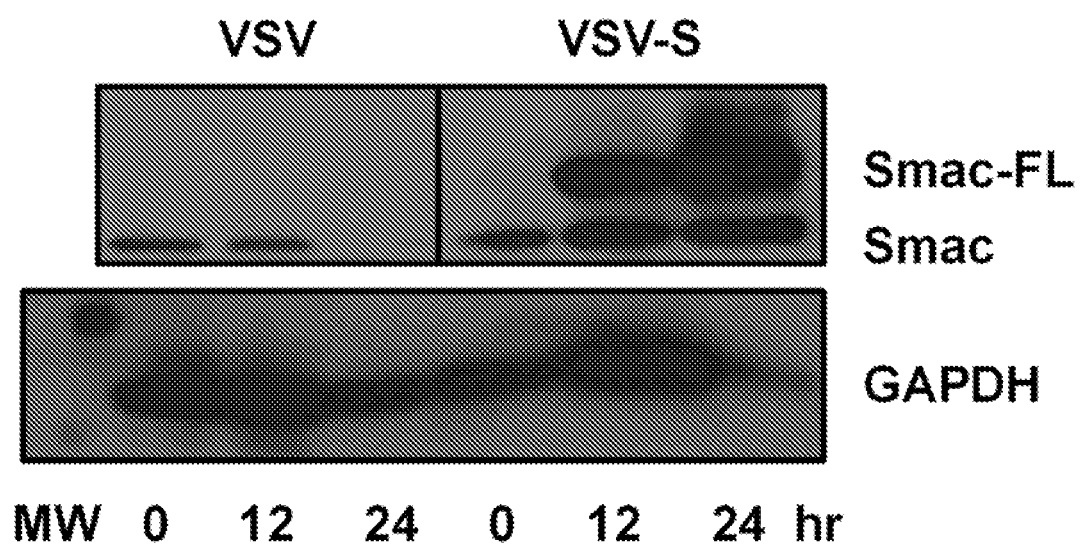
FIG. 3 shows a Western blot analyses of VSV-S and wt VSV infected HeLa cells.
Figure 4A:
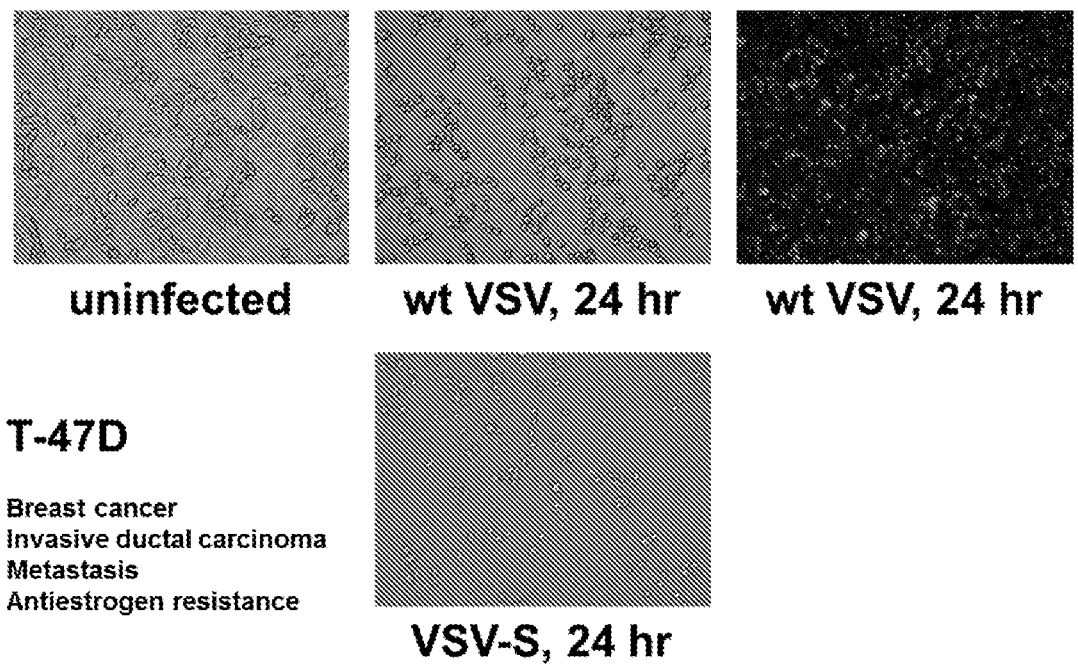
FIG. 4A shows that after 24 hr of infection, most T-47D cells were infected by wt VSV expressing mCherryP (red fluorescence, upper right panel), but did not die.
Figure 4B:
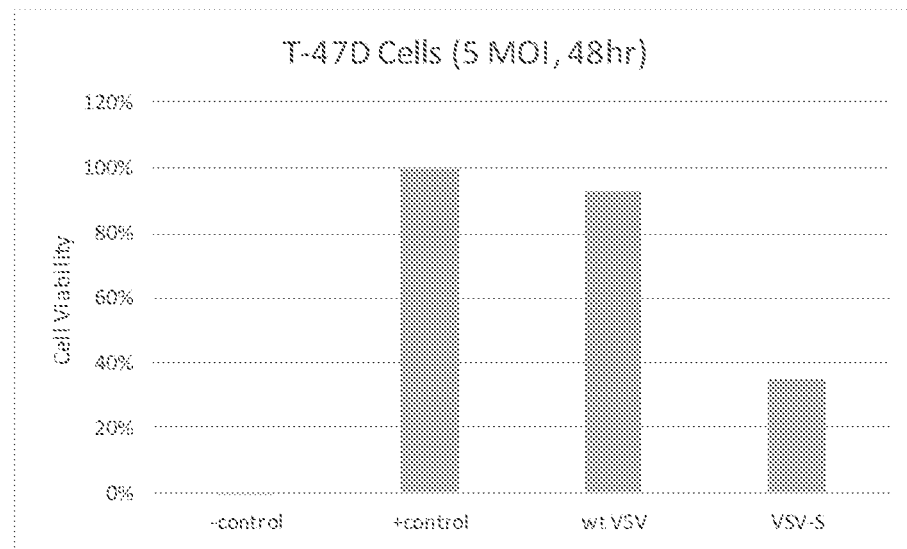
FIG. 4B shows that after 48 hr of infection, more than 60% of T-47D cells were killed by VSV-S, while most cells survived infection by wt VSV.
Figure 5A:
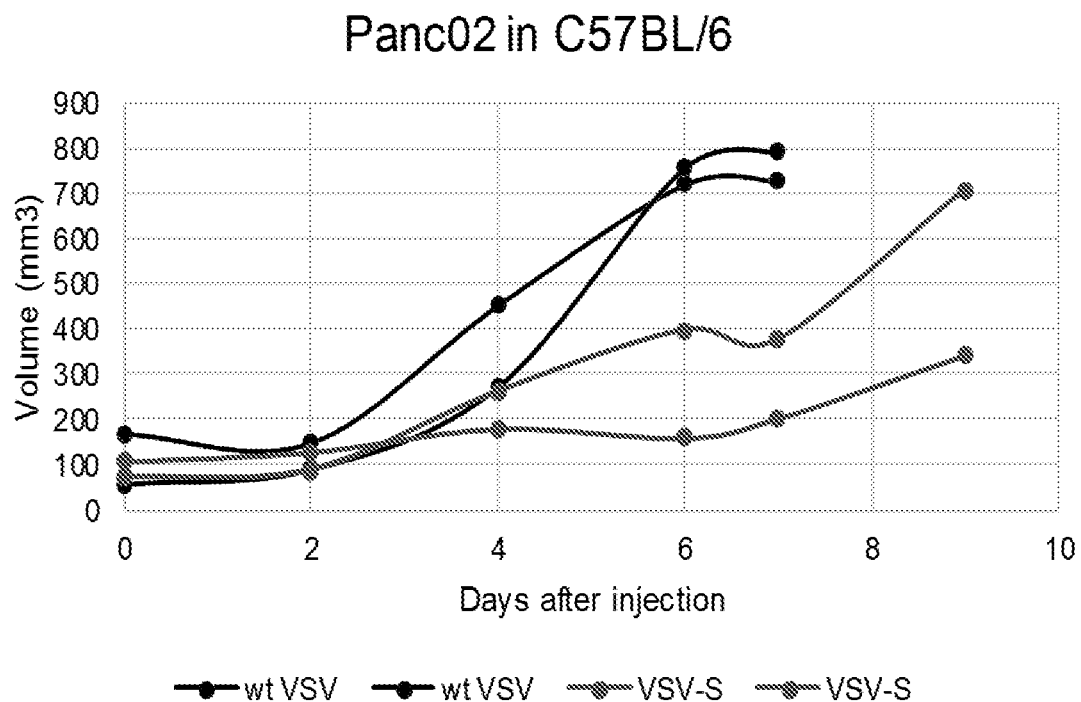
FIG. 5A depicts tumor growth in Panc02 model.
Figure 5B:
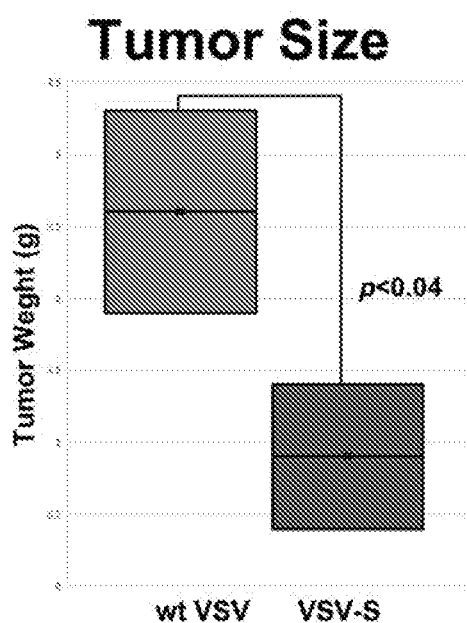
FIG. 5B depicts differences in tumor weights at the end of 9 days.
Figure 6A:
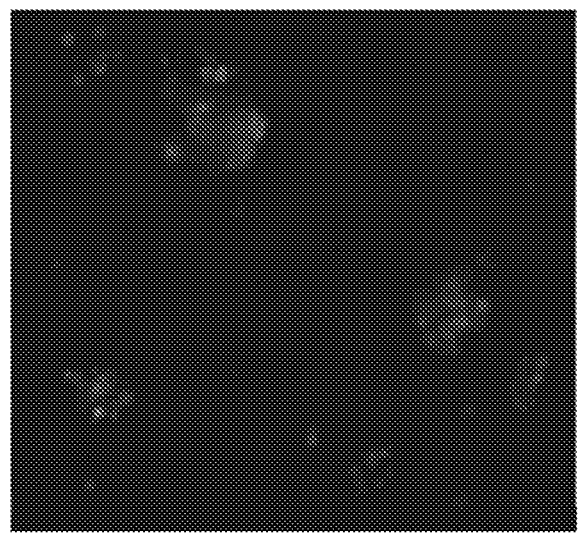
FIG. 6A shows imaging of wt VSV (red) infected tissues of a canine anal sac carcinoma. (B) Cleaved product of PARP (green stain) showed that VSV-S induced enhanced apoptosis in comparison with wt VSV.
Figure 6B:
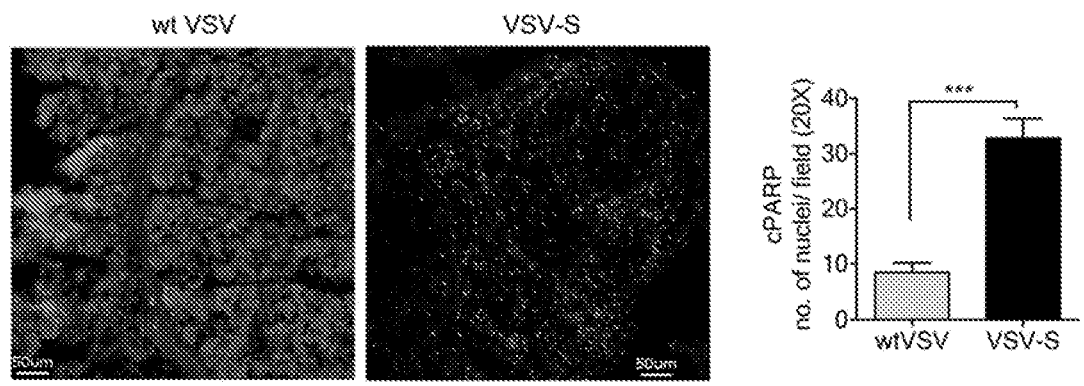
Figure 7A:
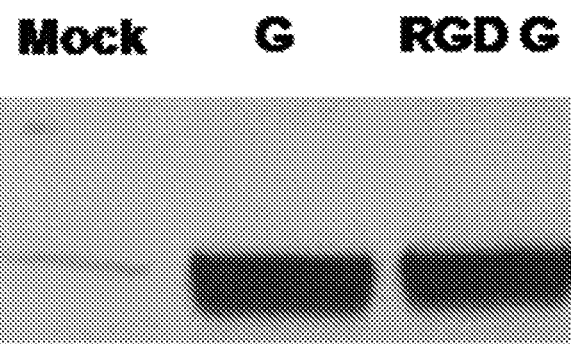
FIG. 7 shows Western blot analyses of Smac in VSV-S and VSV infected HeLa cells.
Figure 7B:
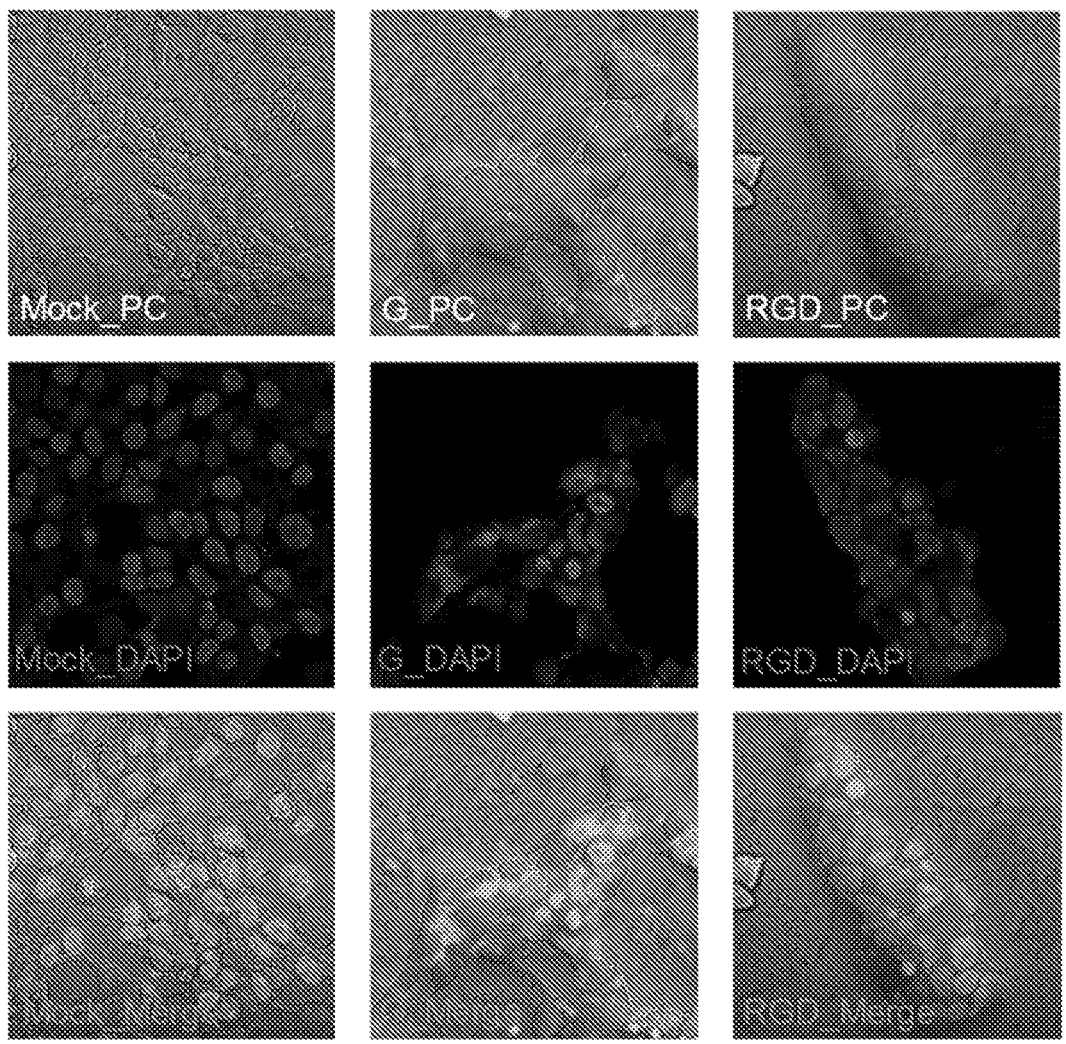

The term "cancer" or "malignant neoplasm" refers to a cell that displays uncontrolled growth, invasion upon adjacent tissues, and often metastasis to other locations of the body.

The term "tumor" refers to an abnormal mass of tissue containing neoplastic cells.

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

The terms "polynucleotide" and "nucleic acid", used interchangeably herein, refer to a polymeric form of nucleotides of any length, either ribonucleotides or deoxyribonucleotides.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, or 99% sequence identity to a reference sequence.

As used herein, the term "recombinant" refers to a virus that has been altered by genetic engineering, by modification or manipulation of the genetic material found in the virus such that it is not identical to the naturally-occurring virus, or a naturally-occurring variant of the virus.

Recombinant Vector

Disclosed herein is a recombinant viral vector comprising a nucleic acid (smac gene) encoding a Second Mitochondria-derived Activator of Caspases (Smac) protein inserted within an RNA virus genome.

Second Mitochondria-Derived Activator of Caspases (Smac)

In some embodiments, the Smac protein encoded by the disclosed viral vector can be any natural, mutant, or fragment of Smac that specifically binds to at least a portion of an Inhibitor of Apoptosis Protein (IAP).

In some embodiments, the Smac protein is a full-length natural protein, such as human Smac. Therefore, in some embodiments, the Smac protein has the amino acid sequence MAALKSWLSRSVTSFFRYRQCLCVPV-VANFKKRCFSELIRPWHKTVTIGFGVTLCAVPI AQKSEPHSLSSEALMRRAVSLVTDSTSTFLSQTTY-ALIEAITEYTKAVYTLTSLYRQYTSL LGKMN-SEEEDEVWQVIIGARAEMTSKHQEY-LKLETTWMTAVGLSEMAAEAAYQTGAD QASITARNHIQLVKLQVEEVHQLSRKAETKLAEA-QIEELRQKTQEEGEERAESEQEAYL RED (SEQ ID NO:1), or a conservative variant thereof that specifically binds IAP.

In other embodiments, the Smac protein lacks a mitochondria-targeting sequence (MTS), e.g., the N-terminal 55 amino acids of full-length Smac. Therefore, in some embodiments, the Smac protein comprises the amino acid sequence AVPIAQKSEPHSLSSEALMRRAVSLVTDST-STFLSQTTYALIEAITEYTKAVYTLTSLYRQ YTSLLGKMNSEEEDEVWQVIIGARAEMTSKHQEY-LKLETTWMTAVGLSEMAAEAAYQT GADQASITARN-HIQLVKLQVEEVHQLSRKAETKLAEA-QIEELRQKTQEEGEERAESEQE AYLRED (SEQ ID NO:2), or a conservative variant thereof that specifically binds IAP.

The consensus IAP-binding motif of Smac is described, for example, in US 2002/0160975 by Alnemri, which is incorporated by reference for the teaching of amino acid sequences that bind an IAP. Therefore, in some embodiments, the Smac protein comprises at least an IAP-binding motif having the amino acid sequence Ala-Xaa$_1$-Xaa$_2$-Xaa$_3$ (SEQ ID NO:3), wherein Xaa$_1$ is Val, Thr, or Ile; Xaa$_2$ is Pro or Ala; and Xaa$_3$ is a non-polar or uncharged polar amino acid residue (e.g. Gly, Ala, Val, Leu, Ile, Pro, Ser, Thr, Cys, Met, Asn, or Gln).

MicroRNA-155

In some cases, the RNA virus genome further comprises a cassette to express microRNA-155. In antitumor immunity, dendritic cells (DCs) capture, process, and present tumor antigens to T cells, initiating a tumoricidal response. However, DCs are often dysfunctional due to their exposure to the tumor microenvironment (TME), leading to tumor escape from immune surveillance. Boosting the expression of microRNA-155 (miR-155) can significantly improve the efficacy of DC-based immunotherapies for breast cancer. In some embodiments, the miR-155 cassette is placed between Smac and G. In some embodiments, the nucleic acid sequence for human miR-155 is (SEQ ID NO: 7)
CTGTTAATGCTAATCGTGATAGGGGTTTTTGCCTCCAACTGACTCCTAC

ATATTAGCATTAACAG.

RNA Virus

The disclosed viruses can in some embodiments, by any natural or modified virus capable of more selective replication in dividing cells (e.g. cancer cell) while replicating less or not in non-dividing cells (e.g. normal cells). As the infected dividing cells are destroyed by lysis, they can in some cases release new infectious virus particles to infect the surrounding dividing cells. A number of viruses including adenovirus, reovirus, measles, herpes simplex, Newcastle disease virus (NDV), vesicular stomatitis virus, poliovirus, coxsackie virus, and vaccinia have now been clinically tested as oncolytic agents.

Some viruses are naturally oncolytic (such as reovirus and the Seneca valley picornavirus) while others are engineered for tumor selectivity by modifying the viral genome. Such modifications include functional deletions in essential viral genes, the use of tumor- or tissue-specific promoters to control the viral gene expression, and tropism modification to redirect virus to the cancer cell surface.

Vesicular Stomatitis Virus (VSV)

In some embodiments, the virus is obtained from a vesicular stomatitis virus (VSV). Recombinant VSV is described, for example, in U.S. Pat. No. 9,428,736 to Russell et al, which is incorporated by reference for the teaching of the methods of making and using VSV vectors and particles.

VSV is a negative-stranded virus, comprising only 5 genes, that preferentially replicates in immortalized and malignant cells, eventually inducing apoptosis. The ability of VSV to reproduce in tumor or malignant cells has been reported to occur, in part, to a defective interferon (IFN) system. Since the IFN system is functional in normal cells, efficient replication of VSV, which is an IFN-sensitive virus, is prevented. Based on in vitro and in vivo observations, it has been demonstrated that VSV effectively replicates in and lyses infected cancer cells, while leaving normal cells relatively unaffected.

The use of VSV as an oncolytic agent has several advantages over other virus delivery systems presently used in tumor therapy such as adenoviruses and retroviruses. Foremost, VSV has no known transforming abilities. VSV is not gene-attenuated, which affects replication and therefore oncolytic anti-tumor activity. The envelope glycoprotein (G) of VSV is highly tropic for a number of cell-types and should be effective at targeting a variety of tissues in vivo. VSV appears to be able to replicate in a wide variety of tumorigenic cells and not, for example, only in cells defective in selective tumor suppressor genes such as p53. VSV is able to potently exert its oncolytic activity in tumors harboring defects in the Ras, Myc and p53 pathways, cellular aberrations that occur in over 90% of all tumors. VSV can be modified through genetic engineering to comprise immunomodulatory and/or suicide cassettes designed to increase the anti-tumor activity of the VSV.

VSV, a member of the Rhabdoviridae family, is a negative-stranded virus that replicates in the cytoplasm of infected cells, does not undergo genetic recombination or reassortment, has no known transforming potential and does not integrate any part of it genome into the host. VSV comprises an about 11 kilobase genome that encodes for five proteins referred to as the nucleocapsid (N), polymerase proteins (L) and (P), surface glycoprotein (G) and a peripheral matrix protein (M). The genome is tightly encased in nucleocapsid (N) protein and also comprises the polymerase proteins (L) and (P). Following infection of the cell, the polymerase proteins initiate the transcription of five subgenomic viral mRNAs, from the negative-sense genome, that encode the viral proteins. The polymerase proteins are also responsible for the replication of the full-length viral genomes that are packaged into progeny virions. The matrix (M) protein binds to the RNA genome/nucleocapsid core (RNP) and also to the glycosylated (G) protein, which extends from the outer surface in an array of spike like projections and is responsible for binding to cell surface receptors and initiating the infectious process.

Following attachment of VSV through the (G) protein to receptor(s) on the host surface, the virus penetrates the host and uncoats to release the RNP particles. The polymerase proteins, which are carried in with the virus, bind to the 3' end of the genome and sequentially synthesize the individual mRNAs encoding N, P, M, G, and L, followed by negative-sense progeny genomes. Newly synthesized N, P and L proteins associate in the cytoplasm and form RNP cores which bind to regions of the plasma membrane rich in both M and G proteins. Viral particles form and budding or release of progeny virus ensues.

The VSV glycosylated (G) protein is responsible for attachment to the host receptor and induction of membrane fusion when the virus is exposed to low pH in the endosome during virus entry. Therefore, in some embodiments, a targeting domain is inserted into the G protein such that the modified G can target the VSV to cancer. The crystal structure of the G protein has been determined for both pre-(neutral pH) and post-fusion (low pH) forms. The site at 191 of NJ strain (190 of IND strain) is permissive for insertion of a six amino acid peptide. Therefore, in some embodiments a targeting domain is inserted at this site of the G protein. The site has Gly at the C-terminal side. Therefore, in some embodiments, a flexible linker is added to the N-terminal side to allow more flexibility.

In some embodiments, the targeting protein domain is any protein sequence that is six amino acids in length or less that can selectively bind a protein displayed on the surface of a cancer cell. RGD is a sequence that binds integrins, such as integrin αvβ3, with a high affinity, and it can be inserted at the 190 site of IND G protein, e.g. with suitable linkers. In some embodiments, the targeting protein domain is any protein sequence that is six amino acids in length or less comprising an RGD amino acid sequence. In some embodiments, the targeting protein domain inserted in the G protein is GRGDS (SEQ ID NO:4).

The VSV G protein can have the amino acid sequence:

```
                                                  (SEQ ID NO: 5)
MKCLLYLAFLFIGVNCKFTIVFPHNRKGNWKNVPSNYHYCPSSSDLNWH

NDLIGTALQVKMPKSHKAIQADGWMCHASKWVTTCDFRWYGPEYITHS

IRSFTPSVEQCKESIEQTKQGTWLNPGFPPQSCGYATVTDAEAAIVQVT

PHHVLVDEYTGEWVDSQFINGKCSNDICPTVHNSTTWHSDYKVKGLCDS

NLISMDITFFSEDGELSSLGKEGTGFRSNYFAYETGDKACKMQYCKHWG

VRLPSGVWFEMADKDLFAAARFPECPEGSSISAPSQTSVDVSLIQDVER

ILDYSLCQETWSKIRAGLPISPVDLSYLAPKNPGTGPVFTIINGTLKYF

ETRYIRVDIAAPILSRMVGMISGTTTERELWDDWAPYEDVEIGPNGVLR

TSSGYKFPLYMIGHGMLDSDLHLSSKAQVFEHPHIQDAASQLPDDETLF

FGDTGLSKNPIEFVEGWFSSWKSSIASFCFIIGLIIGLFLVLRVGIYLC

IKLKHTKKRQIYTDIEMNRLGK.
```

Therefore, in some embodiments, a modified VSV G protein is used that has the amino acid sequence:

```
                                                  (SEQ ID NO: 6)
MKCLLYLAFLFIGVNCKFTIVFPHNRKGNWKNVPSNYHYCPSSSDLNWH

NDLIGTALQVKMPKSHKAIQADGWMCHASKWVTTCDFRWYGPEYITHS

IRSFTPSVEQCKESIEQTKQGTWLNPGFPPQSCGYATVTDAEAAIVQVT

PHHVLVDEYTGEWVDSQFINGKCSNDICPTVHNSTTWHSDYKVKGRGDS

GLCDSNLISMDITFFSEDGELSSLGKEGTGFRSNYFAYETGDKACKMQY

CKHWGVRLPSGVWFEMADKDLFAAARFPECPEGSSISAPSQTSVDVSLI

QDVERILDYSLCQETWSKIRAGLPISPVDLSYLAPKNPGTGPVFTIING

TLKYFETRYIRVDIAAPILSRMVGMISGTTTERELWDDWAPYEDVEIGP

NGVLRTSSGYKFPLYMIGHGMLDSDLHLSSKAQVFEHPHIQDAASQLPD

DETLFFGDTGLSKNPIEFVEGWFSSWKSSIASFCFIIGLIIGLFLVLRV

GIYLCIKLKHTKKRQIYTDIEMNRLGK.
```

Any strain of VSV, including mutants of VSV, can be used in the disclosed vectors. The complete nucleotide and deduced protein sequence of a VSV genome is known and is available as Genbank VSVCG, accession number J02428; NCBI Seq ID 335873; and is published in Rose and Schubert, 1987, in The Viruses: The Rhabdoviruses, Plenum Press, NY pp. 129-166. A complete sequence of a VSV strain is shown in U.S. Pat. No. 6,168,943. VSV New Jersey strain is available from the American Type Culture Collection (ATCC) and has ATCC accession number VR-159. VSV Indiana strain is available from the ATCC and has ATCC accession number VR-1421.

In some embodiments, the recombinant viral vector comprises the nucleic acid sequence

```
                                             (VSV-Smac, SEQ ID NO: 8)
acgaagacaaacaaaccattattatcattaaaaggctcaggagaaactttaacagtaatcaaaatgtctgttacagtcaag agaatcattgacaacacagtcatagttccaaaacttcctgcaaatgaggatccagtggaatacccggcagattacttcaga aaatcaaaggagattcctctttacatcaatactacaaaaagtttgtcagatctaagaggatatgtctaccaaggcctcaaatc cggaaatgtatcaatcatacatgtcaacagctacttgtatggagcattaaaggacatccggggtaagttggataaagattggt
```

-continued

```
caagtttcggaataaacatcgggaaagcaggggatacaatcggaatatttgaccttgtatccttgaaagccctggacggcg
tacttccagatggagtatcggatgcttccagaaccagcgcagatgacaaatggttgcctttgtatctacttggcttatacagagt
gggcagaacacaaatgcctgaatacagaaaaaagctcatggatgggctgacaaatcaatgcaaaatgatcaatgaaca
gtttgaacctcttgtgccagaaggtcgtgacattttttgatgtgtggggaaatgacagtaattacacaaaaattgtcgctgcagtg
gacatgttcttccacatgttcaaaaaacatgaatgtgcctcgttcagatacggaactattgtttccagattcaaagattgtgctgc
attggcaacatttggacacctctgcaaaataaccggaatgtctacagaagatgtaacgacctggatcttgaaccgagaagtt
gcagatgaaatggtccaaatgatgcttccaggccaagaaattgacaaggccgattcatacatgccttatttgatcgactttgg
attgtcttctaagtctccatattcttccgtcaaaaaccctgccttccacttctgggggcaattgacagctcttctgctcagatccac
cagagcaaggaatgcccgacagcctgatgacattgaGTATAcatctcttactacagcaggtttgttgtacgcttatgcagt
aggatcctctgccgacttggcacaacagttttgtgttggagataacaaatacactccagatgatagtaccggaggattgacg
actaatgcaccgccacaaggcagagatgtggtcgaatggctcggatggtttgaagatcaaaacagaaaaccgactcctg
atatgatgcagtatgcgaaaagagcagtcatgtcactgcaaggcctaagagagaagacaattggcaagtatgctaagtca
gaatttgacaaatgaccctataattctcagatcacctattatatattgtgctacatgaaaaaaactaacagatatcatggata
atctcacaaaagttcgtgagtatctcaagtcctactctcgtctagatcaggcggtaggagagatagatgagatcgaagcaca
acgagctgaaaagtccaattatgagttgttccaagaggacggagtggaagagcatactaggccctcttattttcaggcagc
agatgattctgacacagaatctgaaccagaaattgaagacaatcaaggcttgtatgtaccagatccggaagctgagcaag
ttgaaggctttatacagggcctttagatgactatgcagatgaggacgtggatgttgtattcacttcggactggaaacagcctg
agcttgaatccgacgagcatggaaagaccttacggttgacattgccagagggtttaagtggagagcagaaatcccagtgg
cttttgacgattaaagcagtcgttcaaagtgccaaacactggaatctggcagagtgcacatttgaagcatcgggagaaggg
gtcatcataaaaaagcgccagataactccggatgtatataaggtcactccagtgatgaacacacatccgtaccaatcaga
agccgtatcagatgtttggtctctctcaaagacatccatgactttccaacccaagaaagcaagtcttcagcctctcaccatatc
cttggatgaattgttctcatctagaggagaattcatctctgtcggaggtaacggacgaatgtctcataaagaggccatcctgct
cggtctgaggtacaaaaagttgtacaatcaggcgagagtcaaatattctctgtagactatgaaaaaaagtaacagatatca
caatctaagtgttatcccaatccattcatcatgagttccttaaagaagattctcggtctgaaggggaaaggtaagaaatctaa
gaaattagggatcgcaccaccccccttatgaagaggacactagcatggagtatgctccgagcgctccaattgacaaatccta
ttttggagttgacgagatggacacctatgatccgaatcaattaagatatgagaaattcttctttacagtgaaaatgacggttag
atctaatcgtccgttcagaacatactcagatgtggcagccgctgtatcccattgggatcacatgtacatcggaatggcaggg
aaacgtcccttctacaaaatcttggcttttttgggttcttctaatctaaaggccactccagcggtattggcagatcaaggtcaacc
agagtatcacgctcactgcgaaggcagggcttatttgccacataggatggggaagaccccctcccatgctcaatgtaccaga
gcacttcagaagaccattcaatataggtctttacaagggaacgattgagctcacaatgaccatctacgatgatgagtcactg
gaagcagctcctatgatctgggatcatttcaattcttccaaatttttctgatttcagagagaaggccttaatgtttggcctgattgtcg
agaaaaaggcatctggagcgtgggtcctggattctatcagccacttcaaatgagctagtctagcttccagcttctgaacaatc
cccggtttactcagtctctcctaattccagccttttcgaacaactaatatcctgtcttttctATCCCTATGAAAAAAACTA
ACAGATCTCGAGATGgcggctctgaagagttggctgtcgcgcagcgtaacttcattcttcaggtacagacagtgttt
gtgtgttcctgttgtggctaactttaagaagcggtgtttctcagaattgataagaccatggcacaaaactgtgacgattggctttg
gagtaaccctgtgtGCGGTTCCTATTGCACAGAAATCAGAGCCTCATTCCCTTAGTAGTGA
AGCATTGATGAGGAGAGCAGTGTCTTTGGTAACAGATAGCACCTCTACCTTTCTCTC
TCAGACCACATATGCGTTGATTGAAGCTATTACTGAATATACTAAGGCTGTTTATACC
TTAACTTCTCTTTACCGACAATATACAAGTTTACTTGGGAAAATGAATTCAGAGGAGG
AAGATGAAGTGTGGCAGGTGATCATAGGAGCCAGAGCTGAGATGACTTCAAAACAC
CAAGAGTACTTGAAGCTGGAAACCACTTGGATGACTGCAGTTGGTCTTTCAGAGAT
```

```
GGCAGCAGAAGCTGCATATCAAACTGGCGCAGATCAGGCCTCTATAACCGCCAGG

AATCACATTCAGCTGGTGAAACTGCAGGTGGAAGAGGTGCACCAGCTCTCCCGGAA

AGCAGAAACCAAGCTGGCAGAAGCACAGATAGAAGAGCTCCGTCAGAAAACACAG

GAGGAAGGGGAGGAGCGGGCTGAGTCGGAGCAGGAGGCCTACCTGCGTGAGGAT

TGACTCGAGTATATTTTAATTTTTAATTTTTATGAAAAAAACTAacagagatcgatctgtttccttg acaccatgaagtgccttttgtacttagcttttttattcatcggggtgaattgcaagttcaccatagttttccacacaaccgaaaag gaaactggaaaaatgttccttccaattaccattattgcccgtcaagctcagatttaaattggcataatgacttaataggcacag ccttacaagtcaaaatgcccaagagtcacaaggctattcaagcagacggttggatgtgtcatgcttccaaatgggtcactac ttgtgatttccgctggtacggaccggagtatataacacattccatccgatccttcactccatctgtagaacaatgcaaggaaa gcattgaacaaacgaaacaaggaacttggctgaatccaggcttccctcctcaaagttgtggatatgcaactgtgacggatg ctgaagcagcgattgtccaggtgactcctcaccatgtgcttgttgatgaatacacaggagaatgggttgattcacagttcatca acggaaaatgcagcaatgacatatgccccactgtccataactccacaacctggcattccgactataaggtcaaagggctat gtgattctaacctcatttccatggacatcaccttcttctcagaggacggagagctatcatcCCTAGGaaaggagggcaca gggttcagaagtaactactttgcttatgaaactggagacaaggcctgcaaaatgcagtactgcaagcattggggagtcaga ctcccatcaggtgtctggttcgagatggctgataaggatctctttgctgcagccagattccctgaatgcccagaagggtcaag tatctctgctccatctcagacctcagtggatgtaagtctcattcaggacgttgagaggatcttggattattccctctgccaagaa acctggagcaaaatcagagcgggtcttcccatctctccagtggatctcagctatcttgctcctaaaaacccaggaaccggtc ctgtctttaccataatcaatggtaccctaaaatactttgagaccagatacatcagagtcgatattgctgctccaatcctctcaag aatggtcggaatgatcagtggaactaccacagaaagggaactgtgggatgactgggctccatatgaagacgtggaaattg gacccaatggagttctgaggaccagttcaggatataagtttccttatatatgattggacatggtatgttggactccgatcttcat cttagctcaaaggctcaggtgtttgaacatcctcacattcaagacgctgcttcgcagcttcctgatgatgagactttattttttggt gatactgggctatccaaaaatccaatcgagtttgtagaaggttggttcagtagttggaagagctctattgcctctttttgctttatc atagggttaatcattggactattcttggttctccgagttggtatttatctttgcattaaattaaagcacaccaagaaaagacagatt tatacagacatagagatgaaccgacttggaaagtaactcaaatcctgcacaacagattcttcatgtttgaaccaaatcaactt gtgatatcatgctcaaagaggccttaattatattttaattttttaattttttatgaaaaaaactaacagcaatcatggaagtccacgat tttgagaccgacgagttcaatgatttcaatgaagatgactatgccacaagagaattcctgaatcccgatgagcgcatgacgt acttgaatcatgctgattacaatttgaattctcctctaattagtgatgatattgacaatttgatcaggaaattcaattctcttccgatt ccctcgatgtgggatagtaagaactgggatggagttcttgagatgttaacatcatgtcaagccaatcccatctcaacatctca gatgcataaatggatgggaagttggttaatgtctgataatcatgatgccagtcaagggtatagttttttacatgaagtggacaa agaggcagaaataacatttgacgtggtggagaccttcatccgcggctggggcaacaaaccaattgaatacatcaaaaag gaaagatggactgactcattcaaaattctcgcttatttgtgtcaaaagttttttggacttacacaagttgacattaatcttaaatgct gtctctgaggtggaattgctcaacttggcgaggactttcaaaggcaaagtcagaagaagttctcatggaacgaacatatgc aggattagggttcccagcttgggtcctactttttatttcagaaggatgggcttacttcaagaaacttgatattctaatggaccgaa actttctgttaatggtcaaagatgtgattatagggaggatgcaaacggtgctatccatggtatgtagaatagacaacctgttctc agagcaagacatcttctcccttctaaatatctacagaattggagataaaattgtggagaggcagggaaattttttcttatgacttg attaaaatggtggaaccgatatgcaacttgaagctgatgaaattagcaagagaatcaaggcctttagtcccacaattccctc attttgaaaatcatatcaagacttctgttgatgaaggggcaaaaattgaccgaggtataagattcctccatgatcagataatga gtgtgaaaacagtggatctcacactggtgatttatggatcgttcagacattgggtcatccttttatagattattacactggacta gaaaaattacattcccaagtaaccatgaagaaagatattgatgtgtcatatgcaaaagcacttgcaagtgatttagctcggat tgttctatttcaacagttcaatgatcataaaaagtggttcgtgaatggagacttgctccctcatgatcatcccttttaaaagtcatgtt
```

-continued

```
aaagaaaatacatggcccacagctgctcaagttcaagattttggagataaatggcatgaacttccgctgattaaatgttttga aatacccgacttactagacccatcgataatatactctgacaaaagtcattcaatgaataggtcagaggtgttgaaacatgtcc gaatgaatccgaacactcctatccctagtaaaaaggtgttgcagactatgttggacacaaaggctaccaattggaaagaat ttcttaaagagattgatgagaagggcttagatgatgatgatctaattattggtcttaaaggaaaggagagggaactgaagttg gcaggtagattttttctccctaatgtcttggaaattgcgagaatactttgtaattaccgaatatttgataaagactcatttcgtcccta tgtttaaaggcctgacaatggcggacgatctaactgcagtcattaaaaagatgttagattcctcatccggccaaggattgaa gtcatatgaggcaatttgcatagccaatcacattgattacgaaaaatggaataaccaccaaaggaagttatcaaacggccc agtgttccgagttatgggccagttcttaggttatccatccttaatcgagagaactcatgaattttttgagaaaagtcttatatacta caatggaagaccagacttgatgcgtgttcacaacaacacactgatcaattcaacctcccaacgagtttgttggcaaggaca agagggtggactggaaggtctacggcaaaaggatggagtatcctcaatctactggttattcaaagagaggctaaaatca gaaacactgctgtcaaagtcttggcacaaggtgataatcaagttatttgcacacagtataaaacgaagaaatcgagaaac gttgtagaattacagggtgctctcaatcaaatggtttctaataatgagaaaattatgactgcaatcaaaatagggacaggga agttaggacttttgataaatgacgatgagactatgcaatctgcagattacttgaattatggaaaaataccgattttccgtggagt gattagagggttagagaccaagagatggtcacgagtgacttgtgtcaccaatgaccaaatacccacttgtgctaatataatg agctcagtttccacaaatgctctcaccgtagctcattttgctgagaacccaatcaatgccatgatacagtacaattattttggga catttgctagactcttgttgatgatgcatgatcctgctcttcgtcaatcattgtatgaagttcaagataagataccgggcttgcaca gttctactttcaaatacgccatgttgtatttggaccctctccattggaggagtgtcgggcatgtctttgtccaggttttttgattagagcc ttcccagatcccgtaacagaaagtctctcattctggagattcatccatgtacatgctcgaagtgagcatctgaaggagatgag tgcagtatttggaaaccccgagatagccaagtttcgaataactcacatagacaagctagtagaagatccaacctctctgaa catcgctatgggaatgagtccagcgaacttgttaaagactgaggttaaaaaatgcttaatcgaatcaagacaaaccatcag gaaccaggtgattaaggatgcaaccatatatttgtatcatgaagaggatcggctcagaagttcttatggtcaataaatcctct gttccctagattttttaagtgaattcaaatcaggcacttttttgggagtcgcagacgggctcatcagtctatttcaaaattctcgtact attcggaactcctttaagaaaaagtatcatagggaattggatgatttgattgtgaggagtgaggtatcctctttgacacatttag ggaaacttcatttgagaaggggatcatgtaaaatgtggacatgttcagctactcatgctgacacattaagatacaaatcctgg ggccgtacagttattgggacaactgtaccccatccattagaaatgtgggtccacaacatcgaaaagagactccttgtgcac catgtaacacatcagggttcaattatgtttctgtgcattgtccagacgggatccatgacgtctttagttcacggggaccattgcct gcttatctagggtctaaaacatctgaatctacatctattttgcagccttgggaaagggaaagcaaagtcccactgattaaaag agctacacgtcttagagatgctatctcttggtttgttgaacccgactctaaactagcaatgactatactttctaacatccactcttta acaggcgaagaatggaccaaaaggcagcatgggttcaaaagaacagggtctgcccttcataggttttcgacatctcggat gagccatggtgggttcgcatctcagagcactgcagcattgaccaggttgatggcaactacagacaccatgagggatctgg gagatcagaatttcgacttttttattccaagcaacgttgctctatgctcaaattaccaccactgttgcaagagacggatggatca ccagttgtacagatcattatcatattgcctgtaagtcctgtttgagacccatagaagagatcaccctggactcaagtatggact acacgccccagatgtatcccatgtgctgaagacatggaggaatggggaaggttcgtggggacaagagataaaacaga tctatcctttagaagggaattggaagaatttagcacctgctgagcaatcctatcaagtcggcagatgtataggttttctatatgg agacttggcgtatagaaatctactcatgccgaggacagttctctatttcctctatctatacaaggtcgtattagaggtcgaggtt tcttaaaagggttgctagacggattaatgagagcaagttgctgccaagtaatacaccggagaagtctggctcatttgaagag gccggccaacgcagtgtacggaggtttgatttacttgattgataaattgagtgtatcacctccattcctttctcttactagatcagg acctattagagacgaattagaaacgattccccacaagatcccaacctcctatccgacaagcaaccgtgatatgggggtgat tgtcagaaattacttcaaataccaatgccgtctaattgaaaagggaaaatacagatcacattattcacaattatggttattctca gatgtcttatccatagacttcattggaccattctctatttccaccacccctcttgcaaatcctatacaagccatttttatctgggaaag ataagaatgagttgagagagctggcaaatctttcttcattgctaagatcaggagaggggtgggaagacatacatgtgaaatt
```

-continued

```
cttcaccaaggacatattattgtgtccagaggaaatcagacatgcttgcaagttcgggattgctaaggataataataaagac atgagctatccccttggggaagggaatccagagggacaattacaacaatccctgtttattatacgaccaccccttacccaa agatgctagagatgcctccaagaatccaaaatcccctgctgtccggaatcaggttgggccaattaccaactggcgctcatta taaaattcggagtatattacatggaatgggaatccattacagggacttcttgagttgtggagacggctccggagggatgactg ctgcattactacgagaaaatgtgcatagcagaggaatattcaatagtctgttagaattatcagggtcagtcatgcgaggcgc ctctcctgagcccccagtgccctagaaactttaggaggagataaatcgagatgtgtaaatggtgaaacatgtgggaatat ccatctgacttatgtgacccaaggacttgggactatttcctccgactcaaagcaggcttggggcttcaaattgatttaattgtaat ggatatggaagttcgggattcttctactagcctgaaaattgagacgaatgttagaaattatgtgcaccggattttggatgagca aggagttttaatctacaagacttatggaacatatatttgtgagagcgaaaagaatgcagtaacaatccttggtcccatgttcaa gacggtcgacttagttcaaacagaatttagtagttctcaaacgtctgaagtatatatggtatgtaaaggtttgaagaaattaatc gatgaacccaatcccgattggtcttccatcaatgaatcctggaaaaacctgtacgcattccagtcatcagaacaggaatttgc cagagcaaagaaggttagtacatactttaccttgacaggtattccctcccaattcattcctgatcctttgtaaacattgagacta tgctacaaatattcggagtacccacgggtgtgtctcatgcggctgccttaaaatcatctgatagacctgcagatttattgaccat tagcctttttatatggcgattatatcgtattataacatcaatcatatcagagtaggaccgatacctccgaaccccccatcagat ggaattgcacaaaatgtggggatcgctataactggtataagcttttggctgagtttgatggagaaagacattccactatatcaa cagtgtttggcagttatccagcaatcatttccgattaggtgggaggctatttcagtaaaaggaggatacaagcagaagtgga gtactagaggtgatgggctcccaaaagatacccgaatttcagactccttggccccaatcgggaactggatcagatctttgga attggtccgaaaccaagttcgtctaaatccattcaataagatcttgttcaatcagctatgtcgtacagtggataatcatttgaagt ggtcaaatttgcgaaaaaacacaggaatgattgaatggatcaatgggcgaatttcaaaagaagaccggtctatactgatgt tgaagagtgacctacatgaggaaaactcttggagagattaaaaaatcaggaggagactccaaactttaagtatgaaaaa aactttgatccttaagaccctcttgtggttttttattttttatctggttttgtggtcttcgt.
```

In some embodiments, the recombinant viral vector comprises the nucleic acid sequence:

(VSV-SmacΔ55, SEQ ID NO: 9)
```
acgaagacaaacaaaccattattatcattaaaaggctcaggagaaactttaacagtaatcaaaatgtctgttacagtcaag agaatcattgacaacacagtcatagttccaaaacttcctgcaaatgaggatccagtggaatacccggcagattacttcaga aaatcaaaggagattcctctttacatcaatactacaaaaagtttgtcagatctaagaggatatgtctaccaaggcctcaaatc cggaaatgtatcaatcatacatgtcaacagctacttgtatggagcattaaaggacatccggggtaagttggataaagattggt caagtttcggaataaacatcgggaaagcagggggatacaatcggaatatttgaccttgtatccttgaaagccctggacggcg tacttccagatggagtatcggatgcttccagaaccagcgcagatgacaaatggttgcctttgtatctacttggcttatacagagt gggcagaacacaaatgcctgaatacagaaaaaagctcatggatgggctgacaaatcaatgcaaaatgatcaatgaaca gtttgaacctcttgtgccagaaggtcgtgacatttttgatgtgtggggaaatgacagtaattacacaaaaattgtcgctgcagtg gacatgttcttccacatgttcaaaaaacatgaatgtgcctcgttcagatacggaactattgtttccagattcaaagattgtgctgc attggcaacatttggacaccctctgcaaaataaccggaatgtctacagaagatgtaacgacctggatcttgaaccgagaagtt gcagatgaaatggtccaaatgatgcttccaggccaagaaattgacaaggccgattcatacatgccttatttgatcgactttgg attgtcttctaagtctccatattcttccgtcaaaaaccctgccttccacttctgggggcaattgacagctcttctgctcagatccac cagagcaaggaatgcccgacagcctgatgacattgaGTATAcatctcttactacagcaggtttgttgtacgcttatgcagt aggatcctctgccgacttggcacaacagttttgtgttggagataacaaatacactccagatgatagtaccggaggattgacg actaatgcaccgccacaaggcagagatgtggtcgaatggctcggatggtttgaagatcaaaacagaaaaccgactcctg atatgatgcagtatgcgaaaagagcagtcatgtcactgcaaggcctaagagagaagacaattggcaagtatgctaagtca
```

-continued

```
gaatttgacaaatgaccctataattctcagatcacctattatatattatgctacatatgaaaaaaactaacagatatcatggata atctcacaaaagttcgtgagtatctcaagtcctactctcgtctagatcaggcggtaggagagatagatgagatcgaagcaca acgagctgaaaagtccaattatgagttgttccaagaggacggagtggaagagcatactaggccctcttattttcaggcagc agatgattctgacacagaatctgaaccagaaattgaagcaatcaaggcttgtatgtaccagatccggaagctgagcaag ttgaaggctttatacaggggcctttagatgactatgcagatgaggacgtggatgttgtattcacttcggactggaaacagcctg agcttgaatccgacgagcatggaaagaccttacggttgacattgccagagggtttaagtggagagcagaaatcccagtgg cttttgacgattaaagcagtcgttcaaagtgccaaacactggaatctggcagagtgcacatttgaagcatcgggagaaggg gtcatcataaaaaagcgccagataactccggatgtatataaggtcactccagtgatgaacacacatccgtaccaatcaga agccgtatcagatgtttggtctctctcaaagacatccatgactttccaacccaagaaagcaagtcttcagcctctcaccatatc cttggatgaattgttctcatctagaggagaattcatctctgtcggaggtaacggacgaatgtctcataaagaggccatcctgct cggtctgaggtacaaaaagttgtacaatcaggcgagagtcaaatattctctgtagactatgaaaaaagtaacagatatca caatctaagtgttatcccaatccattcatcatgagttccttaaagaagattctcggtctgaaggggaaaggtaagaaatctaa gaaattagggatcgcaccacccccttatgaagaggacactagcatggagtatgctccgagcgctccaattgacaaatccta ttttggagttgacgagatggacacctatgatccgaatcaattaagatatgagaaattcttctttacagtgaaaatgacggttag atctaatcgtccgttcagaacatactcagatgtggcagccgctgtatcccattgggatcacatgtacatcggaatggcaggg aaacgtcccttctacaaaatcttggcttttttgggttcttctaatctaaaggccactccagcggtattggcagatcaaggtcaacc agagtatcacgctcactgcgaaggcagggcttatttgccacataggatggggaagacccctcccatgctcaatgtaccaga gcacttcagaagaccattcaatataggtctttacaagggaacgattgagctcacaatgaccatctacgatgatgagtcactg gaagcagctcctatgatctgggatcatttcaattcttccaaattttctgatttcagagagaaggccttaatgtttggcctgattgtcg agaaaaaggcatctggagcgtgggtcctggattctatcagccacttcaaatgagctagtctagcttccagcttctgaacaatc cccggtttactcagtctctcctaattccagcctttcgaacaactaatatcctgtcttttctATCCCTATGAAAAAACTA

ACAGATCTCGAGATGGCGGTTCCTATTGCACAGAAATCAGAGCCTCATTCCCTTAGT

AGTGAAGCATTGATGAGGAGAGCAGTGTCTTTGGTAACAGATAGCACCTCTACCTTT

CTCTCTCAGACCACATATGCGTTGATTGAAGCTATTACTGAATATACTAAGGCTGTTT

ATACCTTAACTTCTCTTTACCGACAATATACAAGTTTACTTGGGAAAATGAATTCAGA

GGAGGAAGATGAAGTGTGGCAGGTGATCATAGGAGCCAGAGCTGAGATGACTTCA

AAACACCAAGAGTACTTGAAGCTGGAAACCACTTGGATGACTGCAGTTGGTCTTTCA

GAGATGGCAGCAGAAGCTGCATATCAAACTGGCGCAGATCAGGCCTCTATAACCGC

CAGGAATCACATTCAGCTGGTGAAACTGCAGGTGGAAGAGGTGCACCAGCTCTCCC

GGAAAGCAGAAACCAAGCTGGCAGAAGCACAGATAGAAGAGCTCCGTCAGAAAAC

ACAGGAGGAAGGGGAGGAGCGGGCTGAGTCGGAGCAGGAGGCCTACCTGCGTGA

GGATTGACTCGAGTATATTTTAATTTTTAATTTTTATGAAAAAAACTAacagagatcgatctgt ttccttgacaccatgaagtgccttttgtacttagcttttttattcatcggggtgaattgcaagttccaccatagttttttccacacaaccg aaaaggaaactggaaaaatgttccttccaattaccattattgcccgtcaagctcagatttaaattggcataatgacttaatagg cacagccttacaagtcaaaatgcccaagagtcacaaggctattcaagcagacggttggatgtgtcatgcttccaaatgggt cactacttgtgatttccgctggtacggaccggagtatataacacattccatccgatccttcactccatctgtagaacaatgcaa ggaaagcattgaacaaacgaaacaaggaacttggctgaatccaggcttccctcctcaaagttgtggatatgcaactgtgac ggatgctgaagcagcgattgtccaggtgactcctcaccatgtgcttgttgatgaatacacaggagaatgggttgattcacagt tcatcaacggaaaatgcagcaatgacatatgccccactgtccataactccacaacctggcattccgactataaggtcaaag ggctatgtgattctaacctcatttccatggacatcaccttcttctcagaggacggagagctatcatcCCTAGGaaaggag
```

-continued

```
ggcacagggttcagaagtaactactttgcttatgaaactggagacaaggcctgcaaaatgcagtactgcaagcattgggg agtcagactcccatcaggtgtctggttcgagatggctgataaggatctcttttgctgcagccagattccctgaatgcccagaag ggtcaagtatctctgctccatctcagacctcagtggatgtaagtctcattcaggacgttgagaggatcttggattattccctctgc caagaaacctggagcaaaatcagagcgggtcttcccatctctccagtggatctcagctatcttgctcctaaaaacccagga accggtcctgtctttaccataatcaatggtaccctaaaatactttgagaccagatacatcagagtcgatattgctgctccaatcc tctcaagaatggtcggaatgatcagtggaactaccacagaaagggaactgtgggatgactgggctccatatgaagacgtg gaaattggacccaatggagttctgaggaccagttcaggatataagtttcctttatatatgattggacatggtatgttggactccg atcttcatcttagctcaaaggctcaggtgtttgaacatcctcacattcaagacgctgcttcgcagcttcctgatgatgagactttat ttttggtgatactgggctatccaaaaatccaatcgagtttgtagaaggttggttcagtagttggaagagctctattgcctcttttg ctttatcataggttaatcattggactattcttggttctccgagttggtattttatctttgcattaaattaaagcacaccaagaaaaga cagatttatacagacatagagatgaaccgacttggaaagtaactcaaatcctgcacaacagattcttcatgtttgaaccaaat caacttgtgatatcatgctcaaagaggccttaattatattttaattttttaattttttatgaaaaaaactaacagcaatcatggaagtc cacgattttgagaccgacgagttcaatgatttcaatgaagatgactatgccacaagagaattcctgaatcccgatgagcgca tgacgtacttgaatcatgctgattacaatttgaattctcctctaattagtgatgatattgacaatttgatcaggaaattcaattctctt ccgattccctcgatgtgggatagtaagaactgggatggagttcttgagatgttaacatcatgtcaagccaatcccatctcaac atctcagatgcataaatggatgggaagttggttaatgtctgataatcatgatgccagtcaagggtatagttttttacatgaagtg gacaaagaggcagaaataacatttgacgtggtggagaccttcatccgcggctggggcaacaaaccaattgaatacatca aaaaggaaagatggactgactcattcaaaattctcgcttatttgtgtcaaaagttttttggacttacacaagttgacattaatctta aatgctgtctctgaggtggaattgctcaacttggcgaggactttcaaaggcaaagtcagaagaagttctcatggaacgaac atatgcaggattagggttcccagcttgggtcctacttttatttcagaaggatgggcttacttcaagaaacttgatattctaatgga ccgaaactttctgttaatggtcaaagatgtgattatagggaggatgcaaacggtgctatccatggtatgtagaatagacaacc tgttctcagagcaagacatcttctcccttctaaatatctacagaattggagataaaattgtggagaggcagggaaattttttcttat gacttgattaaaatggtggaaccgatatgcaacttgaagctgatgaaattagcaagagaatcaaggcctttagtcccacaat tccctcattttgaaaatcatatcaagacttctgttgatgaaggggcaaaaattgaccgaggtataagattcctccatgatcaga taatgagtgtgaaaacagtggatctcacactggtgatttatggatcgttcagacattgggtcatccttttatagattattacactg gactagaaaaattacattcccaagtaaccatgaagaaagatattgatgtgtcatatgcaaaagcacttgcaagtgatttagct cggattgttctatttcaacagttcaatgatcataaaaagtggttcgtgaatggagacttgctccctcatgatcatcccttttaaaagt catgttaaagaaaatacatggcccacagctgctcaagttcaagattttggagataaatggcatgaacttccgctgattaaatg ttttgaaatacccgacttactagacccatcgataatatactctgacaaaagtcattcaatgaataggtcagaggtgttgaaac atgtccgaatgaatccgaacactcctatccctagtaaaaaggtgttgcagactatgttggacacaaaggctaccaattggaa agaatttcttaaagagattgatgagaagggcttagatgatgatgatctaattattggtcttaaaggaaaggagagggaactg aagttggcaggtagattttctccctaatgtcttggaaattgcgagaatactttgtaattaccgaatatttgataaagactcatttcg tccctatgtttaaaggcctgacaatggcggacgatctaactgcagtcattaaaaagatgttagattcctcatccggccaagga ttgaagtcatatgaggcaatttgcatagccaatcacattgattacgaaaaatggaataaccaccaaaggaagttatcaaac ggcccagtgttccgagttatgggccagttcttaggttatccatccttaatcgagagaactcatgaatttttttgagaaaagtcttat atactacaatggaagaccagacttgatgcgtgttcacaacaacacactgatcaattcaacctcccaacgagtttgttggcaa ggacaagagggtggactggaaggtctacggcaaaaggatggagtatcctcaatctactggttattcaaagagaggctaa aatcagaaacactgctgtcaaagtcttggcacaaggtgataatcaagttatttgcacacagtataaaacgaagaaatcgag aaacgttgtagaattacagggtgctctcaatcaaatggtttctaataatgagaaaattatgactgcaatcaaaataggaca gggaagttaggacttttgataaatgacgatgagactatgcaatctgcagattacttgaattatgaaaaataccgattttccgt ggagtgattagagggttagagaccaagagatggtcacgagtgacttgtgtcaccaatgaccaaatacccacttgtgctaat
```

-continued

```
ataatgagctcagtttccacaaatgctctcaccgtagctcattttgctgagaacccaatcaatgccatgatacagtacaattatt
ttgggacatttgctagactcttgttgatgatgcatgatcctgctcttcgtcaatcattgtatgaagttcaagataagataccgggct
tgcacagttctactttcaaatacgccatgttgtatttggaccctcccattggaggagtgtcgggcatgtctttgtccaggttttttgatt
agagccttcccagatcccgtaacagaaagtctctcattctggagattcatccatgtacatgctcgaagtgagcatctgaagg
agatgagtgcagtatttggaaaccccgagatagccaagtttcgaataactcacatagacaagctagtagaagatccaacct
ctctgaacatcgctatgggaatgagtccagcgaacttgttaaagactgaggttaaaaaatgcttaatcgaatcaagacaaa
ccatcaggaaccaggtgattaaggatgcaaccatatatttgtatcatgaagaggatcggctcagaagtttcttatggtcaata
aatcctctgttccctagatttttaagtgaattcaaatcaggcacttttttgggagtcgcagacgggctcatcagtctatttcaaaatt
ctcgtactattcggaactcctttaagaaaaagtatcatagggaattggatgatttgattgtgaggagtgaggtatcctcttttgaca
catttagggaaacttcatttgagaaggggatcatgtaaaatgtggacatgttcagctactcatgctgacacattaagatacaa
atcctggggccgtacagttattgggacaactgtaccccatccattagaaatgtgggtccacaacatcgaaaagagactcct
tgtgcaccatgtaacacatcagggttcaattatgtttctgtgcattgtccagacgggatccatgacgtctttagttcacggggac
cattgcctgcttatctagggtctaaaacatctgaatctacatctattttgcagccttgggaaagggaaagcaaagtcccactga
ttaaaagagctacacgtcttagagatgctatctcttggtttgttgaacccgactctaaactagcaatgactatactttctaacatc
cactcttttaacaggcgaagaatggaccaaaaggcagcatgggttcaaaagaacagggtctgcccttcataggttttcgaca
tctcggatgagccatggtgggttcgcatctcagagcactgcagcattgaccaggttgatggcaactacagacaccatgagg
gatctgggagatcagaatttcgacttttttattccaagcaacgttgctctatgctcaaattaccaccactgttgcaagagacggat
ggatcaccagttgtacagatcattatcatattgcctgtaagtcctgtttgagacccatagaagagatcaccctggactcaagta
tggactacacgcccccagatgtatcccatgtgctgaagacatggaggaatggggaaggttcgtggggacaagagataaa
acagatctatcctttagaagggaattggaagaatttagcacctgctgagcaatcctatcaagtcggcagatgtataggttttct
atatggagacttggcgtatagaaaatctactcatgccgaggacagttctctatttcctctatctatacaaggtcgtattagaggtc
gaggtttcttaaaagggttgctagacggattaatgagagcaagttgctgccaagtaatacaccggagaagtctggctcatttg
aagaggccggccaacgcagtgtacggaggtttgatttacttgattgataaattgagtgtatcacctccattcctttctcttactag
atcaggacctattagagacgaattagaaacgattccccacaagatcccaacctcctatccgacaagcaaccgtgatatgg
gggtgattgtcagaaattacttcaaataccaatgccgtctaattgaaaagggaaaatacagatcacattattcacaattatggt
tattctcagatgtcttatccatagacttcattggaccattctctatttccaccaccctcttgcaaatcctatacaagccattttatctg
ggaaagataagaatgagttgagagagctggcaaatctttcttcattgctaagatcaggagaggggtgggaagacatacat
gtgaaattcttcaccaaggacatattattgtgtccagaggaaatcagacatgcttgcaagttcgggattgctaaggataataat
aaagacatgagctatccccctggggaagggaatccagagggacaattacaacaatccctgtttattatacgaccacccctt
acccaaagatgctagagatgcctccaagaatccaaaatcccctgctgtccggaatcaggttgggccaattaccaactggc
gctcattataaaattcggagtatattacatggaatgggaatccattacagggacttcttgagttgtggagacggctccggagg
gatgactgctgcattactacgagaaaatgtgcatagcagaggaatattcaatagtctgttagaattatcagggtcagtcatgc
gaggcgcctctcctgagcccccagtgccctagaaactttaggaggagataaatcgagatgtgtaaatggtgaaacatgtt
gggaatatccatctgacttatgtgacccaaggacttgggactatttcctccgactcaaagcaggcttggggcttcaaattgattt
aattgtaatggatatggaagttcgggattcttctactagcctgaaaattgagacgaatgttagaaattatgtgcaccggattttg
gatgagcaaggagttttaatctacaagacttatggaacatatatttgtgagagcgaaaagaatgcagtaacaatccttggtcc
catgttcaagacggtcgacttagttcaaacagaatttagtagttctcaaacgtctgaagtatatatggtatgtaaaggtttgaag
aaattaatcgatgaacccaatcccgattggtcttccatcaatgaatcctggaaaaacctgtacgcattccagtcatcagaaca
ggaatttgccagagcaaagaaggttagtacatactttaccttgacaggtattccctcccaattcattcctgatccttttgtaaaca
ttgagactatgctacaaatattcggagtacccacgggtgtgtctcatgcggctgccttaaaatcatctgatagacctgcagattt
```

-continued

```
attgaccattagccttttttatatggcgattatatcgtattataacatcaatcatatcagagtaggaccgatacctccgaacccccc catcagatggaattgcacaaaatgtggggatcgctataactggtataagcttttggctgagtttgatggagaaagacattcca ctatatcaacagtgtttggcagttatccagcaatcatttccgattaggtggggaggctatttcagtaaaaggaggatacaagca gaagtggagtactagaggtgatgggctcccaaaagatacccgaatttcagactccttggccccaatcgggaactggatca gatctttggaattggtccgaaaccaagttcgtctaaatccattcaataagatcttgttcaatcagctatgtcgtacagtggataat catttgaagtggtcaaatttgcgaaaaaacacaggaatgattgaatggatcaatgggcgaatttcaaaagaagaccggtct atactgatgttgaagagtgacctacatgaggaaaactcttggagagattaaaaaatcaggaggagactccaaactttaagt atgaaaaaaactttgatccttaagaccctcttgtggttttattttttatctggttttgtggtcttcgt.
```

In some embodiments, the recombinant viral vector comprises the nucleic acid sequence:

(VSV-SmacmiR155, SEQ ID NO: 10)
```
acgaagacaaacaaaccattattatcattaaaaggctcaggagaaactttaacagtaatcaaaatgtctgttacagtcaag agaatcattgacaacacagtcatagttccaaaacttcctgcaaatgaggatccagtggaatacccggcagattacttcaga aaatcaaaggagattcctctttacatcaatactacaaaaagtttgtcagatctaagaggatatgtctaccaaggcctcaaatc cggaaatgtatcaatcatacatgtcaacagctacttgtatggagcattaaaggacatccgggtaagttggataaagattggt caagtttcggaataaacatcgggaaagcaggggatacaatcggaatatttgaccttgtatccttgaaagccctggacggcg tacttccagatggagtatcggatgcttccagaaccagcgcagatgacaaatggttgcctttgtatctacttggcttatacagagt gggcagaacacaaatgcctgaatacagaaaaaagctcatggatgggctgacaaatcaatgcaaaatgatcaatgaaca gtttgaacctcttgtgccagaaggtcgtgacattttgatgtgtgggaaatgacagtaattacacaaaaattgtcgctgcagtg gacatgttcttccacatgttcaaaaaacatgaatgtgcctcgttcagatacggaactattgtttccagattcaaagattgtgctgc attggcaacatttggacacctctgcaaaataaccggaatgtctacagaagatgtaacgacctggatcttgaaccgagaagtt gcagatgaaatggtccaaatgatgcttccaggccaagaaattgacaaggccgattcatacatgccttatttgatcgactttgg attgtcttctaagtctccatattcttccgtcaaaaaccctgccttccacttctgggggcaattgacagctcttctgctcagatccac cagagcaaggaatgcccgacagcctgatgacattgaGTATACatctcttactacagcaggtttgttgtacgcttatgcagt aggatcctctgccgacttggcacaacagttttgtgttggagataacaaatacactccagatgatagtaccggaggattgacg actaatgcaccgccacaaggcagagatgtggtcgaatggctcggatggtttgaagatcaaaacagaaaaccgactcctg atatgatgcagtatgcgaaaagagcagtcatgtcactgcaaggcctaagagagaagacaattggcaagtatgctaagtca gaatttgacaaatgaccctataattctcagatcacctattatatattgctacatgaaaaaaactaacagatatcatggata atctcacaaaagttcgtgagtatctcaagtcctactctcgtctagatcaggcggtaggagagatagatgagatcgaagcaca acgagctgaaaagtccaattatgagttgttccaagaggacgagtggaagagcatactaggccctcttattttcaggcagc agatgattctgacacagaatctgaaccagaaattgaagacaatcaaggcttgtatgtaccagatccggaagctgagcaag ttgaaggctttatacaggggcctttagatgactatgcagatgaggacgtggatgttgtattcacttcggactggaaacagcctg agcttgaatccgacgagcatggaaagaccttacggttgacattgccagagggtttaagtggagagcagaaatcccagtgg cttttgacgattaaagcagtcgttcaaagtgccaaacactggaatctggcagagtgcacatttgaagcatcgggagaaggg gtcatcataaaaaagcgccagataactccggatgtatataaggtcactccagtgatgaacacacatccgtaccaatcaga agccgtatcagatgtttggtctctctcaaagacatccatgactttccaacccaagaaagcaagtcttcagcctctcaccatatc cttggatgaattgttctcatctagaggagaattcatctctgtcggaggtaacggacgaatgtctcataaagaggccatcctgct cggtctgaggtacaaaaagttgtacaatcaggcgagagtcaaatattctctgtagactatgaaaaaagtaacagatatca caatctaagtgttatcccaatccattcatcatgagttccttaaagaagattctcggtctgaaggggaaaggtaagaaatctaa gaaattagggatcgcaccaccccccttatgaagaggacactagcatggagtatgctccgagcgctccaattgacaaatccta
```

-continued ttttggagttgacgagatggacacctatgatccgaatcaattaagatatgagaaattcttctttacagtgaaaatgacggttag atctaatcgtccgttcagaacatactcagatgtggcagccgctgtatcccattgggatcacatgtacatcggaatggcaggg aaacgtcccttctacaaaatcttggcttttttgggttcttctaatctaaaggccactccagcggtattggcagatcaaggtcaacc agagtatcacgctcactgcgaaggcagggcttatttgccacataggatggggaagaccccctcccatgctcaatgtaccaga gcacttcagaagaccattcaatataggtctttacaagggaacgattgagctcacaatgaccatctacgatgatgagtcactg gaagcagctcctatgatctgggatcatttcaattcttccaaattttctgatttcagagagaaggccttaatgtttggcctgattgtcg agaaaaaggcatctggagcgtgggtcctggattctatcagccacttcaaatgagctagtctagcttccagcttctgaacaatc cccggtttactcagtctctcctaattccagccttcgaacaactaatatcctgtcttttctATCCCTATGAAAAAAACTA ACAGATCTCGAGATGgcggctctgaagagttggctgtcgcgcagcgtaacttcattcttcaggtacagacagtgttt gtgtgttcctgttgtggctaactttaagaagcggtgtttctcagaattgataagaccatggcacaaaactgtgacgattggctttg gagtaaccctgtgtGCGGTTCCTATTGCACAGAAATCAGAGCCTCATTCCCTTAGTAGTGA

AGCATTGATGAGGAGAGCAGTGTCTTTGGTAACAGATAGCACCTCTACCTTTCTCTC

TCAGACCACATATGCGTTGATTGAAGCTATTACTGAATATACTAAGGCTGTTTATACC

TTAACTTCTCTTTACCGACAATATACAAGTTTACTTGGGAAAATGAATTCAGAGGAGG

AAGATGAAGTGTGGCAGGTGATCATAGGAGCCAGAGCTGAGATGACTTCAAAACAC

CAAGAGTACTTGAAGCTGGAAACCACTTGGATGACTGCAGTTGGTCTTTCAGAGAT

GGCAGCAGAAGCTGCATATCAAACTGGCGCAGATCAGGCCTCTATAACCGCCAGG

AATCACATTCAGCTGGTGAAACTGCAGGTGGAAGAGGTGCACCAGCTCTCCCGGAA

AGCAGAAACCAAGCTGGCAGAAGCACAGATAGAAGAGCTCCGTCAGAAAACACAG

GAGGAAGGGGAGGAGCGGGCTGAGTCGGAGCAGGAGGCCTACCTGCGTGAGGAT

TGACTCGAGTATATTTTAATTTTTAATTTTTATGAAAAAAACTAacagaTCTCGAGctgtta atgctaatcgtgatagggggttttttgcctccaactgactcctacatattagcattaacagCTCGAGTATATTTTAATTT TTAATTTTTATGAAAAAAACTAacagagatcgatctgtttccttgacaccatgaagtgccttttgtacttagcttttttt attcatcggggtgaattgcaagttcaccatagttttttccacacaaccgaaaaggaaactggaaaaatgttccttccaattacc attattgcccgtcaagctcagatttaaattggcataatgacttaataggcacagccttacaagtcaaaatgcccaagagtcac aaggctattcaagcagacggttggatgtgtcatgcttccaaatgggtcactacttgtgatttccgctggtacggaccggagtat ataacacattccatccgatccttcactccatctgtagaacaatgcaaggaaagcattgaacaaacgaaacaaggaacttg gctgaatccaggcttccctcctcaaagttgtggatatgcaactgtgacggatgctgaagcagcgattgtccaggtgactcctc accatgtgcttgttgatgaatacacaggagaatgggttgattcacagttcatcaacggaaaatgcagcaatgacatatgccc cactgtccataactccacaacctggcattccgactataaggtcaaagggctatgtgattctaacctcatttccatggacatcac cttcttctcagaggacggagagctatcatcCCTAGGaaaggagggcacagggttcagaagtaactactttgcttatgaa actggagacaaggcctgcaaaatgcagtactgcaagcattggggagtcagactcccatcaggtgtctggttcgagatggct gataaggatctcttttgctgcagccagattccctgaatgcccagaagggtcaagtatctctgctccatctcagacctcagtggat gtaagtctcattcaggacgttgagaggatcttggattattccctctgccaagaaacctggagcaaaatcagagcgggtcttcc catctctccagtggatctcagctatcttgctcctaaaaacccaggaaccggtcctgtctttaccataatcaatggtaccctaaa atactttgagaccagatacatcagagtcgatattgctgctccaatcctctcaagaatggtcggaatgatcagtggaactacca cagaaagggaactgtgggatgactgggctccatatgaagacgtggaaattggacccaatggagttctgaggaccagttca ggatataagtttcctttatatatgattggacatggtatgttggactccgatcttcatcttagctcaaaggctcaggtgtttgaacatc ctcacattcaagacgctgcttcgcagcttcctgatgatgagactttatttttggtgatactgggctatccaaaaatccaatcgag tttgtagaaggttggttcagtagttggaagagctctattgcctcttttttgctttatcatagggttaatcattggactattcttggttctcc gagttggtatttatctttgcattaaattaaagcacaccaagaaaagacagatttatacagacatagagatgaaccgacttgga -continued aagtaactcaaatcctgcacaacagattcttcatgtttgaaccaaatcaacttgtgatatcatgctcaaagaggccttaattata ttttaattttaattttatgaaaaaaactaacagcaatcatggaagtccacgattttgagaccgacgagttcaatgatttcaatga agatgactatgccacaagagaattcctgaatcccgatgagcgcatgacgtacttgaatcatgctgattacaatttgaattctcc tctaattagtgatgatattgacaatttgatcaggaaattcaattctcttccgattccctcgatgtgggatagtaagaactgggatg gagttcttgagatgttaacatcatgtcaagccaatcccatctcaacatctcagatgcataaatggatgggaagttggttaatgt ctgataatcatgatgccagtcaagggtatagttttttacatgaagtggacaaagaggcagaaataacatttgacgtggtgga gaccttcatccgcggctggggcaacaaaccaattgaatacatcaaaaaggaaagatggactgactcattcaaaattctcg cttatttgtgtcaaaagttttttggacttacacaagttgacattaatcttaaatgctgtctctgaggtggaattgctcaacttggcgag gactttcaaaggcaaagtcagaagaagttctcatggaacgaacatatgcaggattagggttcccagcttgggtcctacttttta tttcagaaggatgggcttacttcaagaaacttgatattctaatggaccgaaactttctgttaatggtcaaagatgtgattatagg gaggatgcaaacggtgctatccatggtatgtagaatagacaacctgttctcagagcaagacatcttctcccttctaaatatcta cagaattggagataaaattgtggagaggcagggaaattttttcttatgacttgattaaaatggtggaaccgatatgcaacttga agctgatgaaattagcaagagaatcaaggcctttagtcccacaattccctcattttgaaaatcatatcaagacttctgttgatga aggggcaaaaattgaccgaggtataagattcctccatgatcagataatgagtgtgaaaacagtggatctcacactggtgatt tatggatcgttcagacattggggtcatccttttatagattattacactggactagaaaaattacattcccaagtaaccatgaaga aagatattgatgtgtcatatgcaaaagcacttgcaagtgatttagctcggattgttctatttcaacagttcaatgatcataaaaag tggttcgtgaatggagacttgctccctcatgatcatccctttaaaagtcatgttaaagaaaatacatggcccacagctgctcaa gttcaagattttggagataaatggcatgaacttccgctgattaaatgttttgaaatacccgacttactagacccatcgataatat actctgacaaaagtcattcaatgaataggtcagaggtgttgaaacatgtccgaatgaatccgaacactcctatccctagtaa aaaggtgttgcagactatgttggacacaaaggctaccaattggaaagaatttcttaaagagattgatgagaagggcttagat gatgatgatctaattattggtcttaaaggaaaggagagggaactgaagttggcaggtagattttttctccctaatgtcttggaaat tgcgagaatactttgtaattaccgaatatttgataaagactcatttcgtccctatgtttaaaggcctgacaatggcggacgatct aactgcagtcattaaaaagatgttagattcctcatccggccaaggattgaagtcatatgaggcaatttgcatagccaatcaca ttgattacgaaaaatggaataaccaccaaaggaagttatcaaacggcccagtgttccgagttatgggccagttcttaggttat ccatccttaatcgagagaactcatgaattttttgagaaaagtcttatatactacaatggaagaccagacttgatgcgtgttcac aacaacacactgatcaattcaacctcccaacgagtttgttggcaaggacaagagggtggactggaaggtctacggcaaa aaggatggagtatcctcaatctactggttattcaaagagaggctaaaatcagaaacactgctgtcaaagtcttggcacaag gtgataatcaagttatttgcacacagtataaaacgaagaaatcgagaaacgttgtagaattacagggtgctctcaatcaaat ggtttctaataatgagaaaattatgactgcaatcaaaatagggacagggaagttaggacttttgataaatgacgatgagact atgcaatctgcagattacttgaattatggaaaaataccgattttccgtggagtgattagagggttagagaccaagagatggtc acgagtgacttgtgtcaccaatgaccaaatacccacttgtgctaatataatgagctcagtttccacaaatgctctcaccgtagc tcattttgctgagaacccaatcaatgccatgatacagtacaattattttgggacatttgctagactcttgttgatgatgcatgatcct gctcttcgtcaatcattgtatgaagttcaagataagataccgggcttgcacagttctactttcaaatacgccatgttgtatttggac ccttccattggaggagtgtcgggcatgtctttgtccaggtttttgattagagccttcccagatcccgtaacagaaagtctctcattc tggagattcatccatgtacatgctcgaagtgagcatctgaaggagatgagtgcagtatttggaaaccccgagatagccaag tttcgaataactcacatagacaagctagtagaagatccaacctctctgaacatcgctatgggaatgagtccagcgaacttgtt aaagactgaggttaaaaaatgcttaatcgaatcaagacaaaccatcaggaaccaggtgattaaggatgcaaccatatatttt gtatcatgaagaggatcggctcagaagtttcttatggtcaataaatcctctgttccctagattttttaagtgaattcaaatcaggca cttttttgggagtcgcagacgggctcatcagtctatttcaaaattctcgtactattcggaactcctttaagaaaaagtatcatagg gaattggatgatttgattgtgaggagtgaggtatcctctttgacacatttagggaaacttcatttgagaaggggatcatgtaaaa -continued

```
tgtggacatgttcagctactcatgctgacacattaagatacaaatcctggggccgtacagttattgggacaactgtaccccat
ccattagaaatgttgggtccacaacatcgaaaagagactccttgtgcaccatgtaacacatcaggttcaattatgtttctgtg
cattgtccagacgggatccatgacgtctttagttcacggggaccattgcctgcttatctagggtctaaaacatctgaatctacat
ctattttgcagccttgggaaagggaaagcaaagtcccactgattaaaagagctacacgtcttagagatgctatctcttggtttg
ttgaacccgactctaaactagcaatgactatactttctaacatccactcttaacaggcgaagaatggaccaaaaggcagc
atgggttcaaaagaacagggtctgcccttcataggttttcgacatctcggatgagccatggtgggttcgcatctcagagcact
gcagcattgaccaggttgatggcaactacagacaccatgagggatctgggagatcagaatttcgacttttattccaagcaa
cgttgctctatgctcaaattaccaccactgttgcaagagacggatggatcaccagttgtacagatcattatcatattgcctgtaa
gtcctgtttgagacccatagaagagatcaccctggactcaagtatggactacacgcccccagatgtatcccatgtgctgaag
acatggaggaatggggaaggttcgtggggacaagagataaaacagatctatcctttagaagggaattggaagaatttagc
acctgctgagcaatcctatcaagtcggcagatgtataggttttctatatggagacttggcgtatagaaaatctactcatgccga
ggacagttctctatttcctctatctatacaaggtcgtattagaggtcgaggtttcttaaaagggttgctagacggattaatgagag
caagttgctgccaagtaatacaccggagaagtctggctcatttgaagaggccggccaacgcagtgtacggaggtttgattta
cttgattgataaattgagtgtatcacctccattcctttctcttactagatcaggacctattagagacgaattagaaacgattcccc
acaagatcccaacctcctatccgacaagcaaccgtgatatgggggtgattgtcagaaattacttcaaataccaatgccgtct
aattgaaaagggaaaatacagatcacattattcacaattatggttattctcagatgtcttatccatagacttcattggaccattct
ctatttccaccaccctcttgcaaatcctatacaagccattttatctgggaaagataagaatgagttgagagagctggcaaatc
tttcttcattgctaagatcaggagaggggtgggaagacatacatgtgaaattcttcaccaaggacatattattgtgtccagagg
aaatcagacatgcttgcaagttcgggattgctaaggataataataaagacatgagctatccccttggggaagggaatcca
gagggacaattacaacaatccctgtttattatacgaccaccccttacccaaagatgctagagatgcctccaagaatccaaa
atcccctgctgtccggaatcaggttgggccaattaccaactggcgctcattataaaattcggagtatattacatggaatggga
atccattacagggacttcttgagttgtggagacggctccggagggatgactgctgcattactacgagaaaatgtgcatagca
gaggaatattcaatagtctgttagaattatcagggtcagtcatgcgaggcgcctctcctgagccccccagtgccctagaaact
ttaggaggagataaatcgagatgtgtaaatggtgaaacatgttgggaatatccatctgacttatgtgacccaaggacttggg
actatttcctccgactcaaagcaggcttgggcttcaaattgatttaattgtaatggatatggaagttcgggattcttctactagcc
tgaaaattgagacgaatgttagaaattatgtgcaccggattttggatgagcaaggagttttaatctacaagacttatggaacat
atatttgtgagagcgaaaagaatgcagtaacaatccttggtcccatgttcaagacggtcgacttagttcaaacagaatttagt
agttctcaaacgtctgaagtatatatggtatgtaaaggtttgaagaaattaatcgatgaacccaatcccgattggtcttccatca
atgaatcctggaaaaacctgtacgcattccagtcatcagaacaggaatttgccagagcaaagaaggttagtacatactttac
cttgacaggtattccctcccaattcattcctgatccttttgtaaacattgagactatgctacaaatattcggagtacccacgggtgt
gtctcatgcggctgccttaaaatcatctgatagacctgcagatttattgaccattagccttttttatatggcgattatatcgtattata
acatcaatcatatcagagtaggaccgatacctccgaaccccccatcagatggaattgcacaaaatgtggggatcgctata
actggtataagcttttggctgagtttgatggagaaagacattccactatatcaacagtgtttggcagttatccagcaatcatttcc
gattaggtgggaggctatttcagtaaaaggaggatacaagcagaagtggagtactagaggtgatgggctcccaaaagat
acccgaatttcagactccttggccccaatcgggaactggatcagatcttggaattggtccgaaaccaagttcgtctaaatcc
attcaataagatcttgttcaatcagctatgtcgtacagtggataatcatttgaagtggtcaaatttgcgaaaaaacacaggaat
gattgaatggatcaatgggcgaatttcaaaagaagaccggtctatactgatgttgaagagtgacctacatgaggaaaactct
tggagagattaaaaaatcaggaggagactccaaactttaagtatgaaaaaaactttgatccttaagaccctcttgtggttttat
tttttatctggttttgtggtcttcgt.
```

In some embodiments, the recombinant viral vector comprises the nucleic acid sequence:

(VSV-SmacΔ55-miR155, SEQ ID NO: 11)

acgaagacaaacaaaccattattatcattaaaaggctcaggagaaactttaacagtaatcaaaatgtctgttacagtcaag agaatcattgacaacacagtcatagttccaaaacttcctgcaaatgaggatccagtggaatacccggcagattacttcaga aaatcaaaggagattcctctttacatcaatactacaaaaagtttgtcagatctaagaggatatgtctaccaaggcctcaaatc cggaaatgtatcaatcatacatgtcaacagctacttgtatggagcattaaaggacatccggggtaagttggataaagattggt caagtttcggaataaacatcgggaaagcaggggatacaatcggaatatttgaccttgtatccttgaaagccctggacggcg tacttccagatggagtatcggatgcttccagaaccagcgcagatgacaaatggttgcctttgtatctacttggcttatacagagt gggcagaacacaaatgcctgaatacagaaaaaagctcatggatgggctgacaaatcaatgcaaaatgatcaatgaaca gtttgaacctcttgtgccagaaggtcgtgacattttgatgtgtggggaaatgacagtaattacacaaaaattgtcgctgcagtg gacatgttcttccacatgttcaaaaaacatgaatgtgcctcgttcagatacggaactattgtttccagattcaaagattgtgctgc attggcaacatttggacacctctgcaaaataaccggaatgtctacagaagatgtaacgacctggatcttgaaccgagaagtt gcagatgaaatggtccaaatgatgcttccaggccaagaaattgacaaggccgattcatacatgccttatttgatcgactttgg attgtcttctaagtctccatattcttccgtcaaaaaccctgccttccacttctgggggcaattgacagctcttctgctcagatccac cagagcaaggaatgcccgacagcctgatgacattgaGTATACatctcttactacagcaggtttgttgtacgcttatgcagt aggatcctctgccgacttggcacaacagttttgtgttggagataacaaatacactccagatgatagtaccggaggattgacg actaatgcaccgccacaaggcagagatgtggtcgaatggctcggatggtttgaagatcaaaacagaaaaccgactcctg atatgatgcagtatgcgaaaagagcagtcatgtcactgcaaggcctaagagagaagacaattggcaagtatgctaagtca gaatttgacaaatgaccctataattctcagatcacctattatatattatgctacatatgaaaaaaactaacagatatcatggata atctcacaaaagttcgtgagtatctcaagtcctactctcgtctagatcaggcggtaggagagatagatgagatcgaagcaca acgagctgaaaagtccaattatgagttgttccaagaggacggagtggaagagcatactaggccctcttattttcaggcagc agatgattctgacacagaatctgaaccagaaattgaagacaatcaaggcttgtatgtaccagatccggaagctgagcaag ttgaaggctttatacaggggcctttagatgactatgcagatgaggacgtggatgttgtattcacttcggactggaaacagcctg agcttgaatccgacgagcatggaaagaccttacggttgacattgccagagggtttaagtggagagcagaaatcccagtgg cttttgacgattaaagcagtcgttcaaagtgccaaacactggaatctggcagagtgcacatttgaagcatcgggagaaggg gtcatcataaaaaagcgccagataactccggatgtatataaggtcactccagtgatgaacacacatccgtaccaatcaga agccgtatcagatgtttggtctctctcaaagacatccatgactttccaacccaagaaagcaagtcttcagcctctcaccatatc cttggatgaattgttctcatctagaggagaattcatctctgtcggaggtaacggacgaatgtctcataaagaggccatcctgct cggtctgaggtacaaaaagttgtacaatcaggcgagagtcaaatattctctgtagactatgaaaaaaagtaacagatatca caatctaagtgttatcccaatccattcatcatgagttccttaaagaagattctcggtctgaaggggaaaggtaagaaatctaa gaaattagggatcgcaccacccccttatgaagaggacactagcatggagtatgctccgagcgctccaattgacaaatccta ttttggagttgacgagatggacacctatgatccgaatcaattaagatatgagaaattcttctttacagtgaaaatgacggttag atctaatcgtccgttcagaacatactcagatgtggcagccgctgtatcccattgggatcacatgtacatcggaatggcaggg aaacgtcccttctacaaaatcttggctttttgggttcttctaatctaaaggccactccagcggtattggcagatcaaggtcaacc agagtatcacgctcactgcgaaggcagggcttatttgccacataggatggggaagacccctcccatgctcaatgtaccaga gcacttcagaagaccattcaatataggtctttacaagggaacgattgagctcacaatgaccatctacgatgatgagtcactg gaagcagctcctatgatctgggatcatttcaattcttccaaattttctgatttcagagagaaggccttaatgtttggcctgattgtcg agaaaaaggcatctggagcgtgggtcctggattctatcagccacttcaaatgagctagtctagcttccagcttctgaacaatc cccggtttactcagtctctcctaattccagcctttcgaacaactaatatcctgtcttttctATCCCTATGAAAAAAACTA

ACAGATCTCGAGATGGCGGTTCCTATTGCACAGAAATCAGAGCCTCATTCCCTTAGT

AGTGAAGCATTGATGAGGAGAGCAGTGTCTTTGGTAACAGATAGCACCTCTACCTTT

-continued

```
CTCTCTCAGACCACATATGCGTTGATTGAAGCTATTACTGAATATACTAAGGCTGTTT
ATACCTTAACTTCTCTTTACCGACAATATACAAGTTTACTTGGGAAAATGAATTCAGA
GGAGGAAGATGAAGTGTGGCAGGTGATCATAGGAGCCAGAGCTGAGATGACTTCA
AAACACCAAGAGTACTTGAAGCTGGAAACCACTTGGATGACTGCAGTTGGTCTTTCA
GAGATGGCAGCAGAAGCTGCATATCAAACTGGCGCAGATCAGGCCTCTATAACCGC
CAGGAATCACATTCAGCTGGTGAAACTGCAGGTGGAAGAGGTGCACCAGCTCTCCC
GGAAAGCAGAAACCAAGCTGGCAGAAGCACAGATAGAAGAGCTCCGTCAGAAAAC
ACAGGAGGAAGGGGAGGAGCGGGCTGAGTCGGAGCAGGAGGCCTACCTGCGTGA
GGATTGACTCGAGTATATTTTAATTTTTAATTTTTATGAAAAAAACTAacagaTCTCGAG
ctgttaatgctaatcgtgatagggggttttgcctccaactgactcctacatattagcattaacagCTCGAGTATATTTTA
ATTTTTAATTTTTATGAAAAAAACTAacagagatcgatctgtttccttgacaccatgaagtgccttttgtacttag
cttttttattcatcggggtgaattgcaagttcaccatagttttccacacaaccgaaaaggaaactggaaaaatgttccttccaat
taccattattgcccgtcaagctcagatttaaattggcataatgacttaataggcacagccttacaagtcaaaatgcccaagag
tcacaaggctattcaagcagacggttggatgtgtcatgcttccaaatgggtcactacttgtgatttccgctggtacggaccgga
gtatataacacattccatccgatccttcactccatctgtagaacaatgcaaggaaagcattgaacaaacgaaacaaggaa
cttggctgaatccaggcttccctcctcaaagttgtggatatgcaactgtgacggatgctgaagcagcgattgtccaggtgact
cctcaccatgtgcttgttgatgaatacacaggagaatgggttgattcacagttcatcaacggaaaatgcagcaatgacatat
gccccactgtccataactccacaacctggcattccgactataaggtcaaagggctatgtgattctaacctcatttccatggac
atcaccttcttctcagaggacggagagctatcatcCCTAGGaaaggagggcacagggttcagaagtaactactttgctt
atgaaactggagacaaggcctgcaaaatgcagtactgcaagcattggggagtcagactcccatcaggtgtctggttcgag
atggctgataaggatctctttgctgcagccagattccctgaatgcccagaagggtcaagtatctctgctccatctcagacctca
gtggatgtaagtctcattcaggacgttgagaggatcttggattattccctctgccaagaaacctggagcaaaatcagagcgg
gtcttcccatctctccagtggatctcagctatcttgctcctaaaaacccaggaaccggtcctgtctttaccataatcaatggtacc
ctaaaatactttgagaccagatacatcagagtcgatattgctgctccaatcctctcaagaatggtcggaatgatcagtggaac
taccacagaaagggaactgtgggatgactgggctccatatgaagacgtggaaattggacccaatggagttctgaggacc
agttcaggatataagtttcctttatatatgattggacatggtatgttggactccgatcttcatcttagctcaaaggctcaggtgtttg
aacatcctcacattcaagacgctgcttcgcagcttcctgatgatgagactttattttttggtgatactgggctatccaaaaatcca
atcgagtttgtagaaggttggttcagtagttggaagagctctattgcctcttttttgctttatcatagggttaatcattggactattcttg
gttctccgagttggtatttatctttgcattaaattaaagcacaccaagaaaagacagatttatacagacatagagatgaaccg
acttggaaagtaactcaaatcctgcacaacagattcttcatgtttgaaccaaatcaacttgtgatatcatgctcaaagaggcct
taattatattttaattttttaattttatgaaaaaaactaacagcaatcatggaagtccacgattttgagaccgacgagttcaatgat
ttcaatgaagatgactatgccacaagagaattcctgaatcccgatgagcgcatgacgtacttgaatcatgctgattacaatttg
aattctcctctaattagtgatgatattgacaatttgatcaggaaattcaattctcttccgattccctcgatgtgggatagtaagaac
tgggatggagttcttgagatgttaacatcatgtcaagccaatcccatctcaacatctcagatgcataaatggatgggaagttg
gttaatgtctgataatcatgatgccagtcaagggtatagtttttttacatgaagtggacaaagaggcagaaataacatttgacgt
ggtggagaccttcatccgcggctggggcaacaaaccaattgaatacatcaaaaaggaaagatggactgactcattcaaa
attctcgcttatttgtgtcaaaagttttggacttacacaagttgacattaatcttaaatgctgtctctgaggtggaattgctcaactt
ggcgaggactttcaaaggcaaagtcagaagaagttctcatggaacgaacatatgcaggattaggggttcccagcttgggtc
ctactttttatttcagaaggatgggcttacttcaagaaacttgatattctaatggaccgaaactttctgttaatggtcaaagatgtga
ttatagggaggatgcaaacggtgctatccatggtatgtagaatagacaacctgttctcagagcaagacatcttctcccttctaa
```

-continued

```
atatctacagaattggagataaaattgtggagaggcagggaaattttctttatgacttgattaaaatggtggaaccgatatgca acttgaagctgatgaaattagcaagagaatcaaggcctttagtcccacaattccctcattttgaaaatcatatcaagacttctgt tgatgaaggggcaaaaattgaccgaggtataagattcctccatgatcagataatgagtgtgaaaacagtggatctcacact ggtgatttatggatcgttcagacattggggtcatcctttttatagattattacactggactagaaaaattacattcccaagtaacca tgaagaaagatattgatgtgtcatatgcaaaagcacttgcaagtgatttagctcggattgttctatttcaacagttcaatgatcat aaaaagtggttcgtgaatggagacttgctccctcatgatcatccctttaaaagtcatgttaaagaaaatacatggcccacagc tgctcaagttcaagattttggagataaatggcatgaacttccgctgattaaatgttttgaaatacccgacttactagacccatcg ataatatactctgacaaaagtcattcaatgaataggtcagaggtgttgaaacatgtccgaatgaatccgaacactcctatccc tagtaaaaaggtgttgcagactatgttggacacaaaggctaccaattggaaagaatttcttaaagagattgatgagaaggg cttagatgatgatgatctaattattggtcttaaaggaaaggagagggaactgaagttggcaggtagattttctccctaatgtctt ggaaattgcgagaatactttgtaattaccgaatatttgataaagactcatttcgtccctatgtttaaaggcctgacaatggcgga cgatctaactgcagtcattaaaaagatgttagattcctcatccggccaaggattgaagtcatatgaggcaatttgcatagcca atcacattgattacgaaaaatggaataaccaccaaaggaagttatcaaacggcccagtgttccgagttatgggccagttctt aggttatccatccttaatcgagagaactcatgaattttttgagaaaagtcttatatactacaatggaagaccagacttgatgcgt gttcacaacaacacactgatcaattcaacctcccaacgagtttgttggcaaggacaagagggtggactggaaggtctacg gcaaaaaggatggagtatcctcaatctactggttattcaaagagaggctaaaatcagaaacactgctgtcaaagtcttggc acaaggtgataatcaagttatttgcacacagtataaaacgaagaaatcgagaaacgttgtagaattacagggtgctctcaat caaatggtttctaataatgagaaaattatgactgcaatcaaaatagggacagggaagttaggacttttgataaatgacgatg agactatgcaatctgcagattacttgaattatggaaaaataccgattttccgtggagtgattagagggttagagaccaagag atggtcacgagtgacttgtgtcaccaatgaccaaatacccacttgtgctaatataatgagctcagtttccacaaatgctctcac cgtagctcattttgctgagaacccaatcaatgccatgatacagtacaattattttgggacatttgctagactcttgttgatgatgca tgatcctgctcttcgtcaatcattgtatgaagttcaagataagataccgggcttgcacagttctactttcaaatacgccatgttgta tttggacccttccattggaggagtgtcgggcatgtctttgtccaggtttttgattagagccttcccagatcccgtaacagaaagtc tctcattctggagattcatccatgtacatgctcgaagtgagcatctgaaggagatgagtgcagtatttggaaaccccgagata gccaagtttcgaataactcacatagacaagctagtagaagatccaacctctctgaacatcgctatgggaatgagtccagcg aacttgttaaagactgaggttaaaaaatgcttaatcgaatcaagacaaaccatcaggaaccaggtgattaaggatgcaac catatatttgtatcatgaagaggatcggctcagaagtttcttatggtcaataaatcctctgttccctagatttttaagtgaattcaaa tcaggcacttttttgggagtcgcagacgggctcatcagtctatttcaaaattctcgtactattcggaactccttttaagaaaaagta tcatagggaattggatgatttgattgtgaggagtgaggtatcctcttttgacacatttagggaaacttcatttgagaaggggatca tgtaaaatgtggacatgttcagctactcatgctgacacattaagatacaaatcctggggccgtacagttattgggacaactgt accccatccattagaaatgtgggtccacaacatcgaaaagagactccttgtgcaccatgtaacacatcagggttcaattat gtttctgtgcattgtccagacgggatccatgacgtctttagttcacggggaccattgcctgcttatctagggtctaaaacatctga atctacatctattttgcagccttgggaaagggaaagcaaagtcccactgattaaaagagctacacgtcttagagatgctatct cttggtttgttgaacccgactctaaactagcaatgactatactttctaacatccactctttaacaggcgaagaatggaccaaaa ggcagcatgggttcaaaagaacagggtctgcccttcataggttttcgacatctcggatgagccatggtgggttcgcatctcag agcactgcagcattgaccaggttgatggcaactacagacaccatgagggatctgggagatcagaatttcgacttttttattcca agcaacgttgctctatgctcaaattaccaccactgttgcaagagacggatggatcaccagttgtacagatcattatcatattgc ctgtaagtcctgtttgagacccatagaagagatcaccctggactcaagtatggactacacgccccagatgtatcccatgtg ctgaagacatggaggaatgggaaggttcgtggggacaagagataaaacagatctatcctttagaagggaattggaaga atttagcacctgctgagcaatcctatcaagtcggcagatgtataggttttctatatggagacttggcgtatagaaaatctactca tgccgaggacagttctctatttcctctatctatacaaggtcgtattagaggtcgaggtttcttaaaagggttgctagacggattaa
```

-continued

```
tgagagcaagttgctgccaagtaatacaccggagaagtctggctcatttgaagaggccggccaacgcagtgtacggaggt ttgatttacttgattgataaattgagtgtatcacctccattcctttctcttactagatcaggacctattagagacgaattagaaacg attccccacaagatcccaacctcctatccgacaagcaaccgtgatatgggggtgattgtcagaaattacttcaaataccaat gccgtctaattgaaaagggaaaatacagatcacattattcacaattatggttattctcagatgtcttatccatagacttcattgga ccattctctatttccaccaccctcttgcaaatcctatacaagccatttttatctgggaaagataagaatgagttgagagagctgg caaatctttcttcattgctaagatcaggagaggggtgggaagacatacatgtgaaattcttcaccaaggacatattattgtgtc cagaggaaatcagacatgcttgcaagttcgggattgctaaggataataataaagacatgagctatccccttggggaagg gaatccagagggacaattacaacaatccctgtttattatacgaccaccccttacccaaagatgctagagatgcctccaaga atccaaaatcccctgctgtccggaatcaggttgggccaattaccaactggcgctcattataaaattcggagtatattcatgg aatgggaatccattacagggacttcttgagttgtggagacggctccggagggatgactgctgcattactacgagaaatgtg catagcagaggaatattcaatagtctgttagaattatcagggtcagtcatgcgaggcgcctctcctgagcccccagtgccct agaaactttaggaggagataaatcgagatgtgtaaatggtgaaacatgttgggaatatccatctgacttatgtgacccaagg acttgggactatttcctccgactcaaagcaggcttggggcttcaaattgatttaattgtaatggatatggaagttcgggattcttct actagcctgaaaattgagacgaatgttagaaattatgtgcaccggattttggatgagcaaggagttttaatctacaagacttat ggaacatatatttgtgagagcgaaaagaatgcagtaacaatccttggtcccatgttcaagacggtcgacttagttcaaacag aatttagtagttctcaaacgtctgaagtatatatggtatgtaaaggtttgaagaaattaatcgatgaacccaatcccgattggtct tccatcaatgaatcctggaaaaacctgtacgcattccagtcatcagaacaggaatttgccagagcaaagaaggttagtaca tactttaccttgacaggtattccctcccaattcattcctgatcctttgtaaacattgagactatgctacaaatattcggagtaccca cgggtgtgtctcatgcggctgccttaaaatcatctgatagacctgcagatttattgaccattagccttttttatatggcgattatatc gtattataacatcaatcatatcagagtaggaccgatacctccgaaccccccatcagatggaattgcacaaaatgtgggat cgctataactggtataagcttttggctgagtttgatggagaaagacattccactatatcaacagtgtttggcagttatccagcaa tcatttccgattaggtgggaggctatttcagtaaaaggaggatacaagcagaagtggagtactagaggtgatgggctccca aaagatacccgaatttcagactccttggccccaatcgggaactggatcagatcttttggaattggtccgaaaccaagttcgtct aaatccattcaataagatcttgttcaatcagctatgtcgtacagtggataatcatttgaagtggtcaaatttgcgaaaaaacac aggaatgattgaatggatcaatgggcgaatttcaaaagaagaccggtctatactgatgttgaagagtgacctacatgagga aaactcttggagagattaaaaaatcaggaggagactccaaactttaagtatgaaaaaactttgatccttaagaccctcttgt ggttttattttttatctggttttgtggtcttcgt.
```

Mutant VSV oncolytic viruses are described in WO 2001019380, which is incorporated by reference for the teaching of how to make and use these viruses.

Insertion Location

The disclosed compositions and methods encompass expression systems comprising a viral vector comprising one or more heterologous nucleotide sequence(s), such as, a nucleotide sequence encoding a Smac protein. The smac gene can be inserted anywhere in the virus genome as long as it is expressed. In preferred embodiments, the smac gene is inserted such that its expression is delayed until after viral replication. The VSV genome comprises a nucleoprotein (N) gene, a phosphoprotein (P) gene, a matrix protein (M) gene, glycoprotein (G) gene, and the large (L) polymerase protein. The mRNA levels of VSV genes descend from the N gene (close to the 3' end) to the L gene (close to the 5' end) in VSV infection. N and P proteins are required for supporting viral replication, whereas M protein is required for virus assembly. Therefore, in some embodiments, the smac gene is inserted into the VSV genome after the N, P and M proteins so that Smac reaches a significant level only when viral production is well-established. In some cases, the smac gene is inserted after the M gene in viruses from the order of Mononegavirales. Comparable locations within other viral genomes can be determined and used in the disclosed vectors.

Therapeutic Genes

In some embodiments, the virus further expresses at least one therapeutic gene inserted in the viral genome. A vast number of therapeutic genes may be envisaged in the context of the disclosed vectors, such as those encoding polypeptides that can compensate for defective or deficient proteins in the subject, or those that act through toxic effects to limit or remove harmful cells from the body or those that encode immunity conferring polypeptides. In some cases, the disclosed onolytic virus carries a therapeutic gene selected from the group consisting of genes encoding suicide gene products and immunostimulatory proteins.

The term "suicide gene" refers to a gene coding for a protein able to convert a precursor of a drug into a cytoxic compound. Suicide genes comprise but are not limited to genes coding protein having a cytosine deaminase activity, a thymidine kinase activity, an uracil phosphoribosyl transferase activity, a purine nucleoside phosphorylase activity and a thymidylate kinase activity. In some cases, the suicide gene encodes a protein having at least a CDase activity. Alternatively or in combination, the virus of the invention can carry in its viral genome a suicide gene encoding a polypeptide having uracil phosphoribosyl transferase (UPRTase) activity.

The "proapoptotic products" refers to proteins that induce cell apoptosis when present at a significant level. Genes that code for proapoptotic proteins comprise but are not limited to genes coding for proapoptotic cytokines, fas ligands, FADD, caspases-8, -9, -3, Smac/DIABLO, cytochrome c, IFN-beta, RANTES, IP-10, TNF-alpha, CD95 ligands, and TRAIL in tumor cells; that activate tumor suppressing genes such as p53 in tumor cells; or that activate caspases-8, -9, -3, Smac/DIABLO, cytochrome c present in tumor cells.

As used herein, the term "immunostimulatory protein" refers to a protein which has the ability to stimulate the immune system, in a specific or non-specific way. A vast number of proteins are known in the art for their ability to exert an immunostimulatory effect. Examples of suitable immunostimulatory proteins in the context of the invention include without limitation cytokines, with a specific preference for interleukins (e.g. IL-2, IL-6, IL-12, IL-15, IL-24), chemokines (e.g. CXCL10, CXCL9, CXCL11), interferons (e.g. IFNγ, IFNα), tumor necrosis factor (TNF), colony-stimulating factors (e.g. GM-CSF, C-CSF, M-CSF . . . ), APC (for Antigen Presenting Cell)-exposed proteins (e.g. B7.1, B7.2 and the like), growth factors (Transforming Growth Factor TGF, Fibroblast Growth Factor FGF, Vascular Endothelial Growth Factors VEGF, and the like), MHC antigens of class I or II, apoptosis inducers or inhibitors (e.g. Bax, Bcl2, BclX . . . ), cytostatic agents (p21, p16, Rb . . . ), immunotoxins, antigenic polypeptides (antigenic polypeptides, epitopes, and the like) and markers (beta-galactosidase, luciferase . . . ). In some cancers, the immunostimulatory protein is an interleukin or a colony-stimulating factor, with a specific preference for GM-CSF.

The practice of the disclosed compositions and methods will employ, unless otherwise indicated, conventional techniques of molecular biology (including recombinant techniques), microbiology, cell biology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

Compositions

Also disclosed are host cells comprising (i.e., transformed, transfected or infected with) the viral vectors or particles described herein. Both prokaryotic and eukaryotic host cells, including insect cells, can be used as long as sequences requisite for maintenance in that host, such as appropriate replication origin(s), are present. For convenience, selectable markers are also provided. Host systems are known in the art and need not be described in detail herein. Prokaryotic host cells include bacterial cells, for example, *E. coli, B. subtilis*, and mycobacteria. Among eukaryotic host cells are yeast, insect, avian, plant, *C. elegans* (or nematode) and mammalian host cells. Examples of fungi (including yeast) host cells are *S. cerevisiae, Kluyveromyces lactis* (*K. lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, mouse L cells, LNCaP cells, Chinese hamster ovary (CHO) cells, human embryonic kidney (HEK) cells, and African green monkey cells. *Xenopus laevis* oocytes, or other cells of amphibian origin, may also be used.

Also disclosed are compositions, including pharmaceutical compositions, containing the viral vectors described herein. Such compositions are useful for administration in vivo, for example, when measuring the degree of transduction and/or effectiveness of oncolytic activity toward a malignant cell. Compositions can comprise a viral vector(s) and a suitable solvent, such as a physiologically acceptable buffer. These are well known in the art. In other embodiments, these compositions further comprise a pharmaceutically acceptable excipient. These compositions, which can comprise an effective amount of a viral vector in a pharmaceutically acceptable excipient, are suitable for systemic or local administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in Remington's Pharmaceutical Sciences, 19th Edition, Mack Publishing (1995). Compositions also include lyophilized and/or reconstituted forms of the VSV vectors (including those packaged as a virus) of the invention.

Also disclosed are kits containing viral vector(s) disclosed herein. These kits can be used for example for producing proteins for screening, assays and biological uses, such as treating a tumor. Procedures using these kits can be performed by clinical laboratories, experimental laboratories, medical practitioners, or private individuals. The kits can comprise a viral vector described herein in suitable packaging. The kit may optionally provide additional components that are useful in the procedure, including, but not limited to, buffers, developing reagents, labels, reacting surfaces, means for detection, control samples, instructions, and interpretive information. The kit may include instructions for administration of a viral vector.

Methods of Using Recombinant Viral Vectors of the Invention

The subject viral vectors and viral particles can be used for a wide variety of purposes, which will vary with the desired or intended result.

Accordingly, disclosed are methods for producing oncolytic activity in a tumor cell, comprising the step of contacting the cell with a recombinant vector, or viral particles comprising the vector, disclosed herein. Disclosed herein are methods for suppressing tumor growth, comprising the step of contacting the tumor with a recombinant vector, or viral particles comprising the vector disclosed herein.

The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed recombinant vector, or viral particles comprising the vector, can be administered to an individual in need. Such an individual can comprise malignant cells or tumor cells or can be at risk for developing malignant cells or tumor cells or development of metastatic disease. The disclosed constructs can be used to treat local tumors or metastatic disease. A variety of cells and cells lines, including ovarian carcinoma cells, fibrosarcoma, lung carcinoma, melanoma, prostate carcinoma, lung carcinoma and leukaemia cells are sensitive to infection by oncolytic viruses including VSV.

Methods of Administration

Many methods may be used to administer or introduce the disclosed vectors or viral particles into individuals, including but not limited to, oral, intradermal, intramuscular, intraperitoneal, intravenous, intratumoral, subcutaneous, and intranasal routes. The individual to which a disclosed vector or viral particle is administered is a primate, or in other examples, a mammal, or in other examples, a human, but can also be a non-human mammal including but not limited to cows, horses, sheep, pigs, fowl, cats, dogs, hamsters, mice and rats. In the use of a disclosed vector or viral particles, the individual can be any animal in which a disclosed vector or virus is capable of growing and/or replicating. The present invention encompasses compositions comprising a disclosed vector or viral particles wherein said compositions can further comprise a pharmaceutically acceptable carrier. The amount of vector(s) to be administered will depend on several factors, such as route of administration, the condition of the individual, the degree of aggressiveness of the malignancy, and the particular vector employed. Also, the disclosed vector may be used in conjunction with other treatment modalities.

If administered as a disclosed virus, from about $10^2$ up to about $10^8$ p.f.u. (or TCID50), in other examples, from about $10^3$ up to about $10^6$ p.f.u. (or TCID50), and in other examples, from about $10^4$ up to about $10^5$ p.f.u. (or TCID50) can be administered. If administered as a polynucleotide construct (i.e., not packaged as a virus), about 0.01 µg to about 100 µg of a disclosed viral construct can be administered, in other examples, 0.1 µg to about 500 µg, and in other examples, about 0.5 µg to about 200 µg can be administered. More than one viral vector can be administered, either simultaneously or sequentially. Administrations are typically given periodically, while monitoring any response. Administration can be given, for example, intratumorally, intravenously or intraperitoneally.

Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder, a solution or water free concentrate in a hermetically sealed container such as an ampoule, a bottle or sachette indicating the quantity of active agent. Where the composition is administered by injection, an ampoule of sterile diluent can be provided so that the ingredients may be mixed prior to administration, or a solution is provided.

In a specific embodiment, a lyophilized recombinant viral vector disclosed herein is provided in a first container; a second container comprises diluent consisting of an aqueous solution of 50% glycerin, 0.25% phenol, and an antiseptic (e.g., 0.005% brilliant green).

The precise dose of viral vector or viral particles to be employed in the formulation will also depend on the route of administration, and the nature of the patient, and should be decided according to the judgment of the practitioner and each patient's circumstances according to standard clinical techniques. The exact amount of viral vector or viral particles utilized in a given preparation is not critical, provided that the minimum amount of virus necessary to produce oncolytic activity is given. A dosage range of as little as about 10 micrograms, up to amount a milligram or more, is contemplated.

Specific Features

The present disclosure will be better understood upon review of the following features, which should not be confused with the claims.

Feature 1. A recombinant viral vector comprising a nucleic acid encoding a Second Mitochondria-derived Activator of Caspases (SMAC) protein inserted within an RNA virus genome, wherein the SMAC protein specifically binds to at least a portion of an Inhibitor of Apoptosis Protein (IAP).

Feature 2. The recombinant vector of Feature 1, wherein the virus is negative-strand RNA viruses (NSV).

Feature 3. The recombinant vector Feature 1, wherein the oncolytic virus is positive strand RNA viruses (PSV).

Feature 4. The recombinant vector Feature 1, wherein the virus is a paramyxovirus.

Feature 5. The recombinant vector Feature 4, wherein the virus comprises measles virus (MV).

Feature 6. The recombinant vector Feature 1, wherein the virus is a rhabdovirus.

Feature 7. The recombinant vector Feature 6, wherein the virus comprises vesicular stomatitis virus (VSV).

Feature 8. The recombinant vector of any preceding Feature, wherein the virus genome comprises at least a nucleoprotein (N) gene, a phosphoprotein (P) gene, and a matrix protein (M) gene, wherein the nucleic acid encoding SMAC is inserted after the M gene.

Feature 9. The recombinant vector of Feature 8, wherein the virus genome comprises a glycoprotein (G) gene that encodes a modified G protein that comprises an inserted cancer targeting domain.

Feature 10. The recombinant vector of Feature 9, wherein the targeting domain comprises an RGD sequence that binds an integrin.

Feature 11. The recombinant vector of Feature 10, wherein the G protein comprises the amino acid sequence SEQ ID NO:6.

Feature 12. The recombinant vector of any one of Features 8 to 11, wherein the SMAC protein comprises the amino acid sequence SEQ ID NO:1, or a conservative variant thereof that specifically binds IAP.

Feature 13. The recombinant vector of any preceding Feature, wherein the SMAC protein comprises a full-length SMAC protein.

Feature 14. The recombinant vector of any preceding Feature, wherein the SMAC protein lacks a mitochondria-targeting sequence.

Feature 15. The recombinant vector of Feature 14, wherein the SMAC protein comprises the amino acid sequence SEQ ID NO:2, or a conservative variant thereof that specifically binds IAP.

Feature 16. The recombinant vector of any one of Features 1 to 15, wherein further comprising a nucleic acid encoding a microRNA-155.

Feature 17. The recombinant vector of Feature 16, wherein the nucleic acid encoding a microRNA-155 has the nucleic acid sequence SEQ ID NO:7.

Feature 18. The recombinant vector of any preceding Feature 15, wherein the recombinant vector comprises the nucleic acid sequence SEQ ID NO:8, 9, 10, or 11.

Feature 19. A cell comprising the recombinant vector of any one of Features 1 to 18.

Feature 20. A recombinant viral particle comprising the recombinant vector of any one of Features 1 to 18.

Feature 21. A composition comprising the recombinant viral particle of Feature 20 in pharmaceutically acceptable excipient.

Feature 22. A method of treating a subject with a tumor, comprising administering to the subject an effective amount of the composition of Feature 21.

Feature 23. The method of Feature 22, wherein the tumor comprises a breast tumor.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Autophagy is an essential mechanism for cells to maintain their survival. Cancer cells live in an abnormal environment. There is substantial evidence indicating that autophagy plays a central role in cancer biology (Lippai, M. and Z. Szatmari, Cell Biol Toxicol, 2017 33(2):145-168). On the one hand, autophagy in normal cells can suppress tumorigenesis. In a recent publication, it has been shown that mutations in cancers, especially ovarian cancer (OV), resulted in loss of autophagy functions (Delaney, J. R., et al., Nat Commun, 2017 8:14423). Using the Cancer Genome Atlas (TCGA) data (Kandoth, C., et al., Nature, 2013 502(7471):333-9), the authors discovered that 48% of the ovarian tumors do not contain mutations in oncogenes or tumor suppressors, other than TP53. It appears that somatic copy-number alterations (SCNAs) are the main drivers in OV and other cancers. The most suppressed pathways by SCNAs are autophagic and lysosomal pathways across all cancer types (Delaney, J. R., et al., Nat Commun, 2017 8:14423). MAP1LC3B (LC3) and BECN1 were found as most impactful genes. These data are consistent with previous publications.

Alternatively, autophagy can also render tumor cells resistant to treatment of anticancer drugs. In a study of multiple myeloma (MM), it was shown that higher expression of high mobility group box 1 (HMGB1) is linked with the poor prognosis of MM based on gene expression profiling (Roy, M., et al., Theranostics, 2016 6(12):2209-2224). Endogenous HMGB1 is an autophagy regulator by binding Beclin-1 to displace Bcl-2 when translocated into cytosol (Tang, D., et al., J Cell Biol, 2010 190(5):881-92). In ARH-77, ANBL-6 and ARP-1 cells, expression of HMGB1 is elevated and knock-down of HMGB1 decreases survival. The level of Beclin-1 and LC3 correlates with that of HMGB1. An autophagy inhibitor, lycorine, can induce degradation of HMGB1, thus inhibit the dissociation of Bcl-2 from Beclin-1. At the same time, lycorine can sensitize MM cells to the treatment of bortezomib. Sensitizing MM to bortezomib treatment by lycorine inhibition of autophagy was further confirmed in a mouse xenograft model.

The cross-talk between autophagy and apoptosis is also critical in cancer biology, but the relationship between the two pathways is complicated (Marino, G., et al., Nat Rev Mol Cell Biol, 2014 15(2):81-94); Liu, G., et al., Int J Mol Sci. 2017 18(2)). Both autophagy and apoptosis may be induced by stress. Usually, autophagy is initiated before apoptosis. Apoptosis is activated when stress is prolonged for a critical duration or exceeds the intensity threshold. At the same time, persistent activation of autophagy may also lead to autophagic programmed cell death. There is therefore a concern as to how to prevent autophagy from counteracting apoptosis or to direct autophagy to promote apoptosis in cancer therapy. One of the critical crossing point between the two pathways is the interaction of Beclin-1 with Bcl-2. Binding of Beclin-1 to Bcl-2 inhibits both autophagy and apoptosis. When Bcl-2 is phosphorylated by JNK1 that is activated under stress, Beclin-1 is dissociated from Bcl-2 and activates autophagy. Meanwhile, phosphorylated Bcl-2 binds Bax in mitochondria to suppress apoptosis. In this scenario, activation of autophagy actually suppresses apoptosis.

Another important mechanism of apoptosis inhibition by autophagy is mitophagy (Kulikov, A. V., et al., Biochem Biophys Res Commun, 2017 482(3):432-439; Youle, R. J. and D. P. Narendra, Nat Rev Mol Cell Biol, 2011 12(1):9-14). Mitophagy refers to selective degradation of mitochondria by autophagy. Since the intrinsic apoptosis is induced by the disruption of mitochondrial outer membrane, mitophagy will severely limit apoptosis. Normally, mitophagy is prevented because the kinase PINK1 (PTEN-induced putative kinase 1) in the mitochondrial membrane is cleaved by a protease in the mitochondrial membrane. Under stress, PINK1 will accumulate on the outer membrane of mitochondria and recruit another protein PARKIN (Parkinson's disease protein) to mitochondria. PARKIN is an E3 ubiquitin ligase that ubiquitinylates proteins in the outer membrane of mitochondria. The adaptor protein p62/A170/SQSTM1 recognizes the ubiquitinylated proteins and induce fusion of the mitochondria with LC3 II-autophagosomes.

On the other hand, activated apoptotic caspases can downregulate autophagy to abort its cytoprotective function (Marino, G., et al., Nat Rev Mol Cell Biol, 2014 15(2):81-94). Several autophagy proteins are cleaved by activated caspases, such as ATG3, Beclin-1 and ATG5. Beclin-1 plays a central role in initiation of autophagy by forming a core complex with VPS34 and other proteins, leading to the isolated membrane structure. Protein light chain 3 (LC3) is a key protein that binds in the membrane of autophagosomes. During activation of autophagy, LC3 is first cleaved by ATG4 to LC3 II. ATG3 mediates LC3 II conjugation to phosphatidylethanolamine (PE) by ATG7. LC3 II/PE binds in the membrane of autophagosomes. Cleavage of Beclin-1 and ATG3 by active caspases terminates autophagy. At the same time, the C-terminal domain of Beclin-1 resulted from the caspase cleavage binds mitochondria to cause the release of cytochrome c, which further activates apoptosis. The same activation of apoptosis is also observed with the N-terminal domain of ATG5 cleaved by calpain.

The interplay between autophagy and apoptosis is much more complicated than what we have briefly discussed. However, a primary concern is how to manipulate the two pathways in order to construct an effective mechanism for cancer treatment. Autophagy tends to suppress apoptosis in most cases. When the protective mechanism of autophagy is subverted, apoptosis may be induced more readily. Disclosed is a strategy to achieve the latter.

There are many examples showing that inhibition of autophagy can sensitize tumor cells to treatment by anticancer drugs. In acute myeloid leukemia cells that are resistant to bromodomain and extraterminal domain (BET) inhibitor JQ1, expression of Beclin-1 is upregulated and autophagy is activated by JQ1 (Jang, J. E., et al., Autophagy, 2017:0; Jang, J. E., et al., Clin Cancer Res, 2016). Knock-down of BECN1/Beclin-1 gene expression by siRNA or addition of autophagy inhibitor 3-methyladenine (3-MA) increases JQ1-induced apoptosis in resistant cells. In MCF-7 breast cancer cells, treatment with a proteasome inhibitor bortezomib (Velcade®) also activates autophagy (Yao, F., et al., Mol Med Rep, 2012 5(1):84-8). Treatment of MCF-7 cells with bortezomib induced a dose-dependent increase in LC3-II and a time-dependent accumulation of GFP-LC3 puncta. When 3-MA is added, inhibition of MCF-7 proliferation by bortezomib is enhanced.

When working on oncolytic vesicular stomatitis virus (VSV), inhibition of autophagy enhances VSV-induced apoptosis (Malilas, W., et al., Int J Oncol, 2014 44(4):1177-84). VSV infection induces apoptosis through the intrinsic mitochondrial pathway (Pearce, A. F. and D. S. Lyles, J Virol, 2009 83(18):9102-12; Balachandran, S., et al., J Virol, 2000 74(3):1513-23; Kopecky, S. A. and D. S. Lyles, J Virol, 2003 77(8):4658-69). Cancer upregulated gene 2 (CUG2) is upregulated in numerous tumor cells, such as ovarian, liver, colon, and lung cancer cells, and plays a critical role in tumorigenesis (Lee, S., et al., Biochem Biophys Res Commun, 2007 360(3):633-9). When CUG2 is overexpressed, it confers resistance to VSV infection (Malilas, W., et al., Cancer Gene Ther, 2013 20(2):125-32). When Beclin-1 or ATG5 was knocked-down by siRNA in CUG2-overexpressing cells, these cells became sensitive to VSV killing, suggesting that autophagy played a protective role in CUG2-overexpressing cells (Malilas, W., et al., Int J Oncol, 2014 44(4):1177-84). The same sensitization was also observed for another oncolytic virus, Newcastle disease virus (NDV), that is in the same virus class, i.e. negative strand RNA virus, as VSV. In lung cancer spheroids enriched with cancer stem cells, infection by NDV induced autophagy as show by increased degradation of LC3 and p62 (Hu, L., et al., Am J Cancer Res, 2015 5(12):3612-23). Inhibition of autophagy with chloroquine enhanced apoptotic caspase-3 processing induced by NDV infection in 3D culture of the spheroids, whereas treatment by rapamycin, an autophagy inducer, reduced apoptosis in NDV infection. The same potentiation by autophagy inducers/inhibitors was also observed in A549 lung cancer cell lines resistant to cisplatin (A549/DDP) or paclitaxel (A549/PTX) (Jiang, K., et al., BMC Cancer, 2014 14:551). Resistance to NDV-induced apoptosis is directly related to mitophagy (Meng, G., et al., Oncotarget, 2014 5(15):6365-74). In NDV infected cells, degradation of LC3 and SQSTM1 was increased. More importantly, autophagy induced by NDV actually blocked apoptosis as indicated by degradation of caspase 9 and 3 (Meng, G., et al., Oncotarget, 2014 5(15):6365-74). Suppression of apoptosis supported viral replication, and inhibition of autophagy by 3-MA restored cell killing by NDV. Further studies showed that SQSTM1 mediates mitophagy in NDV infected cells as indicated by colocalization of mitochondria and autophagosomes, which can reduce the release of cytochrome c (Meng, G., et al., Oncotarget, 2014 5(15):6365-74). Autophagy may therefore be induced by infection of oncolytic virus VSV or NDV, and activation of autophagy can support virus replication (Chakrabarti, A., et al., J Virol, 2012 86(20):11311-21; Richetta, C., et al., PLoS Pathog, 2013 9(9):e1003599).

However, activation of autophagy in the cancer cells appear to play a cytoprotective role by suppressing apoptosis. Inhibition of autophagy can sensitize cancer cells to killing by oncolytic VSV or NDV. One interesting observation is that when 3-MA was added to inhibit autophagy after 24 hr of NDV infection, enhanced cell killing was achieved, further suggesting that autophagy should be inhibited at a later stage to allow efficient virus replication in order to induce apoptosis effectively (Meng, G., et al., Oncotarget, 2014 5(15):6365-74). Thus, the optimal design can be a mechanism to inhibit autophagy after efficient virus replication. Disclosed herein is an armed VSV in order to achieve that goal.

Armed VSVs have been developed to enhance killing of cancer cells. In one case, the gene for interferon β was inserted between the G and L viral genes (VSV-IFNβ) (Obuchi, M., et al. J Virol, 2003 77(16):8843-56). Expression of IFNs enhanced cancer cell killing (Willmon, C. L., et al., Cancer Res, 2009 69(19):7713-20; Saloura, V., et al., Hum Gene Ther, 2010 21(1):51-64; Kurisetty, V. V., et al., Head Neck, 2014 36(11):1619-27; Patel, M. R., et al., Oncotarget, 2015 6(32): 33165-77). Based on VSVMΔ51 of which residue 51 in the matrix protein (M) has been mutated in order to limit VSV spread to normal cells (Goel, A., et al., Blood, 2007 110(7):2342-50), the gene for interferon γ was inserted between the G and L viral genes (VSV MA51-IFNγ) (Bourgeois-Daigneault, M. C., et al., Mol Ther Oncolytics, 2016 3:16001). This virus also showed enhanced antitumor activities. The mechanism of these armed VSVs is to enhance immune responses to cancer cells, but not directly killing cancer cells by VSV infection.

The goal of this example is to enhance VSV's direct killing of cancer cells. In TRAIL-resistant breast cancer cells, overexpression of Smac/DIABLO sensitized these cells to chemotherapeutic drugs (tamoxifen, doxorubicin, or paclitaxel), and irradiation (Fandy, T. E., et al. Mol Cancer, 2008 7:60). Smac/DIABLO was shown to have enhanced interaction with IAPs. Rhabdomyosarcoma (RMS) is the most common soft tissue sarcoma in children. RMS may be resistant to many treatments, especially Smac mimetic compounds (SMCs, e.g. LCL161) (Houghton, P. J., et al., Pediatr Blood Cancer, 2012 58(4):636-9). However, combination of VSV VSVMΔ51 and SMC LCL161 can eradicate RMS tumors in a mouse model, indicating the potential of arming oncolytic VSV with Smac (Dobson, C. C., et al., Oncotarget, 2017 8(2):3495-3508).

Disclosed is a VSV where the Smac gene (full length or A55) has been inserted between the M and G genes in the VSV genome (FIG. 1). Insertion of Smac between the M and G genes have the minimum impact on viral replication. The level of Smac expression is dependent on the establishment of VSV replication, which implies that the enhancement of Smac induced intrinsic apoptosis will not significantly limit VSV replication due to the delay. Since VSV induces apoptosis via the mitochondrial pathway, Smac will reinforce apoptotic activities of VSV. In addition, induction of intrinsic apoptosis could also suppress autophagy to eliminate its cytoprotective effects. Several lines of experiments are designed to test this virus.

Cross-Talk Between Autophagy and Apoptosis in VSV Oncolysis.

When Smac is released into the cytosol, it will bind IAP to prevent its association with caspase 9, thereby promoting the activity of caspase 9, followed by caspase 3 and apoptosis. Some Smac-mimetic peptides showed potent proapoptotic activities, but their deliveries remain a challenge. One of the effective ways to deliver Smac is to express it by a virus vector. The Smac gene (full length or A55) is therefore inserted as an expression unit in the VSV genome (VSV-S). This unit is inserted between the M and G genes of VSV (FIG. 1). The mRNA levels of VSV genes descend from the N gene (close to the 3' end) to the L gene (close to the 5' end) in VSV infection (Ball, L. A., et al., J Virol, 1999 73(6): 4705-12; Wertz, G. W., et al. Proc Natl Acad Sci USA, 1998 95(7):3501-6). N and P proteins are required for supporting viral replication. By having the inserted expression unit after the M gene, Smac reaches a significant level only when viral replication is well-established. In addition, this delay can also help to achieve better control of autophagy/mitophagy, since delayed application of autophagy inhibitors has an enhanced effect in promoting oncolysis by VSV and Newcastle disease virus (Malilas, W., et al., Int J Oncol, 2014 44(4):1177-84; Hu, L., et al., Am J Cancer Res, 2015 5(12):3612-23; Jiang, K., et al., BMC Cancer, 2014 14:551; Meng, G., et al., Oncotarget, 2014 5(15):6365-74; Samuel, S., et al., Mol Ther, 2013 21(7):1413-23; Shulak, L., et al., J Virol, 2014 88(5):2927-40).

VSV-S is generated by reverse genetics (Whelan, S. P., et al., Proc Natl Acad Sci USA, 1995 92(18):8388-92). Briefly, the coding sequence of full length Smac or A55 Smac was flanked by the sequences to form a new ORF, plus CT for a new gene junction (FIG. 1). This segment was cloned in the VSV genome by blunt end cloning. The correct insert was identified by DNA sequencing and this genome plasmid was cotransfected with pN, pP and pL into BHK-21 cells infected by a vaccinia virus that expressed T7 polymerase. After a stable virus stock was established, the growth curve of VSV-S was compared with that of wt VSV. A mutant virus with full length Smac inserted was rescued. Its growth curve in HeLa cells was compared with that of wt VSV by (FIG. 2). VSV-S grew to similar titers as wt VSV, suggesting that insertion of Smac did not compromise VSV replication. Expression of Smac in accordance with virus growth was examined (FIG. 3).

To evaluate the potential of killing cancer cells, T-47D breast cancer cells were seeded in 12-well plates and infected with VSV-S at MOI=5. Cell death was evaluated using a Promega kit (CellTiter 96@(MTT)), following the manufacturer's protocol (FIG. 4). wt VSV expressing a mCherry fused P protein was used as the control. Since T-47D has a high level of XIAP expression (Foster, F. M., et al., Breast Cancer Res, 2009 11(3):R41), wt VSV apparently could not kill them effectively. VSV-S was able to kill T-47D more effectively. After 48 hr of infection, VSV-S killed more than 60% of T-47D cells, whereas the wt VSV could only kill less than 10%.

Test the Efficacy of Improved Oncolytic VSV in Animal Models

A simple animal model is the xenograft in nude mice using one of the typical cancer cell lines. VSV-S was tested in T-47D xenografts. After tumors were established, $1.0\times10^5$ PFU of VSV-S per 0.4 $cm^3$ or VSV control in equal amounts were intratumorally injected in each mouse. The size of the tumors was monitored, and mice were sacrificed and the tumors were removed. It was generally concluded that VSV-S can significantly reduce the size of tumor xenografts when injected intratumorally.

Example 2

To establish a syngeneic model, 1 million Panc02 cells were subcutaneously injected in the flank of C57BL/6 mice. After 12 days, the tumors grew to a size of about 100-200 $mm^3$. A dose of $1\times10^5$ PFU of VSV-S in 0.1 mL was intratumorally injected into the tumor (two mice). The same dose of wt VSV was injected in parallel mice as the control. Tumor volumes were monitored for up to 9 days (FIG. 5). Mice were euthanized at the end of the study, and tumors were removed and weighed (FIG. 5). The data showed that VSV-S could suppress tumor growth more effectively than wt VSV. The number of animals tested in this preliminary study is small because this is only a pilot study. This experiment is repeated with more subjects (n=12) and higher dosage.

Ex vivo activity: Tissues from an anal sac carcinoma were collected. Slices of the tumor tissues were washed three times in DPBS and then placed in a 24-well tray as pairs. $1\times10^5$ PFU of VSV-S was used to infect each well for 1 hr at 37° C. wt VSV with a mCherry fused P protein was used as the control, which allows visualization of VSV infection by red fluorescent imaging. After 1 hr virus absorption, the virus inoculum was removed and fresh media were added. At 72 hr postinfection, the tumor tissue of a canine anal sac carcinoma was clearly infected by wt VSV as shown in FIG. 6A. Analysis of apoptosis induced by VSV-S was carried out by monitoring cleavage of PARP (FIG. 6B), showing the robustness of VSV-S in inducing apoptosis.

Mechanism of Action: HeLa cells were infected with VSV-S and wt VSV control. Western blot analyses were carried out to monitor expression of Smac (FIG. 6). Since Smac was expressed by VSV-S during virus infection, there were increasing levels of Smac expression. By 24 hours post-infection, the Smac level remained to be high despite that a large portion of the cells had died as indicated by the reduced level of GAPDH (FIG. 7). The protein expressed by VSV-S was the full length Smac, which was processed to the mature Smac (A55 Smac). There was an increased level of mature Smac, but the majority of VSV-S expressed Smac remained to be full length. The significance of this may be that Smac expression by VSV-S did not result in premature release of A55 Smac so the virus could continue to be produced before activation of apoptosis in the infected cell. In VSV infected cells, on the other hand, the level of endogenous mature Smac began to fall 12 hours postinfection, and fell undetectable 24 hours postinfection. Much less cell death was observed in VSV infected cells as indicated by constant levels of GAPDH. One way for VSV to deplete mature Smac is by inducing mitophagy because mature Smac resides in the intermembrane space of mitochondria. Another potential mechanism of Smac removal is by Smac ubiquitination activated by wt VSV infection (Hao, Y., et al., Nat Cell Biol, 2004 6(9):849-60).

To check apoptosis, MDA-MB 231 breast cancer cells were infected with VSV-S at MOI=10 (FIG. 8). wt VSV was included for comparison. Based on the cleaved products of PARP, caspase-9 and caspase-3, there was massive apoptosis induced by VSV-S infection (FIG. 8A). On the other hand, wt VSV induced apoptosis to some degree based on cleavage of PAPR. However, no cleavage of caspase-9 and caspase-3 was observed. This is consistent with result in which endogenous Δ55 Smac was diminished so that the intrinsic pathway was not activated. A similar pattern of caspase cleavage was also observed in VSV-S infection of T-47D cells. To confirm that the intrinsic pathway is responsible for the programmed cell death induced by VSV-S infection, VSV-S infection was repeated in the presence of various caspase inhibitors (FIG. 8B). Inhibitors of caspase-9 and caspase-3 were able to protect the cells from VSV-S induced programmed cell death, confirming that the intrinsic pathway is the major pathway for VSV-S induced apoptosis because the caspase-8 inhibitor could not protect the cells from VSV-S infection. A similar pattern of caspase cleavage was also observed in VSV-S infection of T-47D cells (FIG. 8C).

Example 3

The VSV G protein uses the LDL receptor or its family members as the host receptor for virus entry (Finkelshtein, D., et al., Proc Natl Acad Sci USA, 2013 110(18):7306-11). Since this family of receptors is expressed in many cell types, wt VSV can infect almost all human cells. In order to make VSV specifically targeting tumors, a target specific protein domain in VSV G is inserted. Integrin αvβ3 is such a candidate because it is highly expressed in endothelial cells of tumor blood vessels (Demircioglu, F., et al., Curr Opin Cell Biol, 2016 42:121-127; Atkinson, S. J., et al., Biochem Soc Trans, 2014 42(6):1590-5).
Experimental Design Design of a tumor targeting VSV G. The G protein of VSV is responsible for attachment to the host receptor and induction of membrane fusion when the virus is exposed to low pH in the endosome during virus entry. A targeting domain is inserted in the G protein so the modified G will target VSV to cancer. The first step is to select the site of insertion. The crystal structure of the G protein has been determined for both pre-(neutral pH) and post-fusion (low pH) forms (Roche, S., et al., Science, 2007 315(5813):843-8; Roche, S., et al., Science, 2006 313(5784):187-91). The site at 191 has been shown to be permissive for insertion of a six amino acid peptide (Schlehuber, L. D., et al., J Virol, 2004 78(10):5079-87). This is therefore a good site for insertion of the targeting domain. The site has Gly at the C-terminal side. A flexible linker can also be added to the N-terminal side to allow more flexibility.

The next step is to select a targeting protein domain. RGD is a sequence that binds integrin αvβ3 with a high affinity (Kapp, T. G., et al., Sci Rep, 2017 7:39805). It may be inserted at the 191 site with proper linkers (e.g GRGDS (SEQ ID NO:4))

To verify that insertion of RGD does not change the ability of VSV G to bind its receptor and mediate membrane fusion, the modified VSV G and the wt VSV G are expressed using the vector pCAGGS. The plasmids are transfected unto 293T cells with polyethylenimine. After 24 h, the cells are fixed by 4% paraformaldehyde. One is permeabilized with 0.2% Triton X-100 for 5 min, the other without permeabilization. After blocking for 1 h in PBS containing 5% goat serum, all cells are incubated with polyclonal anti-VSV G at 4° C. overnight. Cells are then washed with PBS following incubation with Alexa Fluor®488-Conjugated goat anti-rabbit secondary antibody for 1 h at 37° C. After washing, cells are stained with DAPI for 10 min, and then mounted onto microscope slides. The slides are imaged by a Keyence Imaging system. This experiment is to ensure that the insertion of the targeting domain does not block the expression and effective transport to the cellular membrane. The next experiment is to test the ability of the modified VSV G to induce membrane fusion. Following the protocol in (Schlehuber, L. D., et al., J Virol, 2004 78(10):5079-87), the cells expressing the G proteins are exposed to pH 5.2 for 1 min, and again 1 h later. The functional G protein induces cell-cell fusion and syncytial formation.

VSV G and RGD inserted G (RGD G) were cloned in pCAGGS. After transfection into 293T cells, the expression of these proteins was detected by Western blot using a mAb to VSV G (FIGS. 9A and 9B). RGD G showed the same level of expression as wt VSV G. To demonstrate fusion activities of RGD G, acid treatment of the cells was carried out and the nuclei were stained with DAPI (FIG. 9B). This study confirmed that insertion of the GRGDS (SEQ ID NO:4) sequence at 191 site did not disrupt expression and fusogenic properties of the G protein. Recombinant VSV that contains the Smac insert and the RGD G has been rescued.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant viral vector comprising a nucleic acid encoding a Second Mitochondria-derived Activator of Caspases (SMAC) protein inserted within the genome of a vesicular stomatitis virus (VSV),
    wherein the SMAC protein consists of the amino acid sequence SEQ ID NO:1 or 2, or a conservative variant thereof having an IAP-binding motif comprising the amino acid sequence SEQ ID NO:3 and that specifically binds to at least a portion of an Inhibitor of Apoptosis Protein (IAP),
    wherein the virus genome comprises at least a nucleoprotein (N or NP) gene, a phosphoprotein (P) gene, a glycoprotein (G) gene, and a matrix protein (M) gene,
    wherein the G gene encodes a modified G protein that consists of the amino acid sequence SEQ ID NO:5 with a peptide sequence six amino acids or less comprising an RGD sequence inserted after amino acid position 190 of SEQ ID NO:5, and
    wherein the nucleic acid encoding SMAC protein is inserted between the M gene and glycoprotein (G) gene.

2. The recombinant vector of claim 1, wherein the G protein consists of the amino acid sequence SEQ ID NO:6.

3. The recombinant vector of claim 1, wherein the vector further comprises a nucleic acid encoding a microRNA-155.

4. The recombinant vector of claim 3, wherein the nucleic acid encoding a microRNA-155 has the nucleic acid sequence SEQ ID NO:7.

5. The recombinant vector of claim 1, wherein the recombinant vector comprises the nucleic acid sequence SEQ ID NO:8, 9, 10, or 11.

6. An isolated cell comprising the recombinant vector of claim 1.

7. A recombinant viral particle comprising the recombinant vector of claim 1.

8. A composition comprising the recombinant viral particle of claim 7 in pharmaceutically acceptable excipient.

9. A method of treating a subject with a tumor, comprising administering to the subject an effective amount of the composition of claim 8.

10. The method of claim 9, wherein the tumor comprises a breast tumor.

* * * * *